US012746354B2

(12) United States Patent
Mazzone

(10) Patent No.: US 12,746,354 B2
(45) Date of Patent: Sep. 29, 2026

(54) RESPIRATORY PRESSURE THERAPY DEVICE

(71) Applicant: RESMED PTY LTD, Bella Vista (AU)

(72) Inventor: Damien Julian Mazzone, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 632 days.

(21) Appl. No.: 18/251,180

(22) PCT Filed: Nov. 2, 2021

(86) PCT No.: PCT/AU2021/051291
§ 371 (c)(1),
(2) Date: Apr. 28, 2023

(87) PCT Pub. No.: WO2022/094655
PCT Pub. Date: May 12, 2022

(65) Prior Publication Data

US 2023/0398318 A1 Dec. 14, 2023

Related U.S. Application Data

(60) Provisional application No. 63/248,554, filed on Sep. 27, 2021, provisional application No. 63/167,747,
(Continued)

(51) Int. Cl.
*A61M 16/00* (2006.01)

(52) U.S. Cl.
CPC ..... *A61M 16/0066* (2013.01); *A61M 2205/42* (2013.01)

(58) Field of Classification Search
CPC ........ A41D 13/1153; A61B 2560/0443; A61B 2560/0462; A61B 2560/0475;
(Continued)

(56) References Cited

U.S. PATENT DOCUMENTS

| | | | |
|---|---|---|---|
| 4,782,832 A | 11/1988 | Trimble et al. |
| 4,944,310 A | 7/1990 | Sullivan |

(Continued)

FOREIGN PATENT DOCUMENTS

| | | | |
|---|---|---|---|
| AU | 2015200468 A1 | 2/2015 |
| CN | 101909414 A | 12/2010 |

(Continued)

OTHER PUBLICATIONS

Extended European Search Report mailed Aug. 2, 2024 in European Application No. 21887902.1, 9 pages.

(Continued)

*Primary Examiner* — Annette Dixon

(74) *Attorney, Agent, or Firm* — Nixon & Vanderhye P.C.

(57) ABSTRACT

A respiratory pressure therapy device includes an enclosure including a first portion and a second portion, the second portion configured to engage the first portion in an assembled configuration, a blower to provide a supply of air for respiratory pressure therapy, the blower enclosed at least partially in the enclosure, and a blower inlet muffler comprising a noise attenuating material, the noise attenuating material configured and arranged to face a blower inlet of the blower such that an axis of the blower inlet passes through a thickness of the noise attenuating material, wherein each of the first portion and the second portion of the enclosure supports and retains at least a portion of the noise attenuating material facing the blower inlet in the enclosure.

16 Claims, 61 Drawing Sheets

Related U.S. Application Data filed on Mar. 30, 2021, provisional application No. 63/108,946, filed on Nov. 3, 2020.

(58) Field of Classification Search

CPC ..... A61B 5/0245; A61B 5/14551; A61B 7/00; A61M 16/00; A61M 16/0003; A61M 16/0051; A61M 16/0057; A61M 16/0063; A61M 16/0066; A61M 16/0069; A61M 16/0078; A61M 16/021; A61M 16/022; A61M 16/024; A61M 16/06; A61M 16/0622; A61M 16/0633; A61M 16/0666; A61M 16/0683; A61M 16/0816; A61M 16/0858; A61M 16/0875; A61M 16/1005; A61M 16/105; A61M 16/107; A61M 16/1075; A61M 16/109; A61M 16/1095; A61M 16/125; A61M 16/16; A61M 16/161; A61M 16/162; A61M 16/20; A61M 16/208; A61M 2016/0027; A61M 2016/003; A61M 2016/0033; A61M 2016/0039; A61M 2016/0042; A61M 2202/0208; A61M 2205/02; A61M 2205/0216; A61M 2205/123; A61M 2205/14; A61M 2205/15; A61M 2205/18; A61M 2205/21; A61M 2205/276; A61M 2205/3303; A61M 2205/3306; A61M 2205/3317; A61M 2205/332; A61M 2205/3331; A61M 2205/3334; A61M 2205/3355; A61M 2205/3358; A61M 2205/3365; A61M 2205/3368; A61M 2205/3375; A61M 2205/3389; A61M 2205/3546; A61M 2205/3553; A61M 2205/3584; A61M 2205/3592; A61M 2205/36; A61M 2205/3653; A61M 2205/42; A61M 2205/50; A61M 2205/502; A61M 2205/505; A61M 2205/52; A61M 2205/581; A61M 2205/582; A61M 2205/583; A61M 2205/587; A61M 2205/6063; A61M 2205/75; A61M 2205/7545; A61M 2205/8206; A61M 2205/8212; A61M 2205/8237; A61M 2205/8262; A61M 2206/11; A61M 2206/16; A61M 2206/22; A61M 2207/00; A61M 2209/086; A61M 2209/088; A61M 2210/06; A61M 2210/0618; A61M 2210/0625; A61M 2210/083; A61M 2230/005; A61M 2230/46; A61M 2230/63; A62B 9/003; B01D 2253/108; B01D 2256/12; B01D 2257/102; B01D 2259/40005; B01D 2259/40007; B01D 2259/40009; B01D 2259/40081; B01D 2259/40086; B01D 2259/402; B01D 2259/4533; B01D 2259/4541; B01D 53/0407; B01D 53/0415; B01D 53/0438; B01D 53/047; B01F 2003/04872; B01F 2101/55; B01F 2215/0091; B01F 23/232; B01F 23/237611; B01F 3/0446; B29L 2031/753; F04D 17/08; F04D 17/16; F04D 25/0693; F04D 25/084; F04D 29/048; F04D 29/403; F04D 29/4206; F04D 29/4213; F04D 29/4226; F04D 29/602; F04D 29/663; F04D 29/664; F04D 29/665; F04D 29/667; F04D 29/701; F05B 2250/15; F05B 2250/25; F05D 2250/51; F05D 2260/96; G10K 11/04; G10K 11/161; Y10S 128/91; Y10T 29/49826

See application file for complete search history.

(56) References Cited

U.S. PATENT DOCUMENTS

| | | | | |
|---|---|---|---|---|
| 6,532,959 | B1 | 3/2003 | Berthon-Jones | |
| 6,581,594 | B1 | 6/2003 | Drew et al. | |
| 7,694,677 | B2 * | 4/2010 | Tang | A61M 16/107 128/204.18 |
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 10,695,522 | B2 | 6/2020 | Cariola et al. | |
| 2006/0237005 | A1 | 10/2006 | Virr et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2014/0352695 | A1 | 12/2014 | Friberg et al. | |
| 2015/0306332 | A1 | 10/2015 | Bafile et al. | |
| 2016/0114122 | A1 | 4/2016 | Crumblin et al. | |
| 2016/0310691 | A1 | 10/2016 | Bath et al. | |
| 2017/0082116 | A1 | 3/2017 | Nibu et al. | |
| 2017/0182270 | A1 | 6/2017 | Kenyon et al. | |
| 2018/0369521 | A1 | 12/2018 | Velzy et al. | |
| 2019/0175851 | A1 | 6/2019 | Barlow et al. | |
| 2019/0366025 | A1 | 12/2019 | Diehl et al. | |
| 2021/0001069 | A1 | 1/2021 | Higashiyama et al. | |
| 2022/0016377 | A1 | 1/2022 | Maeda et al. | |

FOREIGN PATENT DOCUMENTS

| | | | |
|---|---|---|---|
| CN | 204697052 | U | 10/2015 |
| CN | 107847701 | A | 3/2018 |
| JP | 2013-150684 | A | 8/2013 |
| JP | 2014-50519 | A | 3/2014 |
| JP | 2015-33522 | A | 2/2015 |
| JP | 2016-34410 | A | 3/2016 |
| JP | 2019-24622 | A | 2/2019 |
| WO | WO 98/004310 | A1 | 2/1998 |
| WO | WO 98/034665 | A1 | 8/1998 |
| WO | WO 2000/078381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | WO 2009/052560 | A1 | 4/2009 |
| WO | WO 2010/135785 | A1 | 12/2010 |
| WO | WO 2012/171072 | A1 | 12/2012 |
| WO | WO 2013/020167 | A1 | 2/2013 |
| WO | WO 2013/133889 | A1 | 9/2013 |
| WO | WO 2014/145869 | A1 | 9/2014 |
| WO | WO 2014/145869 | A9 | 9/2014 |
| WO | WO 2015/019574 | A1 | 2/2015 |
| WO | WO 2015/089582 | A1 | 6/2015 |
| WO | WO 2017/006189 | A1 | 1/2017 |
| WO | WO 2017/064975 | A1 | 4/2017 |
| WO | WO 2019/189126 | A1 | 10/2019 |
| WO | WO 2020/121255 | A1 | 6/2020 |
| WO | WO 2020/212902 | A1 | 10/2020 |
| WO | WO 2020/217843 | A1 | 10/2020 |

OTHER PUBLICATIONS

"*Respiratory Physiology*", by John B. West, Lippincott Williams & Wilkins, 9th edition published 2012 (8 pages).

International Search Report mailed Feb. 15, 2022 in International Application No. PCT/AU2021/051291, 28 pages.

Written Opinion of the International Searching Authority mailed Feb. 15, 2022 in International Application No. PCT/AU2021/051291, 11 pages.

International Preliminary Report on Patentability mailed Feb. 15, 2023 in International Application No. PCT/AU2021/051291, 47 pages.

(56) References Cited

OTHER PUBLICATIONS

Written Opinion of the International Searching Authority mailed Oct. 26, 2022 in International Application No. PCT/AU2021/051291, 15 pages.
First Office Action mailed Jan. 1, 2026 in Chinese Application No. 202180087461.5, with English translation, 18 pages.
Extended European Search Report mailed Jun. 8, 2026 in European Application No. 25225956.9, 10 pages.

* cited by examiner

RESPIRATORY PRESSURE THERAPY DEVICE

1 CROSS-REFERENCE TO RELATED APPLICATIONS

This application is the U.S. national phase of International Application No. PCT/AU2021/051291 filed Nov. 2, 2021, which designated the U.S. and claims the benefit of U.S. Provisional Application Nos. 63/108,946, filed Nov. 3, 2020, 63/167,747, filed Mar. 30, 2021, and 63/248,554, filed Sep. 27, 2021, each of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

A range of therapies have been used to treat or ameliorate such conditions. Furthermore, otherwise healthy individuals may take advantage of such therapies to prevent respiratory disorders from arising. However, at least some of these therapies and/or their implementations may have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, noisy, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired CO2 from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH2O relative to ambient pressure. For other forms of therapy, such as the delivery of oxygen, the patient interface may not include a seal sufficient to facilitate delivery to the airways of a supply of gas at a positive pressure of about 10 cmH2O. For flow therapies such as nasal HFT, the patient interface is configured to insufflate the nares but specifically to avoid a complete seal. One example of such a patient interface is a nasal cannula.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, general air pressure generators or ventilation systems may not be able to provide clinically beneficial respiratory therapy. Additionally, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise. If a device is too noisy, a patient may not comply with therapy.

Table of noise output levels of prior RPT devices (one specimen only, measured using test method specified in ISO 3744 in CPAP mode at 10 cmH2O).

| RPT Device name | A-weighted sound pressure level dB(A) | Year (approx.) |
|---|---|---|
| C-Series TangoTM | 31.9 | 2007 |
| C-Series TangoTM with Humidifier | 33.1 | 2007 |
| S8 EscapeTM II | 30.5 | 2005 |
| S8 EscapeTM II with H4iTM Humidifier | 31.1 | 2005 |
| S9 AutoSetTM | 26.5 | 2010 |
| S9 AutoSetTM with H5i Humidifier | 28.6 | 2010 |

The above values can be contrasted with some reference sound pressure values:

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisde™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of an RPT device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

For example, if an RPT device is large, it may be difficult or inconvenient for a patient to comply with therapy in a home setting, or while travelling. One known portable RPT device suitable for traveling is ResMed's AirMini CPAP device.

When RPT devices are used while the patient is asleep, the noise generated by the devices needs to be minimised. One challenge with that is that, because of the reduced size, standard noise-mitigating techniques, such as large muffling chambers and/or cavities full of volume of dampening material, have a limited application in portable RPT devices.

Thus, one of the challenges of making portable RPT devices for use in sleep therapy, is to make the device both small and quiet.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person or while traveling.

An aspect of the present technology relates to a CPAP system including an RPT device structured to produce a flow of air at positive pressure, a patient interface, and an air delivery tube to deliver pressurized air to the patient interface.

An aspect of the present technology relates to an RPT device structured and arranged to reduce noise output, e.g., while maintaining a relatively small size and yet still able to provide a wide range of therapy pressures. Such an RPT may be suitable for use in multiple environments, e.g., at home, in a hospital, and/or while traveling (train, bus, automobile, airplane, etc.).

An aspect of the present technology relates to an RPT device having an enclosure formed in at least two parts constructed and arranged to minimise noise passing through and/or between the at least two parts.

In certain forms of the present technology there is provided an RPT device having an enclosure formed in at least two parts having a seal therebetween. In some cases, the seal can be in the form of a gasket and/or a sealing bead.

In certain forms of the present technology there is provided an RPT device having an enclosure formed in at least two parts and comprising an enclosure wall constrainment arrangement.

In certain forms of the present technology there is provided an RPT device having an enclosure formed in at least two parts and having respective walls, wherein the respective walls are constructed and arranged to limit or reduce relative movement of the walls, e.g., to prevent inward flexure or deflection of a wall.

In certain forms of the present technology there is provided a pneumatic enclosure constructed from a least two parts, with a compression seal between the at least two parts, and wherein the walls of the enclosure are constrained against lateral movement at the junction between the at least two parts, thus reducing the noise escaping through the compression seal.

One aspect of the present technology is a sealing arrangement comprising a seal, e.g., a gasket, and a channel. The seal, e.g., gasket, is constructed and arranged to have a width less than the width of the channel when the seal, e.g., gasket, is not in compression. When the seal, e.g., gasket, is in compression, its width increases. The increased width may effect a seal with one or both side walls of the channel.

An aspect of the present technology relates to an RPT device including an enclosure that at least partially encloses various components of the RPT device, and a noise mitigating arrangement configured and arranged to reduce noise that is radiated by and/or transmitted through the joint or interface between a first portion and a second portion of the enclosure when in an assembled configuration. In an example, the noise mitigating arrangement comprises a wall constrainment arrangement to constrain lateral movement of the first portion and the second portion. In an example, the noise mitigating arrangement comprises a seal, e.g., a gasket, to provide a compression seal between the first portion and the second portion. In an example, the first and the second portions are respective parts of a tongue-and-groove arrangement. In a further example, the seal, e.g., gasket, may comprise a sealing bead arranged so that, in use, it is compressed between respective face surfaces of the tongue and groove arrangement (e.g., the first and the second portion). In this case, the compression seal is formed at least between horizontally (with respect to the operational configuration of the device) facing surfaces of the first and second portions and the seal, e.g., gasket, whilst the containment arrangement is defined by vertical side-orientated (inner and outer) surfaces (again with respect to the operational configuration of the device) of the first portion and the second portion. The interface between the sealing surfaces may extend in one or more planes that may not necessarily be horizontal and may extend under various angle/s with respect to a horizontal plane defined relative to the operational orientation of the device.

An aspect of the present technology relates to a RPT device including a blower to provide a supply of air for respiratory pressure therapy, a user interface, an air inlet, a suspension system arranged to suspend the blower, a seal, e.g., a gasket, a constrainment arrangement, and an enclosure to enclose the blower and the blower suspension system and to form a chamber. The enclosure includes a first portion and a second portion. The first portion of the enclosure includes a first interior surface, a first exterior surface and a first intermediate surface located between the first interior surface and the first exterior surface. The second portion of the enclosure includes a second interior surface, a second exterior surface and a second intermediate surface located between the second interior surface and the second exterior surface. The user interface is mounted on the first exterior surface. The seal, e.g., gasket, is arranged to be in compression between the first intermediate surface and the second intermediate surface in use. The constrainment arrangement is configured to limit lateral movement of the first portion and the second portion.

An aspect of the present technology relates to a noise mitigating arrangement for a housing enclosing at least a blower, e.g., of an RPT device, the housing comprising at least first and a second housing portions, each of the housing portions having a peripheral edge and being arranged to engage with the other of the housing portions along the peripheral edge, wherein, in an assembled configuration, a lateral movement of the engaged peripheral edge of each housing portion is constrained on both sides along at least a portion of the peripheral edge.

One aspect of the present technology relates to an enclosure formed in at least two parts movable relative to one another. The enclosure may include one or more parts to reduce the transmission of conducted and/or radiated noise between the two parts, and/or through the two parts. The componentry may include a seal, e.g., gasket, or a seal arrangement formed as part of or between the two parts of the enclosure, e.g., located at an interface or joint between the two parts. Moreover, the two parts may be constrained or limited in lateral movement, e.g., due to the seal, e.g., gasket, or seal arrangement, and/or one or more structural features of the first and/or second one of the two parts, e.g., a channel and a tongue. The enclosure may be a pneumatic enclosure, as at least a portion of an interior of the enclosure may be at a pressure that is different than ambient pressure on the outside of the enclosure, and the seal, e.g., gasket, or seal arrangement may serve to prevent, or at least reduce, air or gas surrounding or contained within the enclosure from flowing (e.g., via a joint or interface between the two parts) from the high pressure side to the low pressure side (i.e., from the outside to the inside of the enclosure, and/or from the inside to the outside of the enclosure). In some cases, where the enclosure is part of an RPT device, at least a portion of the interior of the enclosure may be exposed to a pressure that may be negative. The high pressure at the blower outlet may in this case be confined to a dedicated pneumatic housing inside the main enclosure. Depending on whether the high pressure is passed on directly to the enclosure outlet or not, it may or may not interact with an inner wall of the enclosure. The enclosure may include supporting structure to support one or more other parts, such as an internal part, e.g., a blower, or one or more muffler components, etc.

An aspect of one form of the present technology relates to an apparatus for providing positive pressure respiratory therapy to a patient breathing in a respiratory cycle including an inhalation portion and an exhalation portion. The apparatus includes: a controllable motor-blower configured to generate a supply of air at a positive pressure relative to ambient pressure by rotating one or more impellers at an impeller speed; a housing holding the motor-blower, the housing comprising an inlet and a patient-connection port, the patient-connection port being structured to communicate the supply air at the positive pressure from the motor-blower to a patient interface via an air circuit in use; a sensor to monitor at least one of pressure and a flow rate of the supply of air at positive pressure and to generate a sensor output; and a controller configured to adjust an operating parameter of the motor-blower in accordance with the sensor output to maintain a minimum positive pressure in the patient interface during a treatment session by causing an increase in the impeller speed during the inhalation portion of the respiratory cycle and causing a decrease in the impeller speed during the exhalation portion of the breathing cycle.

Another aspect of the present technology relates to an RPT device including at least one muffler structured and arranged to reduce noise output of the RPT device in use.

Another aspect of the present technology relates to an RPT device including a muffling system comprising one or more mufflers structured and arranged to reduce noise output of the RPT device in use. In an example, the muffling system may comprise one or more inlet mufflers arranged upstream of a blower inlet of the blower and/or one or more outlet mufflers arranged downstream of a blower outlet of the blower.

Another aspect of the present technology relates to an RPT device including a blower inlet muffler configured and arranged to reduce a noise output generated by the blower and emanating from the blower inlet of the blower in use.

Another aspect of the present technology relates to an RPT device including a blower inlet muffler configured and arranged to face a blower inlet of the blower.

Another aspect of one form of the present technology relates to a respiratory pressure therapy device including an enclosure including a first portion and a second portion, the second portion configured to engage the first portion in an assembled configuration, a blower to provide a supply of air for respiratory pressure therapy, the blower enclosed at least partially in the enclosure, and a blower inlet muffler comprising a noise attenuating material, the noise attenuating material configured and arranged to face a blower inlet of the blower such that an axis of the blower inlet passes through a thickness of the noise attenuating material. Each of the first portion and the second portion of the enclosure supports and retains at least a portion of the noise attenuating material in the enclosure.

Another aspect of one form of the present technology relates to a respiratory pressure therapy device including an enclosure, a blower to provide a supply of air for respiratory pressure therapy, the blower enclosed at least partially in the enclosure, and a blower inlet muffler comprising a rigidized wall portion configured and arranged to face a blower inlet of the blower. The rigidized wall portion supports and retains a noise attenuating material.

Another aspect of one form of the present technology relates to a respiratory pressure therapy device including an enclosure, a blower to provide a supply of air for respiratory pressure therapy, the blower enclosed at least partially in the enclosure, a plurality of flow tubes enclosed at least partially in the enclosure, the plurality of flow tubes arranged upstream of a blower inlet of the blower, and a blower inlet muffler comprising a noise attenuating material. The noise attenuating material is configured and arranged to face the blower inlet of the blower and an opening of at least one of the plurality of flow tubes.

Another aspect of the present technology relates to an RPT device including a blower outlet muffler configured and arranged to reduce a noise output generated by the blower and emanating from the blower outlet of the blower in use.

Another aspect of the present technology relates to an RPT device including a blower outlet muffler configured and arranged to face a blower outlet of the blower.

Another aspect of the present technology relates to an RPT device including an enclosure, a blower to provide a supply of air for respiratory pressure therapy, the blower enclosed at least partially in the enclosure, and a blower outlet muffler, wherein the blower outlet muffler is separate and discrete from the enclosure.

Another aspect of one form of the present technology relates to a respiratory pressure therapy device including an enclosure, a blower to provide a supply of air for respiratory pressure therapy, the blower enclosed at least partially in the enclosure, and a blower outlet muffler comprising a main body forming a blower outlet chamber located downstream of a blower outlet of the blower, wherein the main body and blower outlet chamber thereof is separate and discrete from the enclosure.

Another aspect of one form of the present technology relates to a respiratory pressure therapy device including an enclosure, a blower to provide a supply of air for respiratory pressure therapy, the blower enclosed at least partially in the enclosure, and a blower outlet muffler comprising a main body forming a blower outlet chamber located downstream of a blower outlet of the blower, wherein the main body and blower outlet chamber thereof is separate and discrete from the enclosure, wherein the blower outlet muffler further comprises a blower outlet end suspension provided to the main body, and the blower outlet end suspension resiliently supports the blower adjacent the blower outlet of the blower, and wherein the main body comprises a different material than the blower outlet end suspension.

Another aspect of the present technology relates to an RPT device including an enclosure, a blower to provide a supply of air for respiratory pressure therapy, the blower enclosed at least partially in the enclosure, and a blower outlet muffler, wherein the blower outlet muffler is at least partially integrated with the enclosure.

Another aspect of the present technology relates to a respiratory pressure therapy device including an enclosure forming at least a portion of a device inlet chamber and a blower outlet chamber and a blower to provide a supply of air for respiratory pressure therapy, the blower enclosed at least partially in the device inlet chamber, wherein the blower outlet chamber is located at a blower outlet of the blower, the blower outlet chamber including at least a portion of an inlet flow path along which air moves before entering the blower.

Another aspect of one form of the present technology relates to a respiratory pressure therapy device including an enclosure forming at least a portion of a device inlet chamber and a blower outlet chamber, a blower to provide a supply of air for respiratory pressure therapy, the blower enclosed at least partially in the device inlet chamber, a first plate assembly including a base plate and a blower outlet end suspension to support the blower adjacent a blower outlet of the blower, the base plate forming a wall of the device inlet chamber and the blower outlet chamber, and a second plate assembly including a base plate forming a wall of the at blower outlet chamber, the second plate assembly further comprising at least one inlet tube that allows air to enter the device inlet chamber and an outlet tube that allows air to exit the blower outlet chamber.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 6000 according to an example of the present technology. Air from the RPT device 6000 passes along an air circuit 4170 to the patient 1000. A bed partner 1100 is also shown. The patient is sleeping in a supine sleeping position.

4.2 Patient Interface

FIG. 2A shows a patient interface in the form of a nasal mask in accordance with one form of the present technology.

FIG. 2B shows a schematic of a cross-section through a structure at a point. An outward normal at the point is indicated. The curvature at the point has a positive sign, and a relatively large magnitude when compared to the magnitude of the curvature shown in FIG. 2C.

FIG. 2C shows a schematic of a cross-section through a structure at a point. An outward normal at the point is indicated. The curvature at the point has a positive sign, and a relatively small magnitude when compared to the magnitude of the curvature shown in FIG. 2B.

FIG. 2D shows a schematic of a cross-section through a structure at a point. An outward normal at the point is indicated. The curvature at the point has a value of zero.

FIG. 2E shows a schematic of a cross-section through a structure at a point. An outward normal at the point is indicated. The curvature at the point has a negative sign, and a relatively small magnitude when compared to the magnitude of the curvature shown in FIG. 2F.

FIG. 2F shows a schematic of a cross-section through a structure at a point. An outward normal at the point is indicated. The curvature at the point has a negative sign, and a relatively large magnitude when compared to the magnitude of the curvature shown in FIG. 2E.

4.3 RPT Device

FIG. 3A-2 is another perspective view of the RPT device of FIG. 3A-1.

FIG. 3B-1 is a perspective view showing size comparison between ResMed's AirSense 10 device and the RPT device of FIG. 3A-1 according to an example of the present technology.

FIG. 3B-2 is a side view showing size comparison between ResMed's AirSense 10 device and the RPT device of FIG. 3A-1 according to an example of the present technology.

FIG. 3B-3 is a perspective view showing the RPT device of FIG. 3A-1 held in a user's hand according to an example of the present technology.

FIG. 3B-4 is a perspective view showing the RPT device of FIG. 3A-1 on a tray table of an airplane according to an example of the present technology.

FIG. 3B-5 is another perspective view showing the RPT device of FIG. 3A-1 on a tray table of an airplane according to an example of the present technology.

FIG. 3N-1 is enlarged cross-sectional view showing of FIG. 3N. This view shows the theoretical interference between parts in phantom.

FIG. 3N-2 is an enlarged cross-sectional view similar to FIG. 3N-1 showing possible in-use shape of the seal, e.g., gasket, according to an example of the present technology.

FIG. 3N-3 is an enlarged cross-sectional view showing assembly of the upper and lower portions of the enclosure according to an example of the present technology.

FIG. 3N-4 is an enlarged cross-section showing possible shape of the groove and/or the groove wall, according to an example of the present technology.

FIG. 3R-1 is an enlarged cross-sectional view showing a portion of the enclosure of FIG. 3R.

Figure 4A:
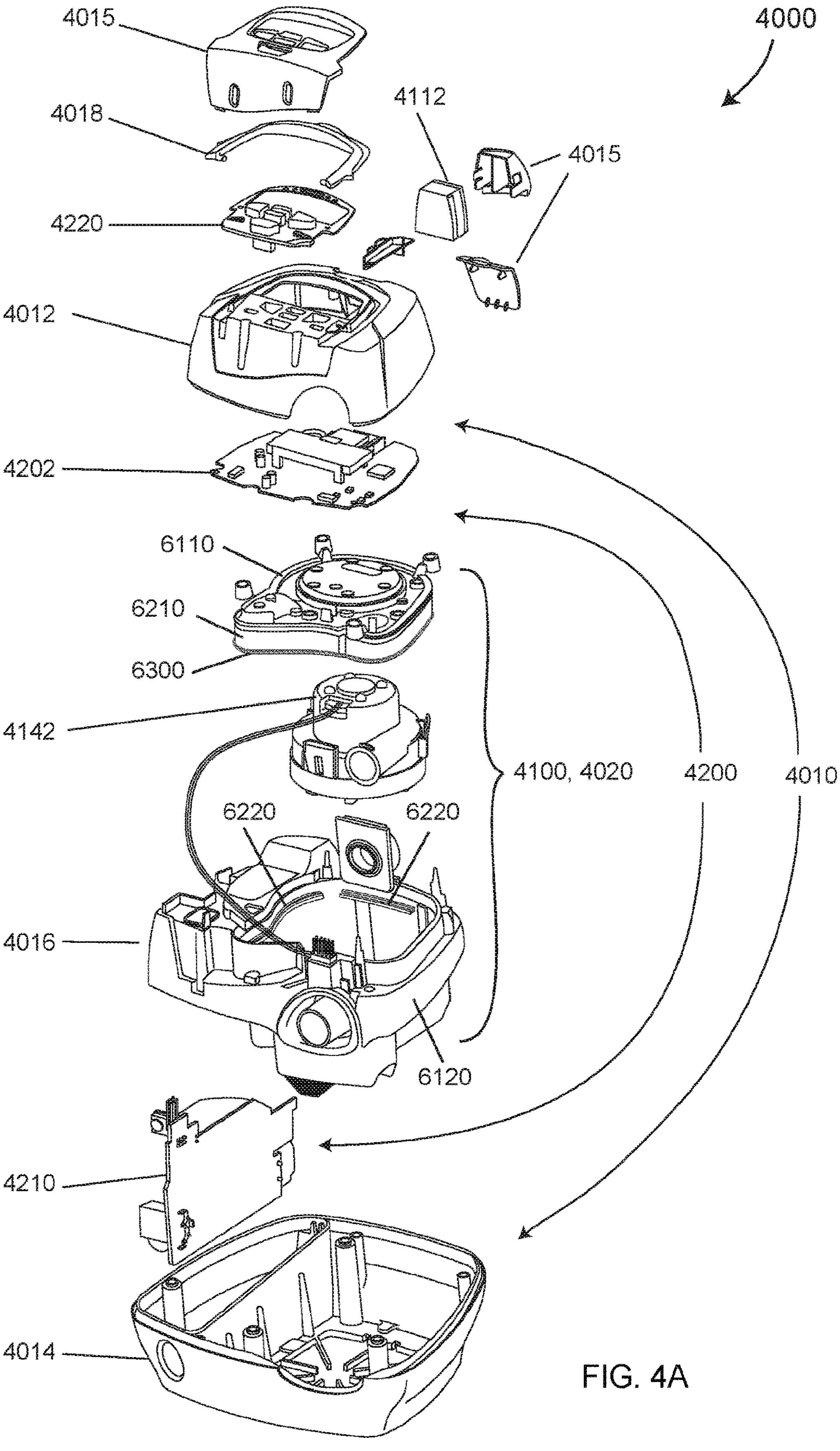
FIG. 4A shows an RPT device in accordance with one form of the present technology.
Figure 4B:
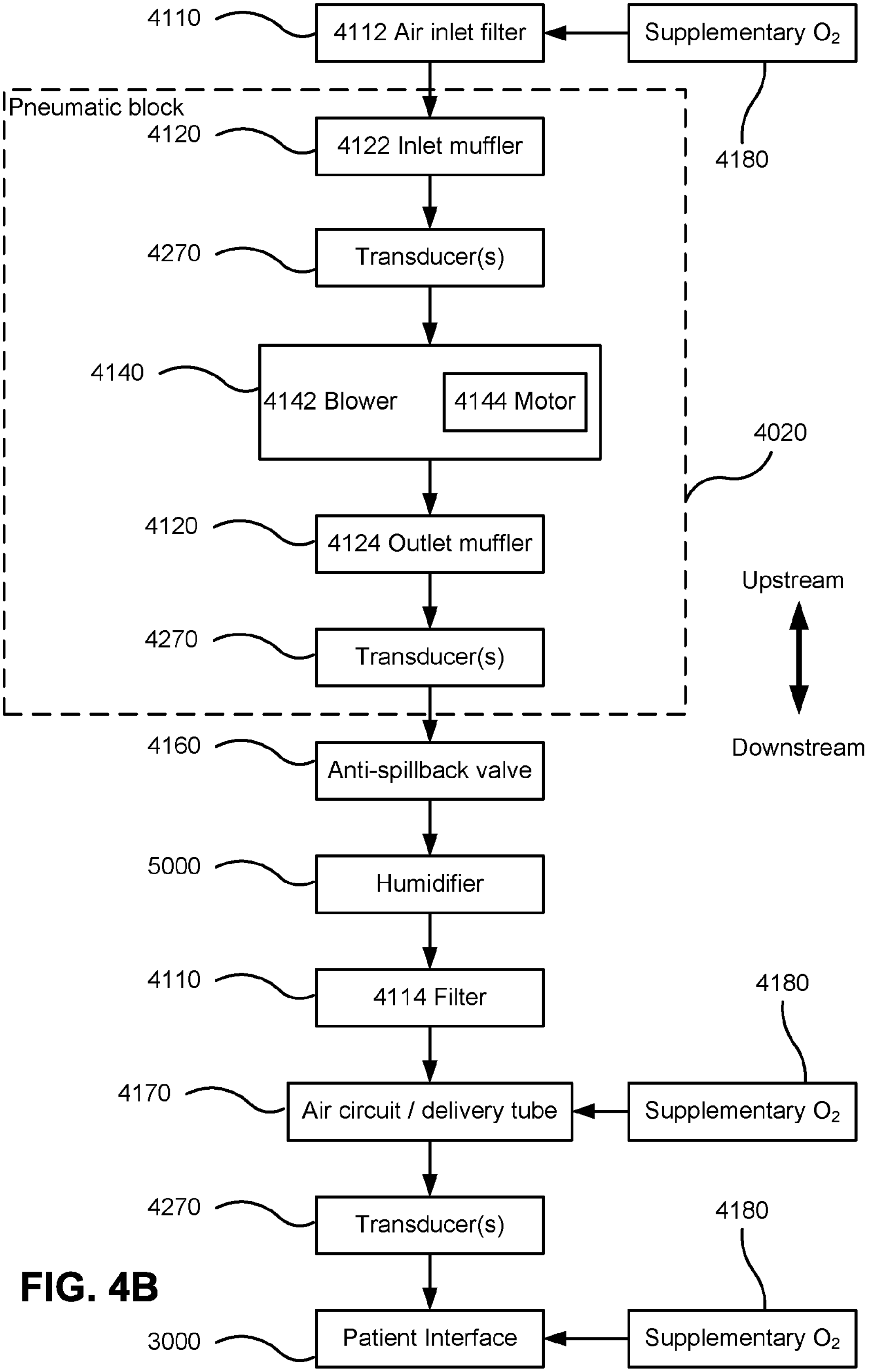

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
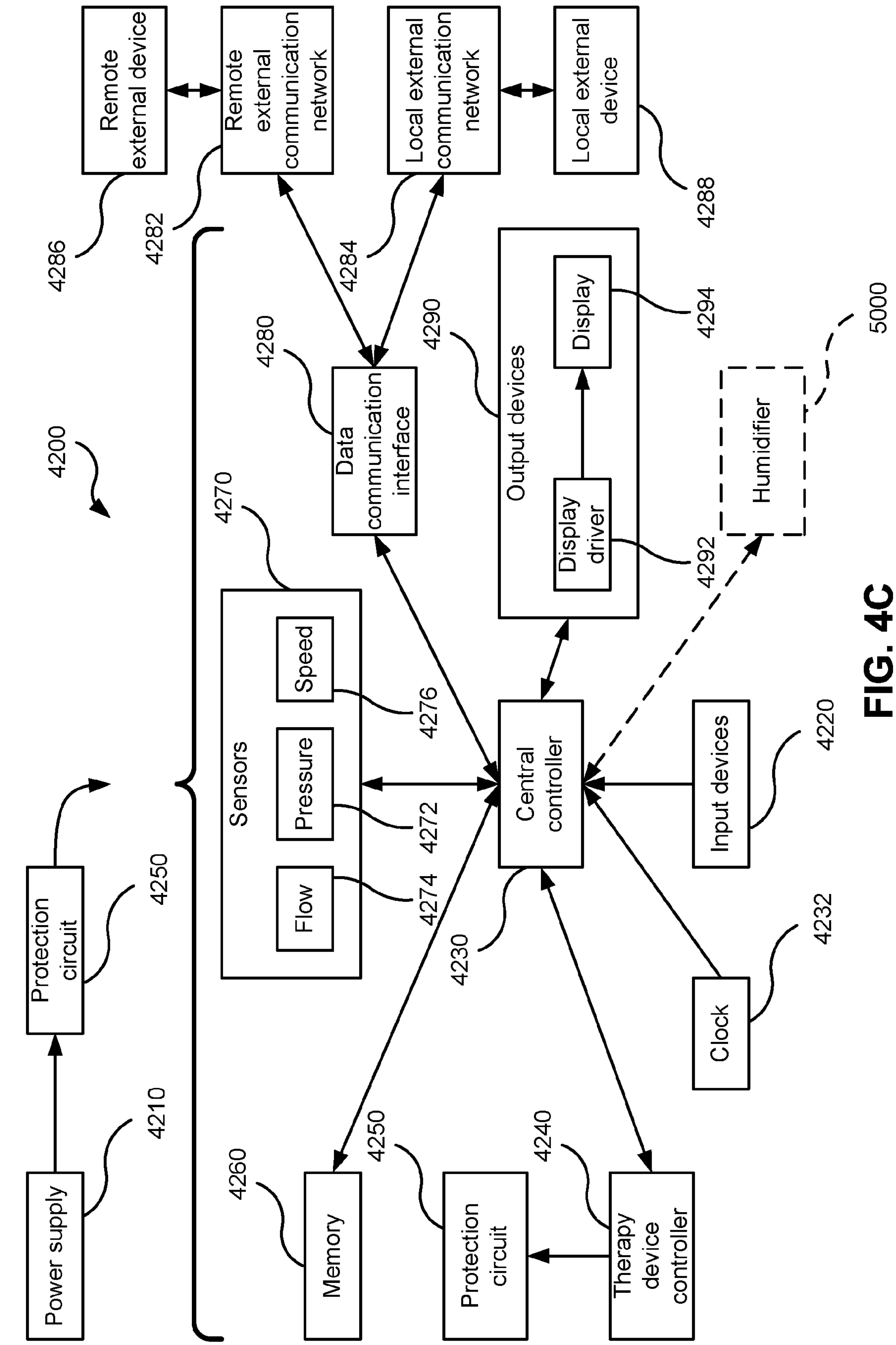

FIG. 4C is a schematic diagram of the electrical components of an RPT device in accordance with one form of the present technology.

Figure 4D:
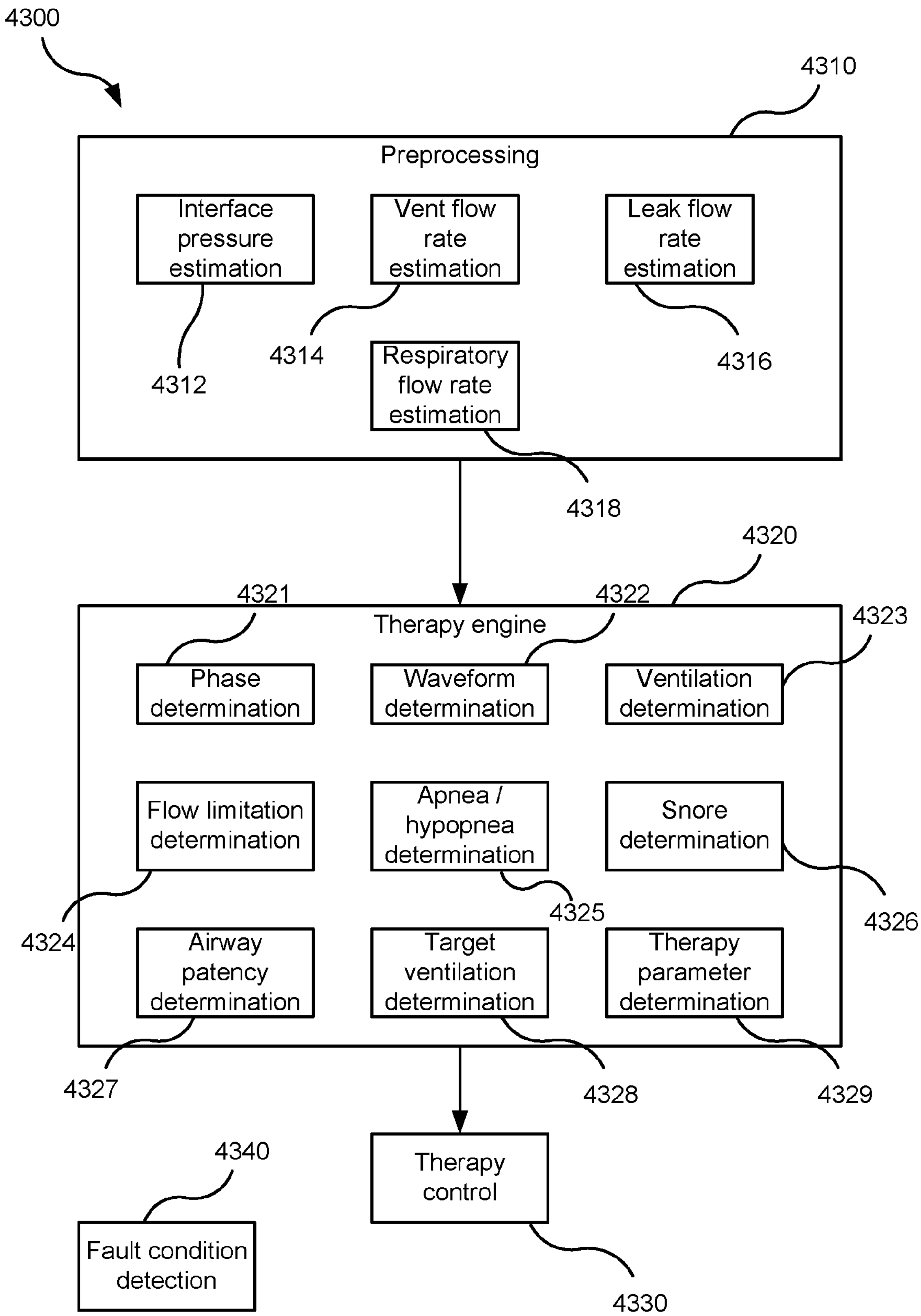

FIG. 4D is a schematic diagram of the algorithms implemented in an RPT device in accordance with one form of the present technology.

Figure 4E:
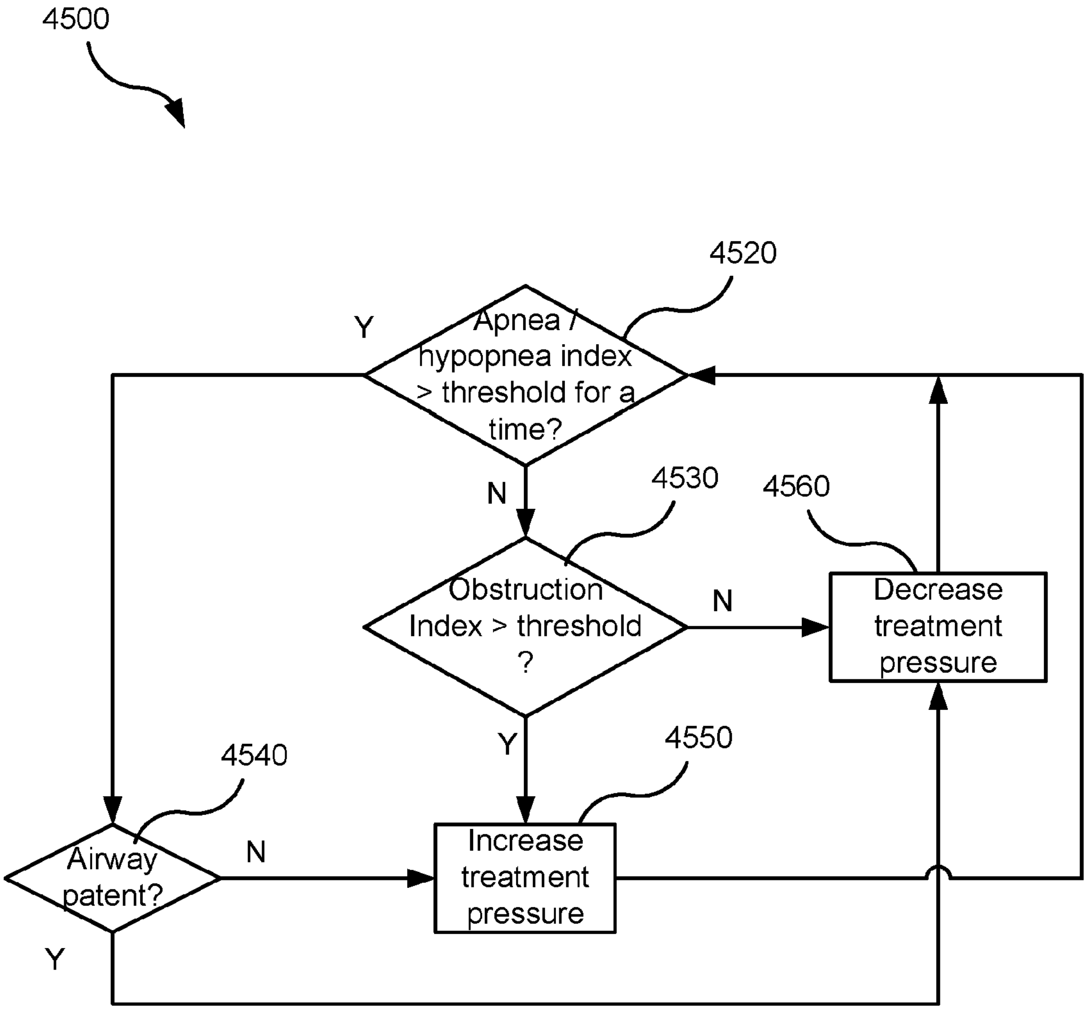

FIG. 4E is a flow chart illustrating a method carried out by the therapy engine module of FIG. 4D in accordance with one form of the present technology.

Figure 5A:
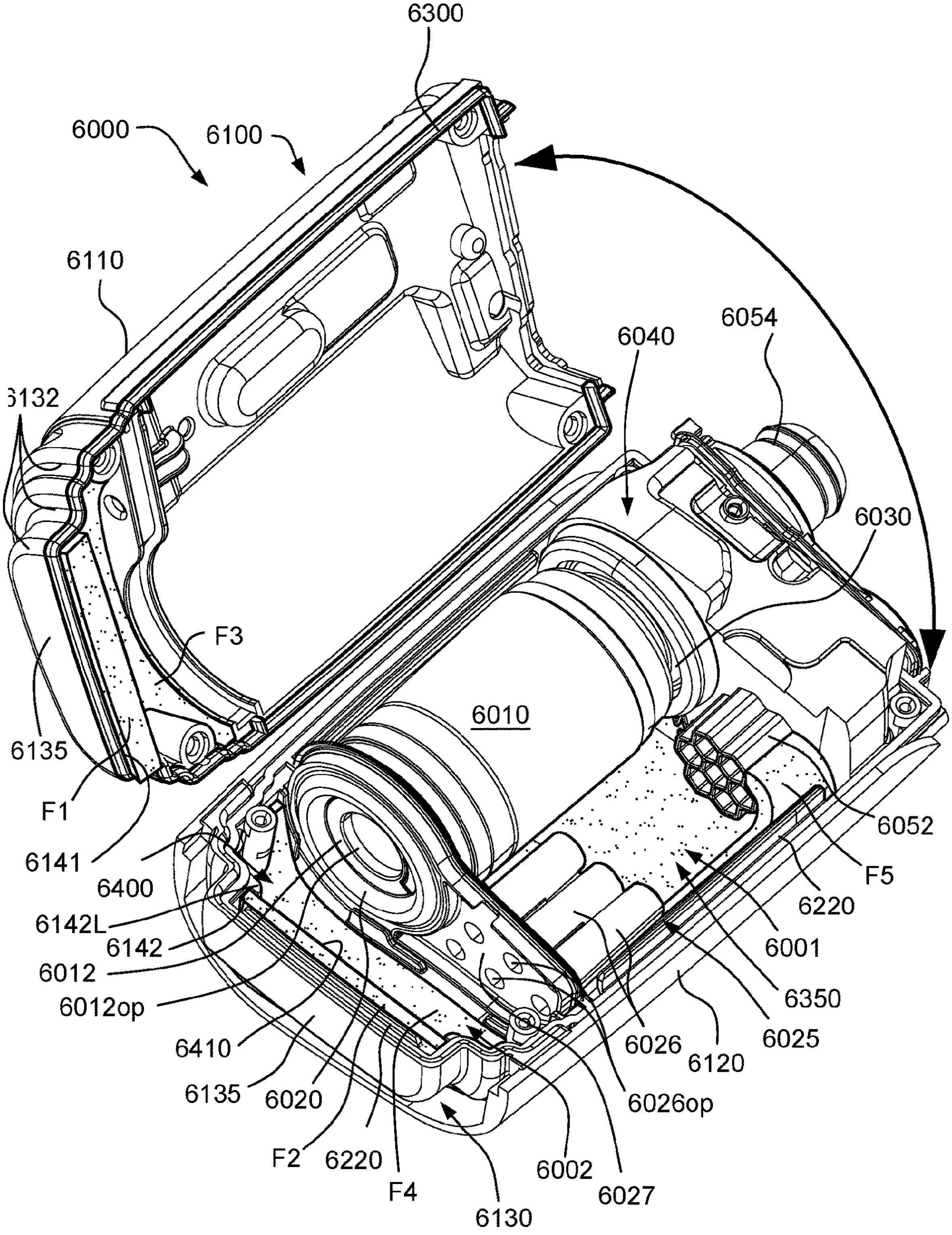

FIG. 5A is a perspective view showing an enclosure, internal components, and a muffling system of an RPT device, with an upper portion of the enclosure disassembled, according to an example of the present technology.

Figure 5C:
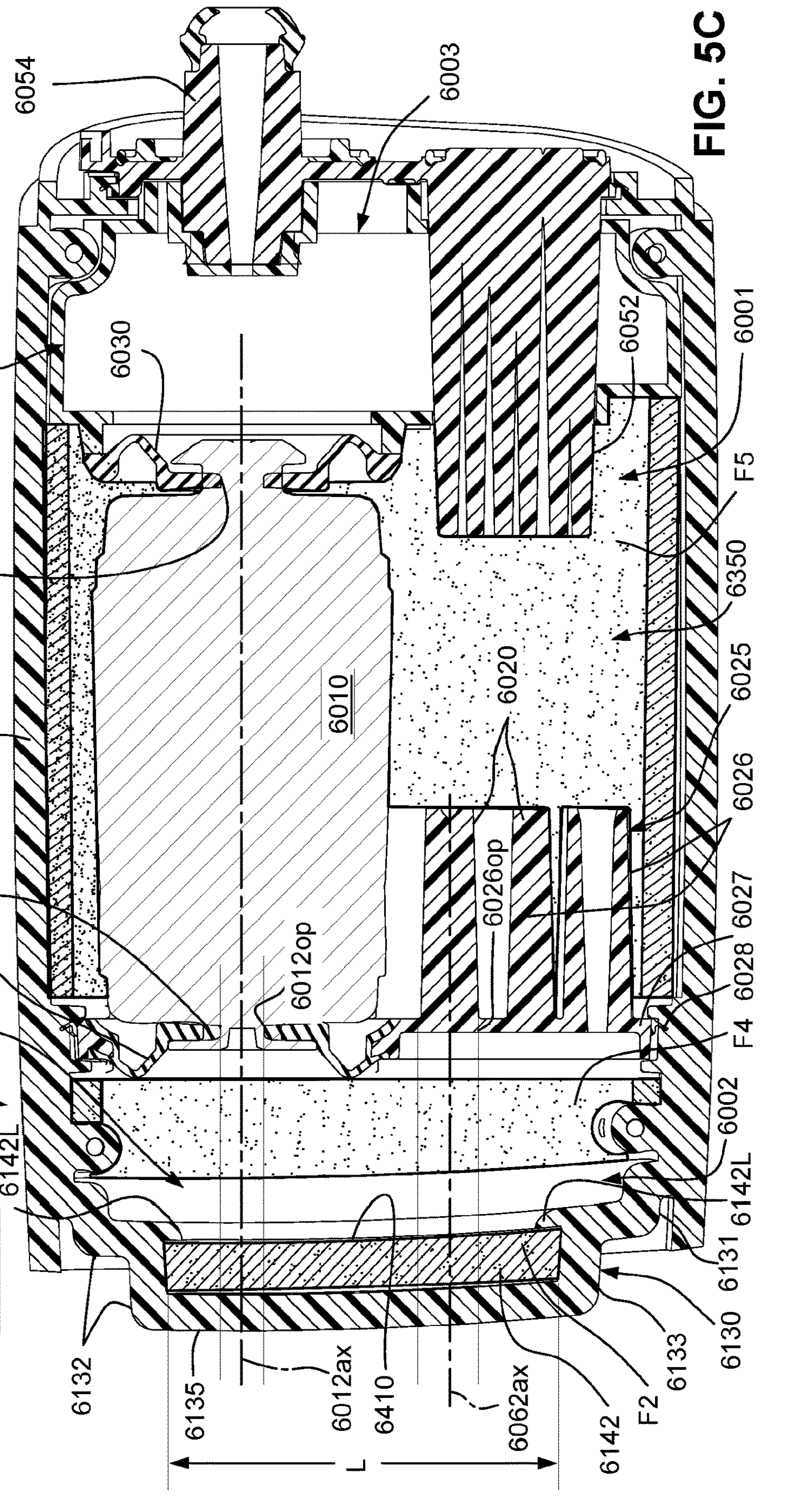
Figure 5B:
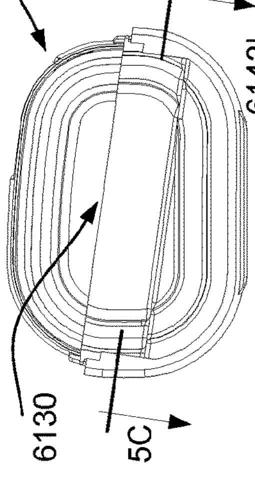

FIG. 5B is an end view of the enclosure of FIG. 5A in an assembled configuration according to an example of the present technology.

FIG. 5C is a cross-sectional view through line 5C-5C of FIG. 5B.

Figure 5D:
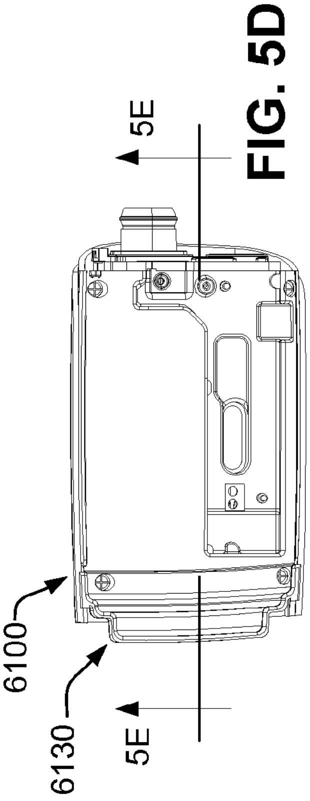

FIG. 5D is a top view of the enclosure of FIG. 5A in an assembled configuration according to an example of the present technology.

Figure 5E:
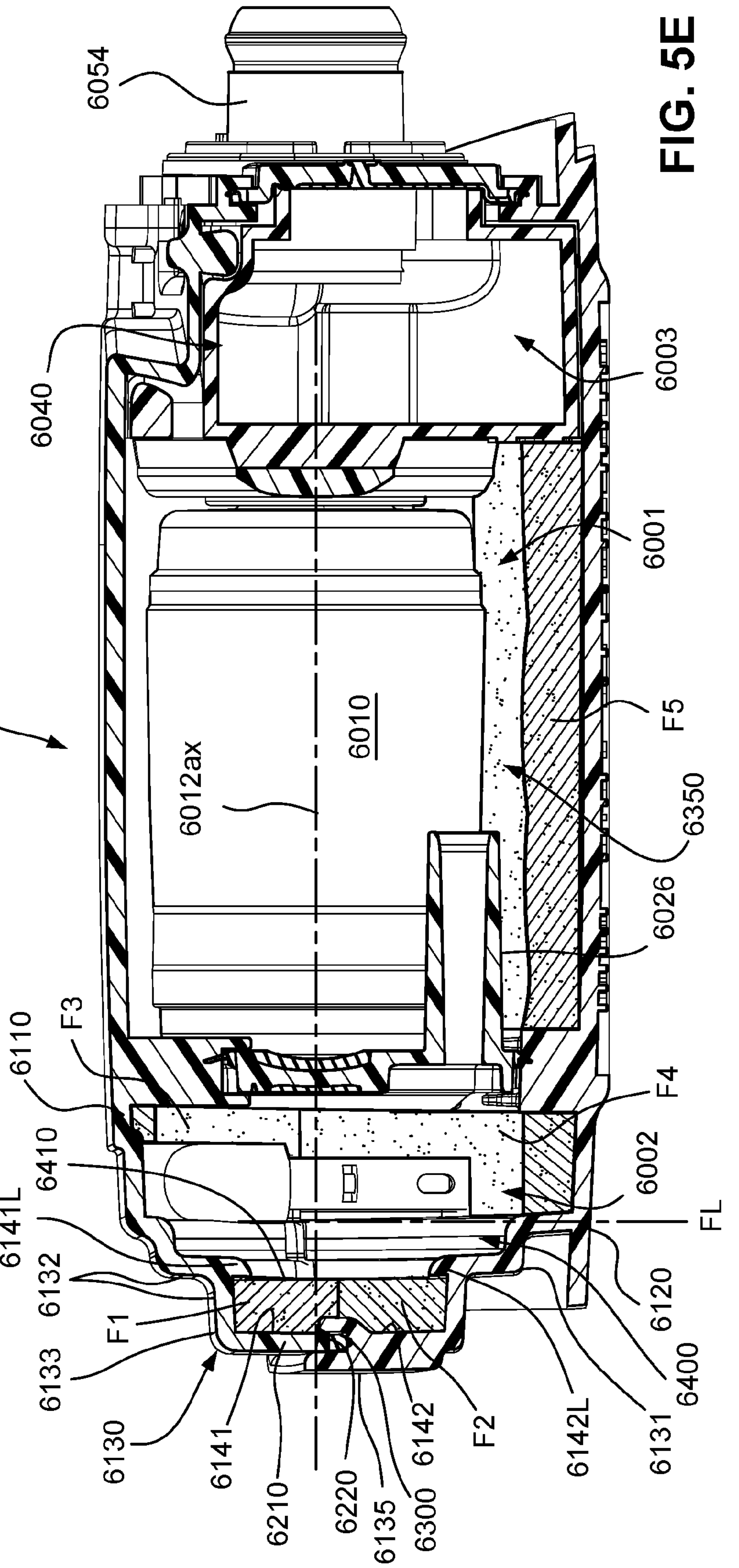

FIG. 5E is a cross-sectional view through line 5E-5E of FIG. 5D.

Figure 5G:
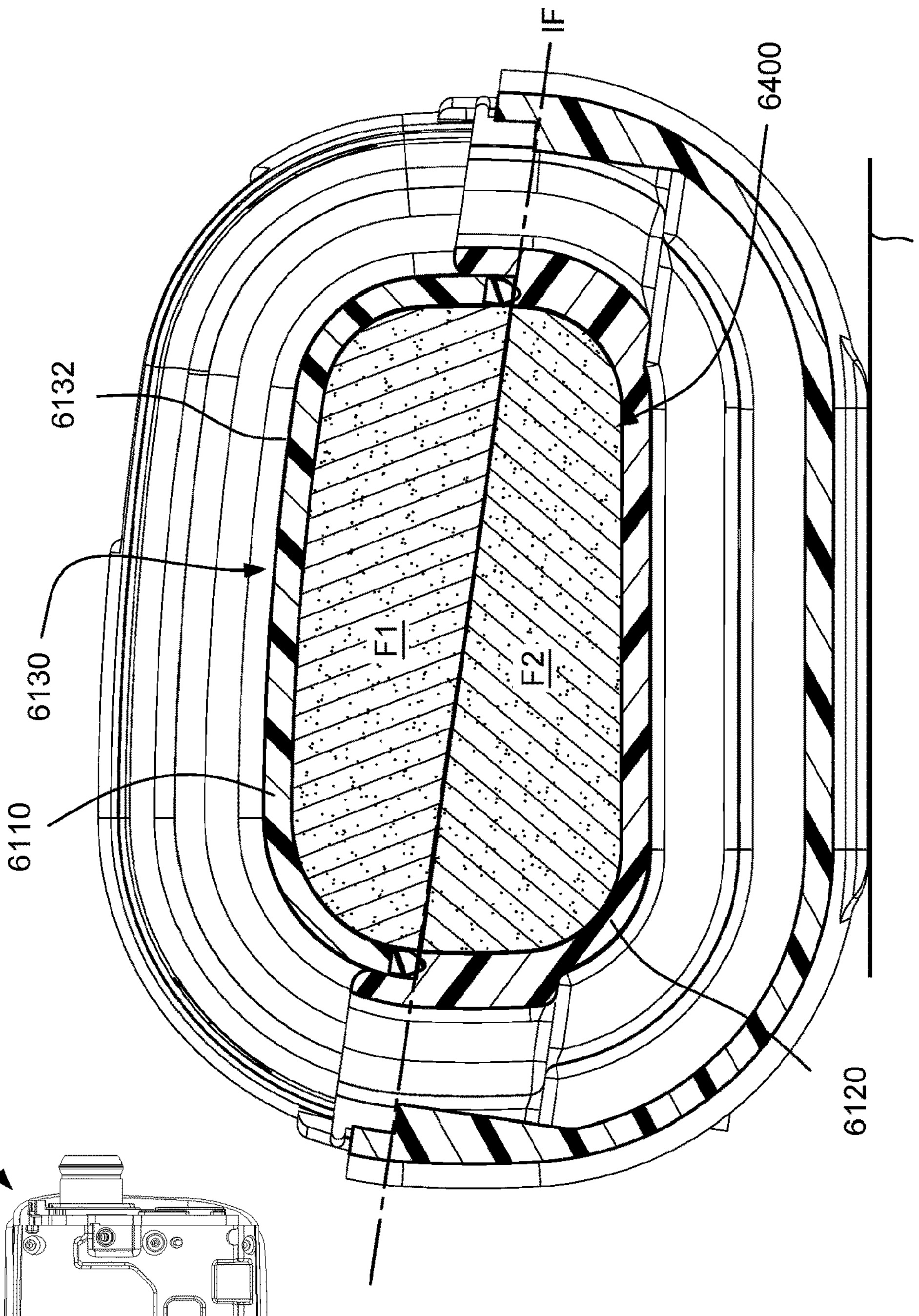
Figure 5F:
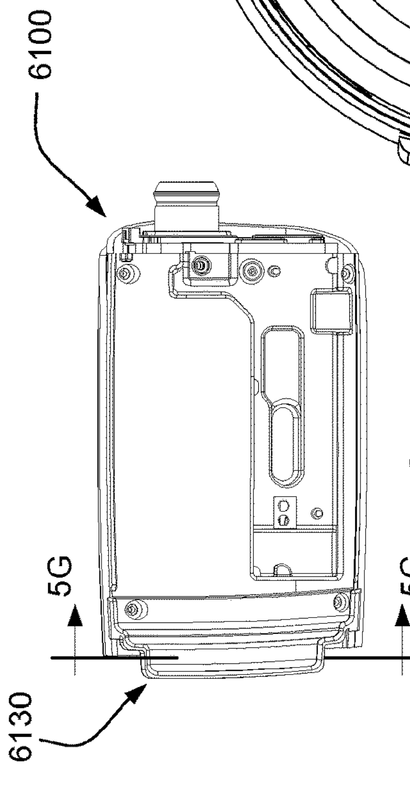

FIG. 5F is a top view of the enclosure of FIG. 5A in an assembled configuration according to an example of the present technology.

FIG. 5G is a cross-sectional view through line 5G-5G of FIG. 5F.

Figure 5I:
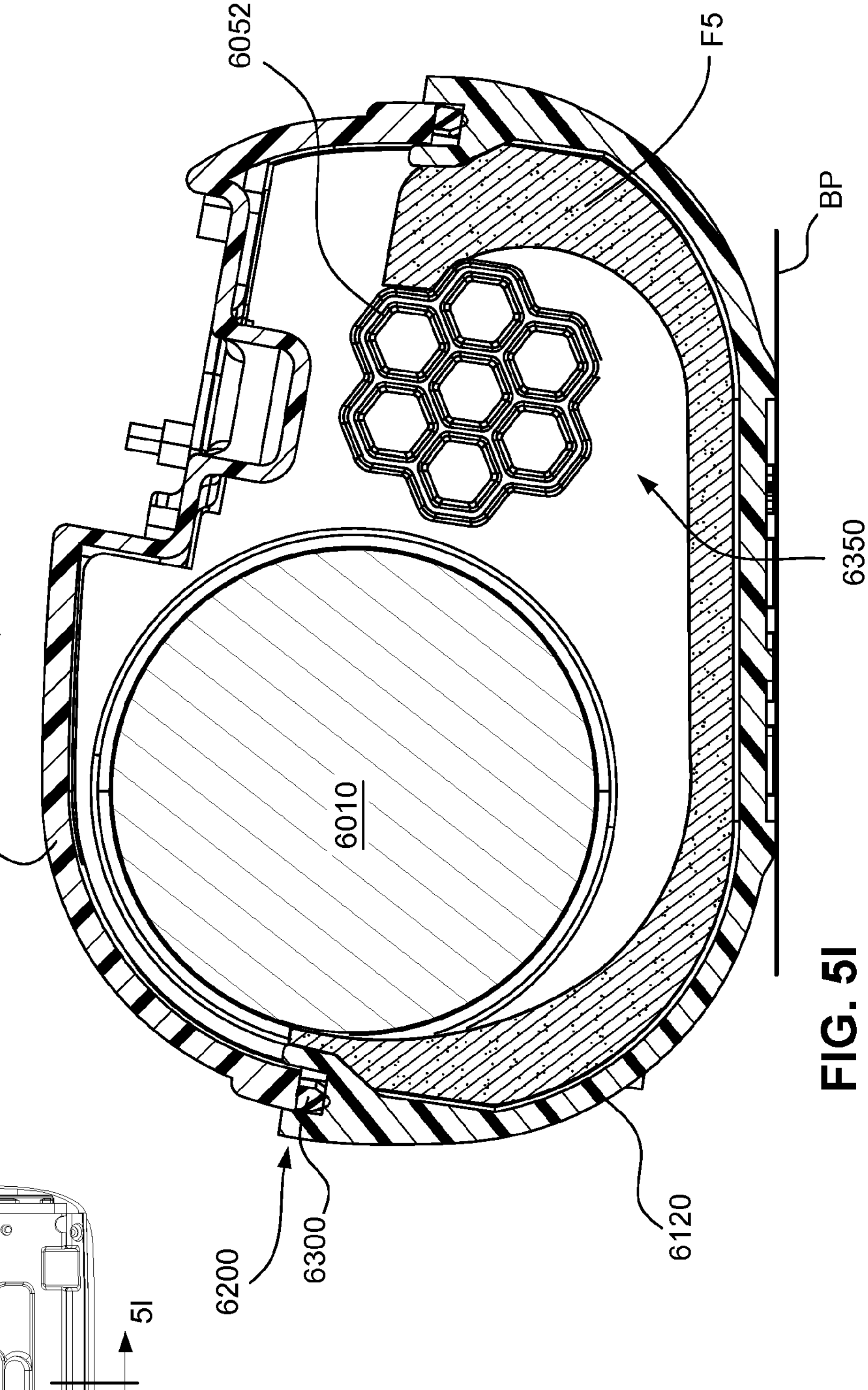
Figure 5H:
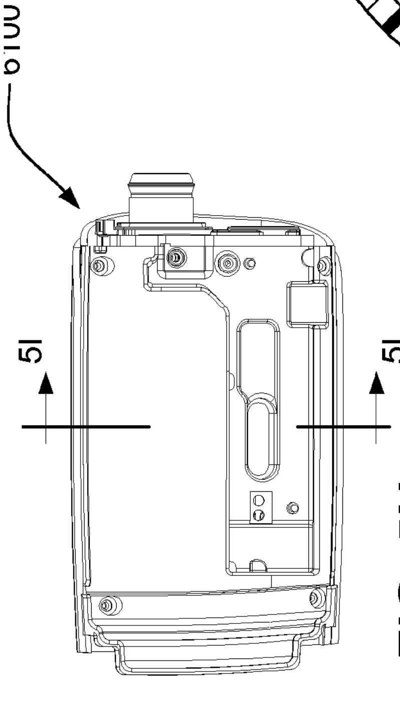

FIG. 5H is a top view of the enclosure of FIG. 5A in an assembled configuration according to an example of the present technology.

FIG. 5I is a cross-sectional view through line 5I-5I of FIG. 5H.

Figure 5K:
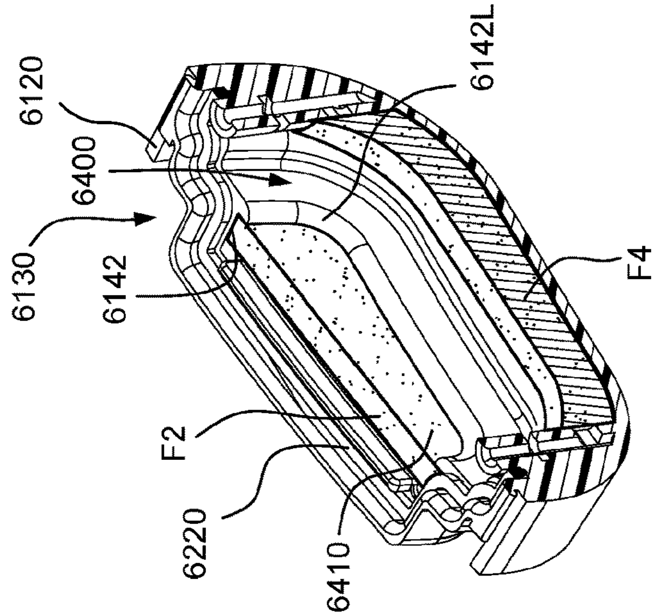
Figure 5J:
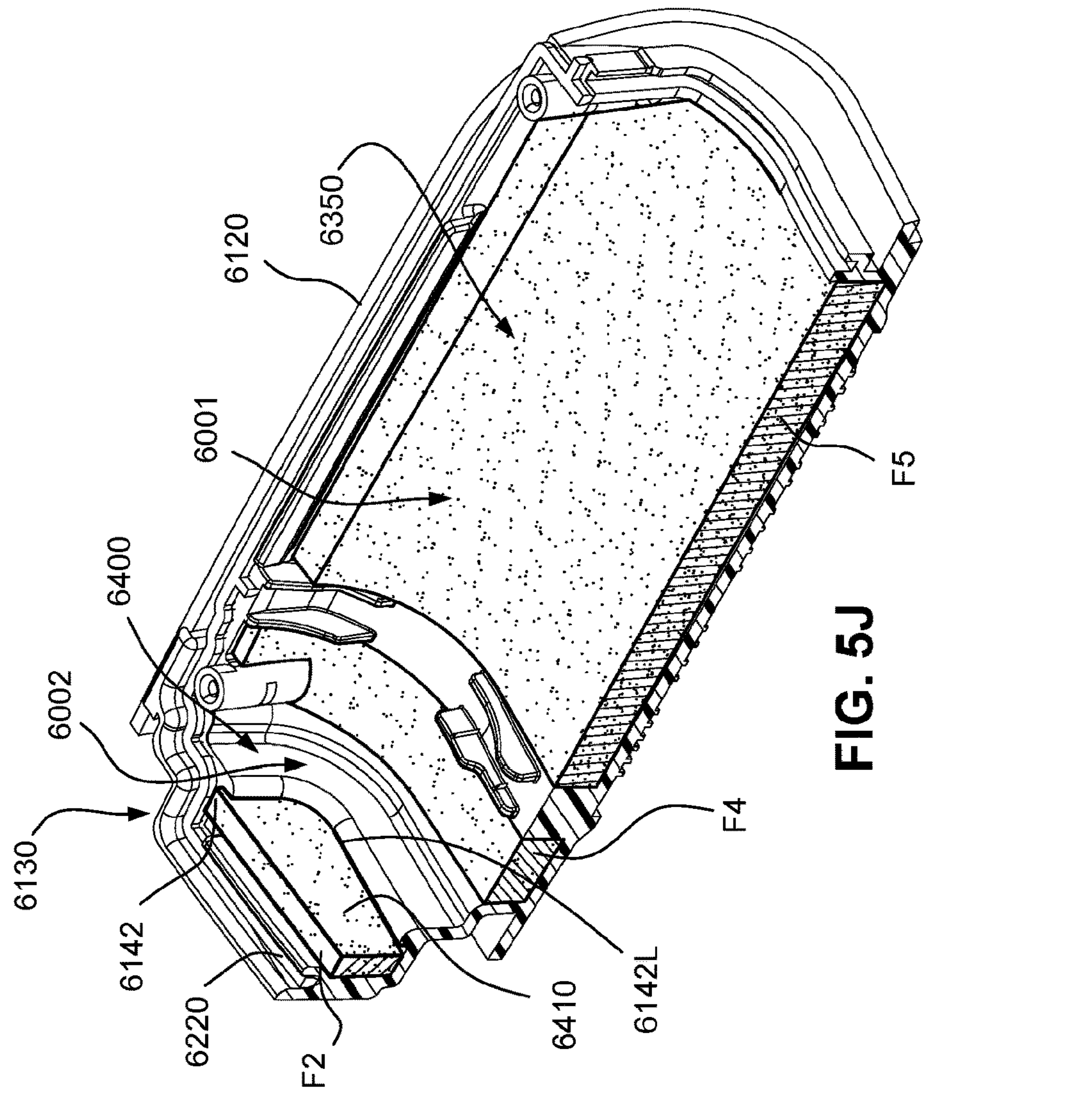

FIG. 5J is a cross-sectional view showing a lower portion of the enclosure and muffling system of FIG. 5A with internal components disassembled according to an example of the present technology.

FIG. 5K is another cross-sectional view showing a lower portion of the enclosure and muffling system of FIG. 5A with internal components disassembled according to an example of the present technology.

Figure 6B:
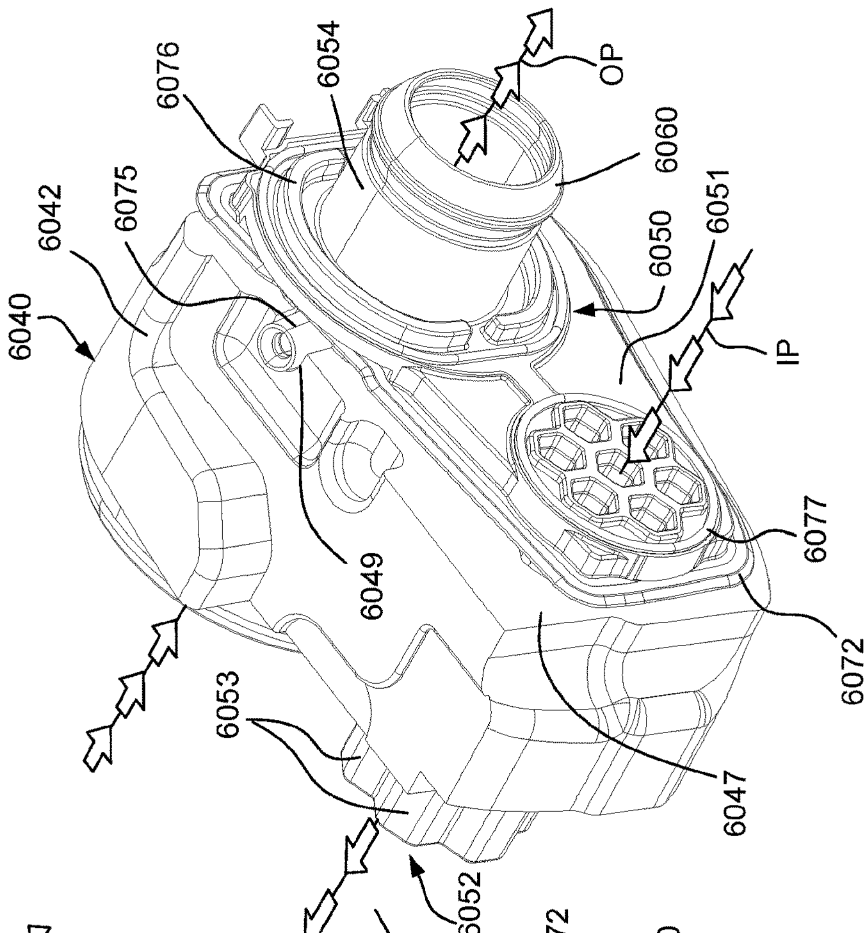
Figure 6A:
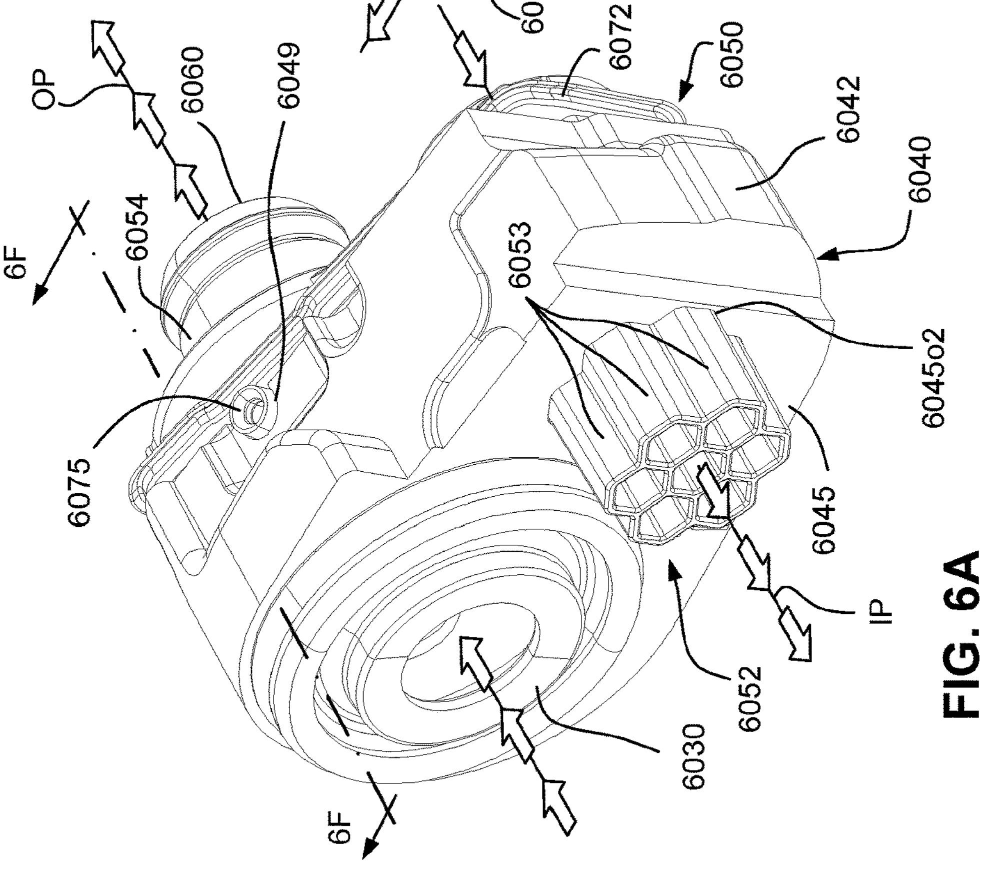

FIG. 6A is a perspective view showing a sub-assembly of an inlet/outlet assembly and a main body of a blower outlet muffler according to an example of the present technology.

FIG. 6B is another perspective view of the sub-assembly shown in FIG. 6A.

Figure 6C:
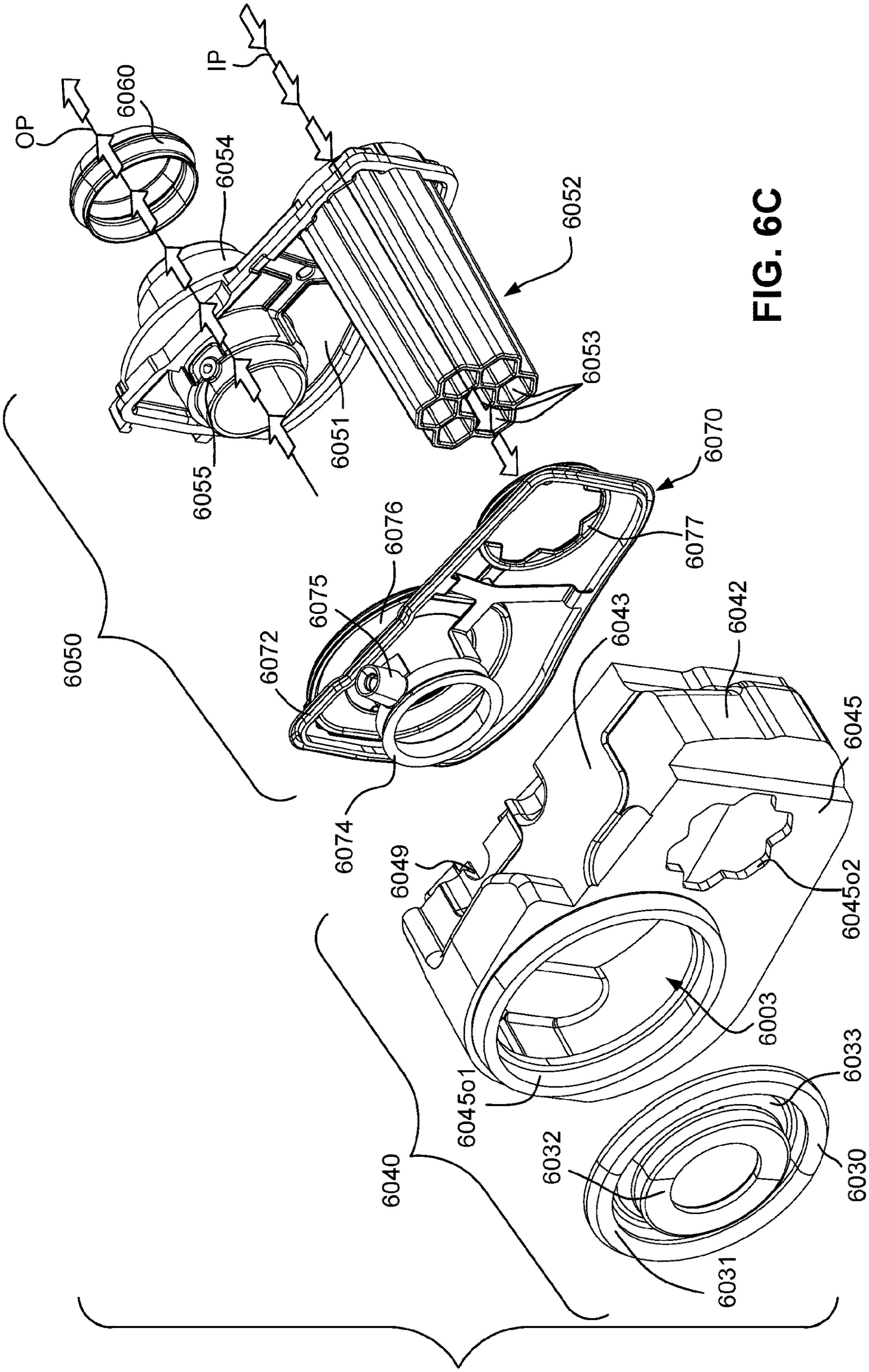

FIG. 6C is an exploded view of the sub-assembly shown in FIG. 6A.

Figure 6D:
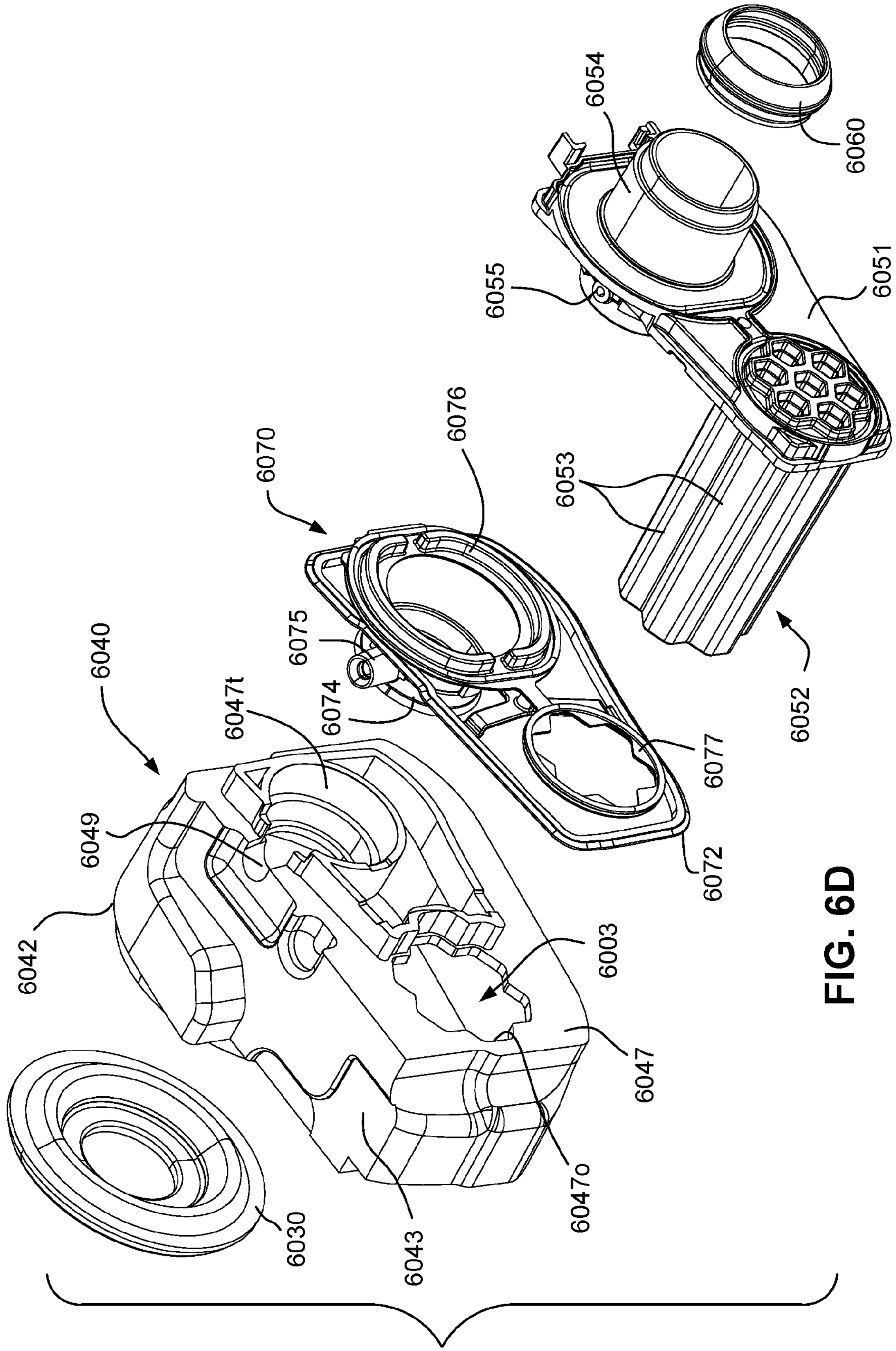

FIG. 6D is another exploded view of the sub-assembly shown in FIG. 6A.

Figure 6F:
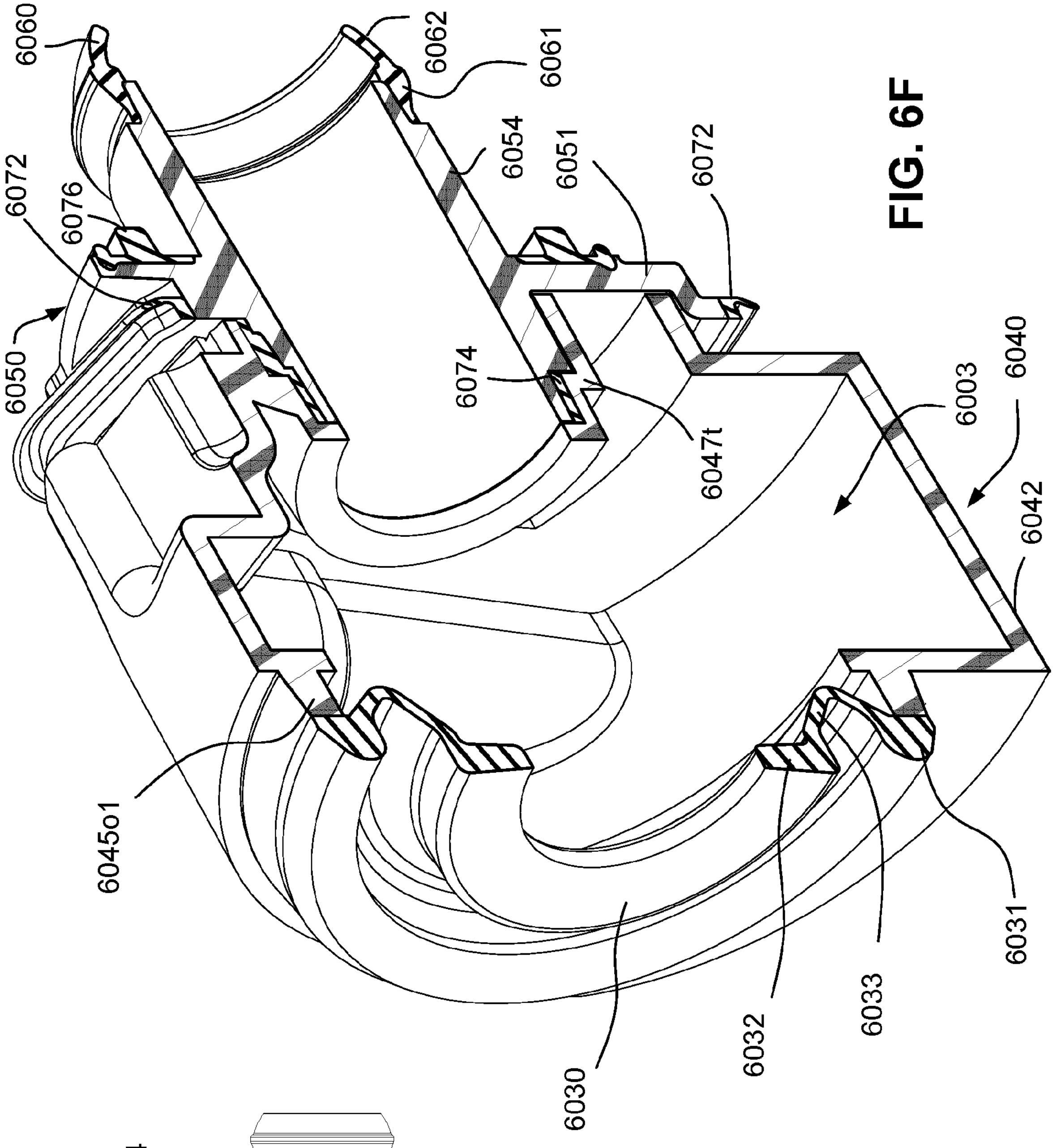
Figure 6E:
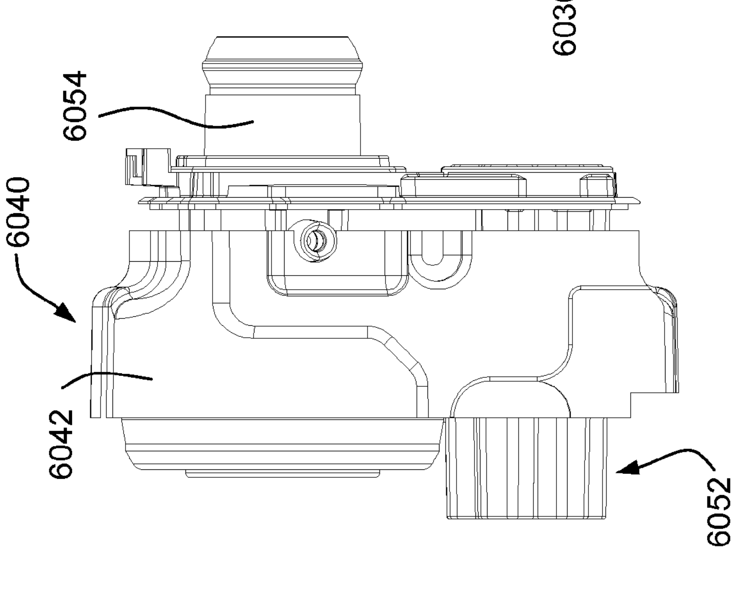

FIG. 6E is a top view of the sub-assembly shown in FIG. 6A.

FIG. 6F is a cross-sectional view through line 6F-6F of FIG. 6A.

Figure 6G:
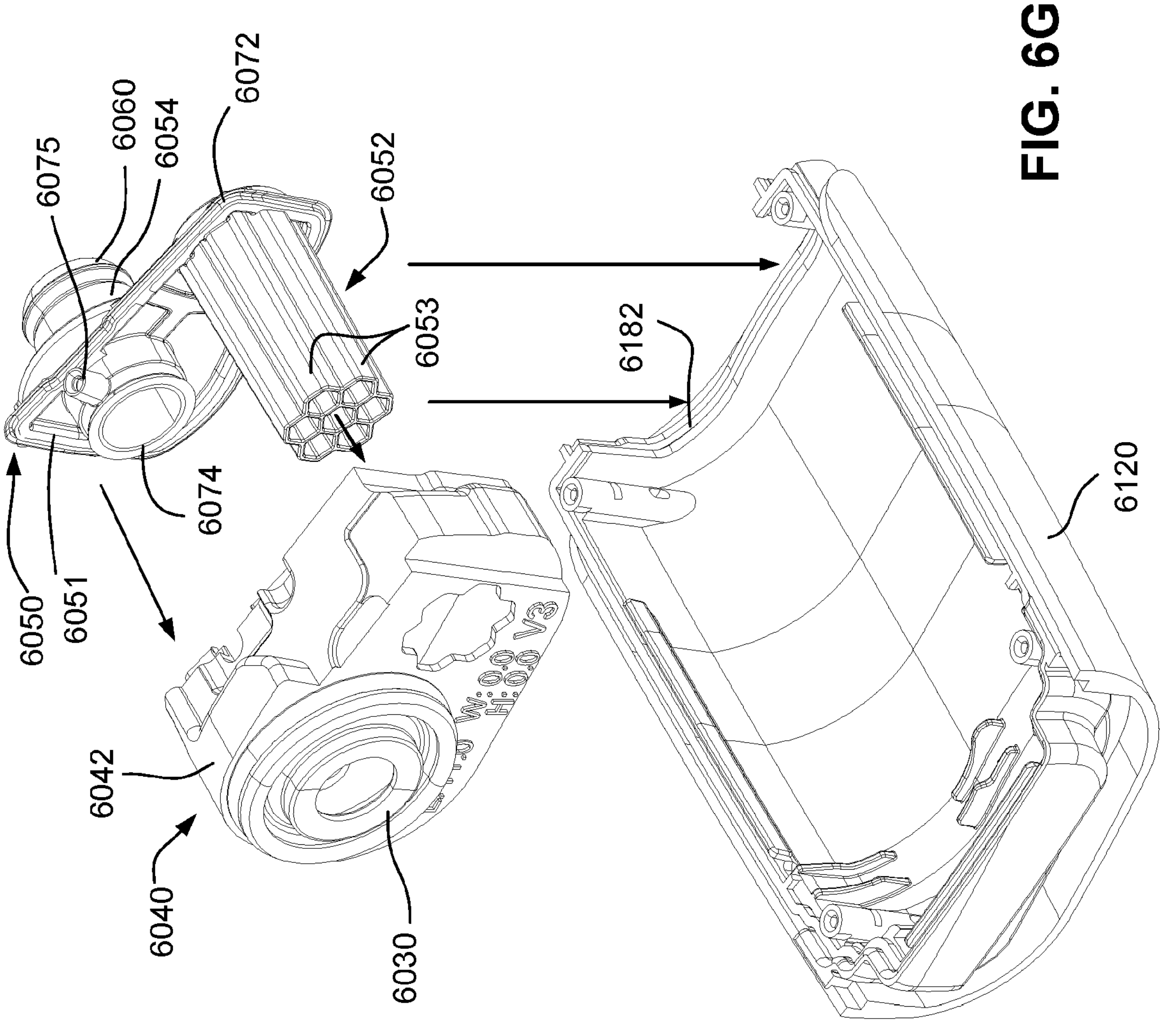

FIG. 6G is an exploded view showing an inlet/outlet assembly, a main body of a blower outlet muffler, and a lower portion of an enclosure according to an example of the present technology.

Figure 6H:
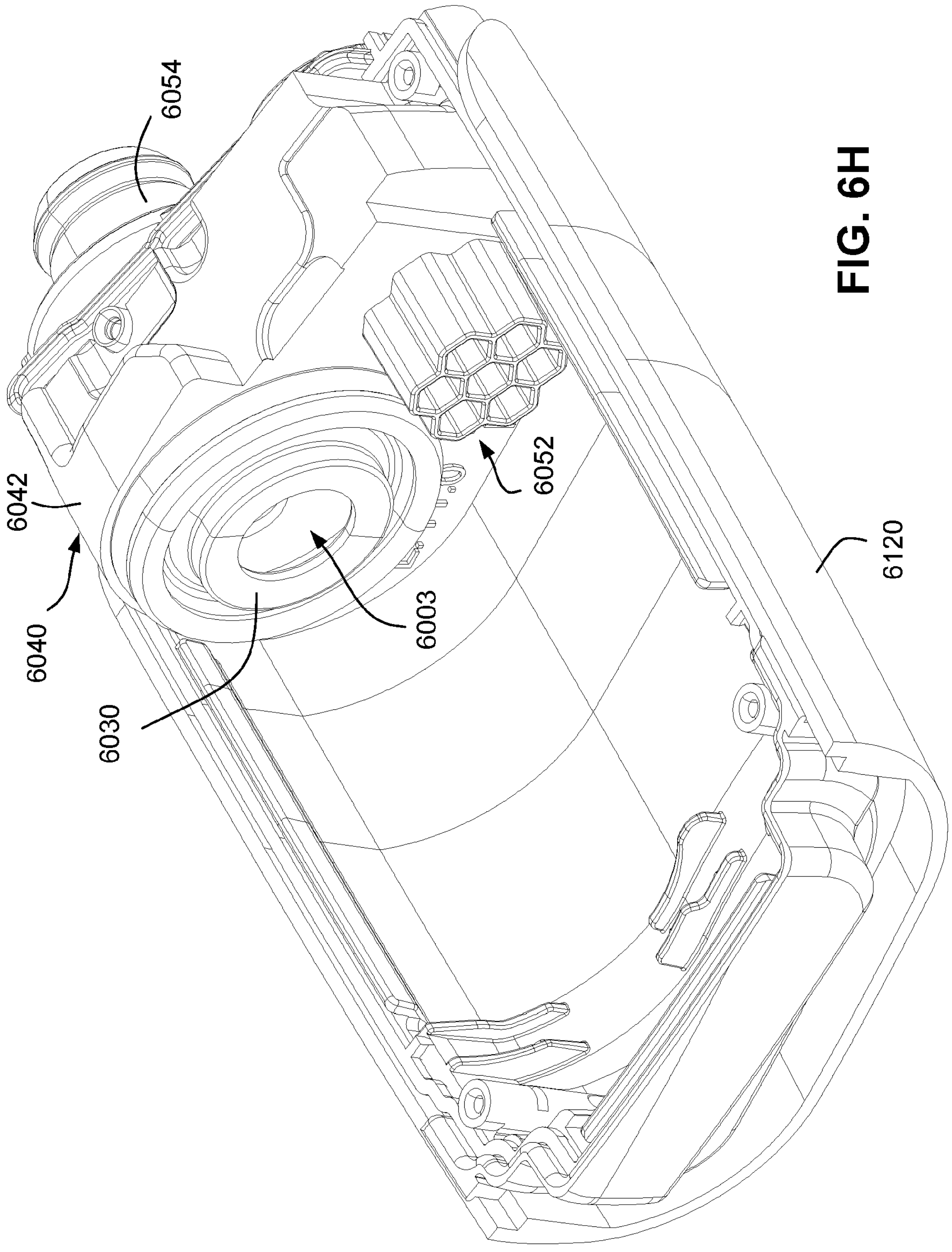

FIG. 6H is a perspective view showing an inlet/outlet assembly and a main body of a blower outlet muffler within a lower portion of an enclosure according to an example of the present technology.

Figures 6I, 6J:
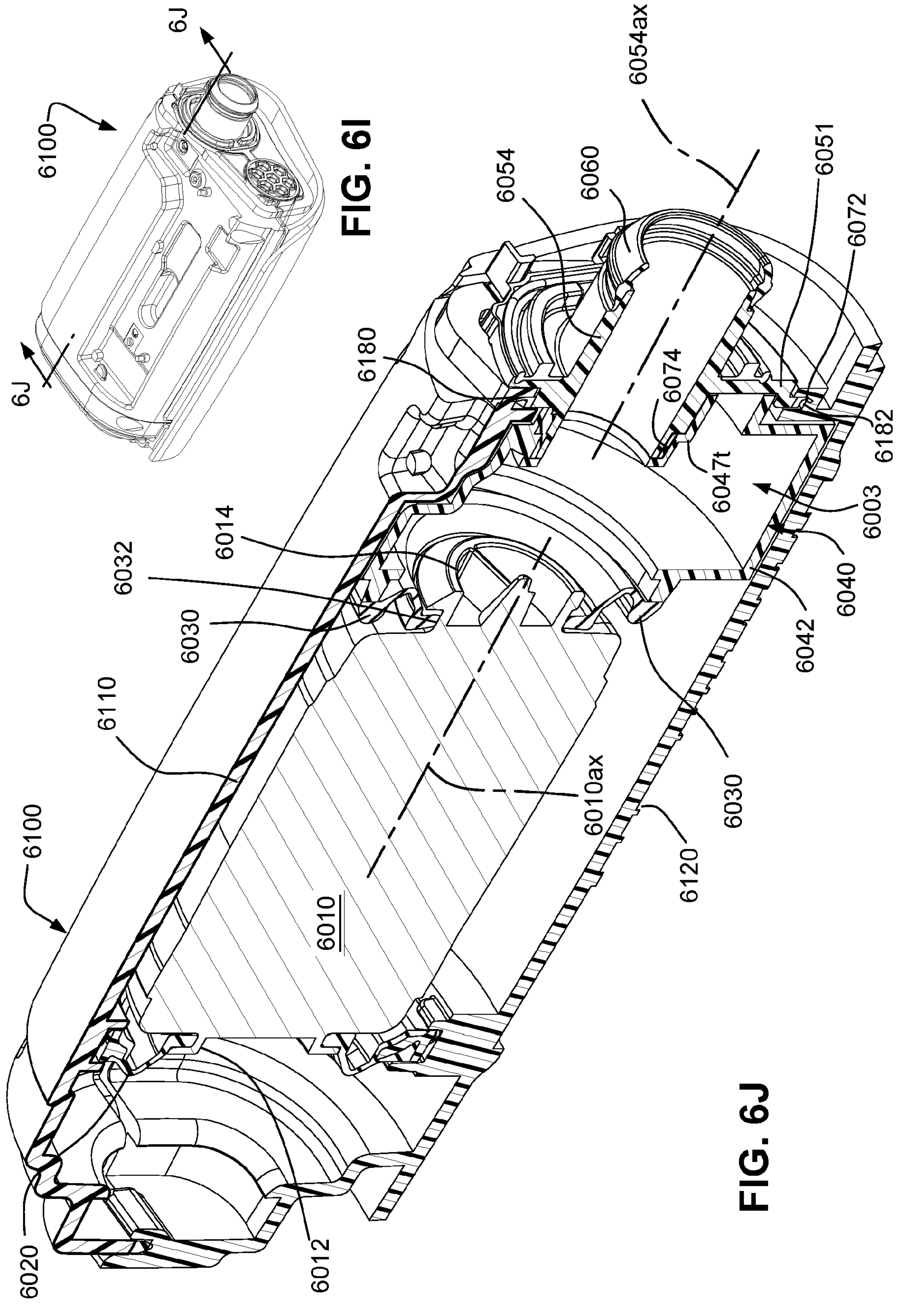

FIG. 6I is a perspective view of an enclosure of an RPT device according to an example of the present technology.

FIG. 6J is a perspective cross-sectional view through line 6J-6J of FIG. 6I.

Figures 6K, 6L:
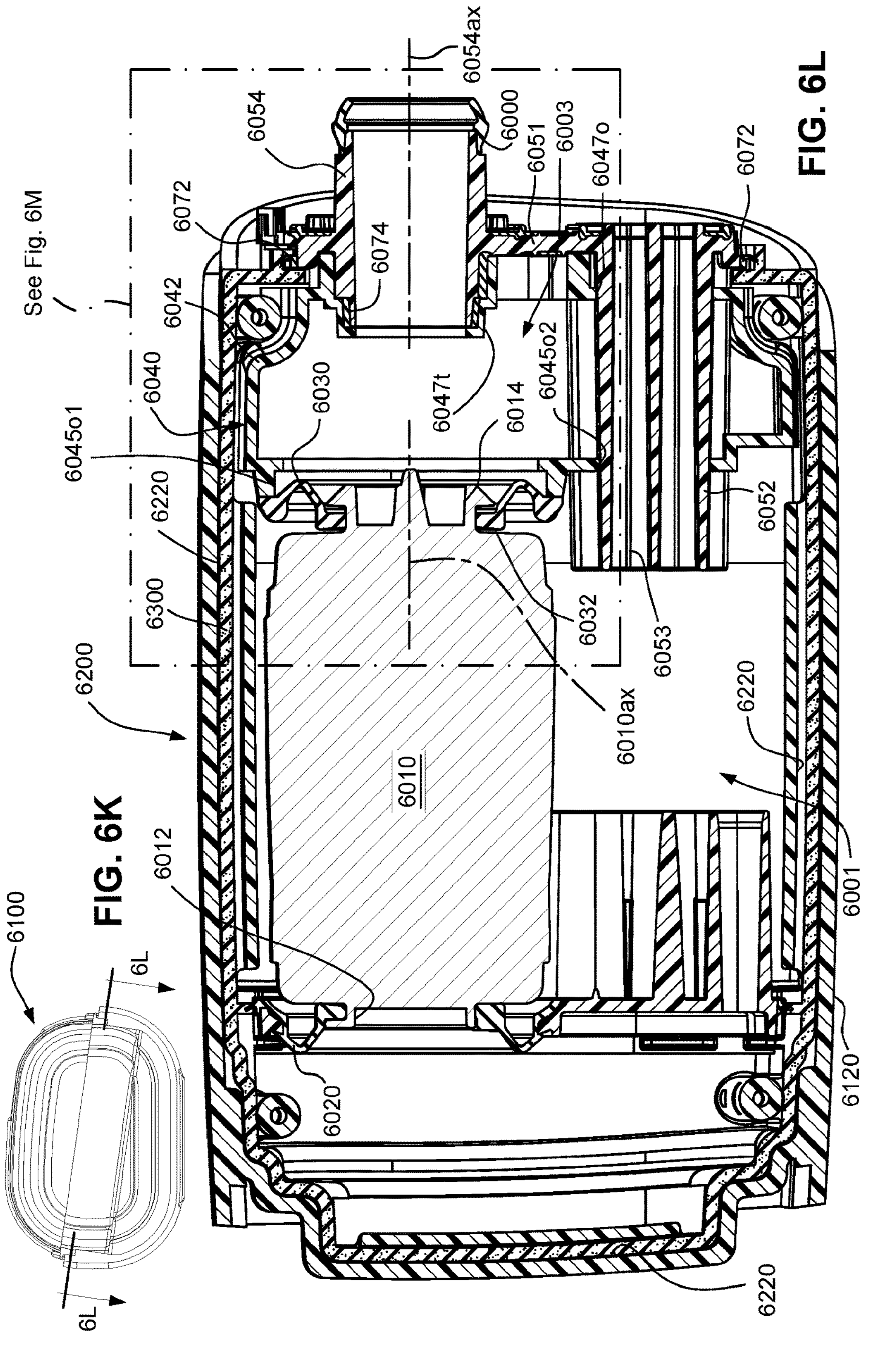

FIG. 6K is an end view of an enclosure of an RPT device according to an example of the present technology.

FIG. 6L is a cross-sectional view through line 6L-6L of FIG. 6K.

Figure 6M:
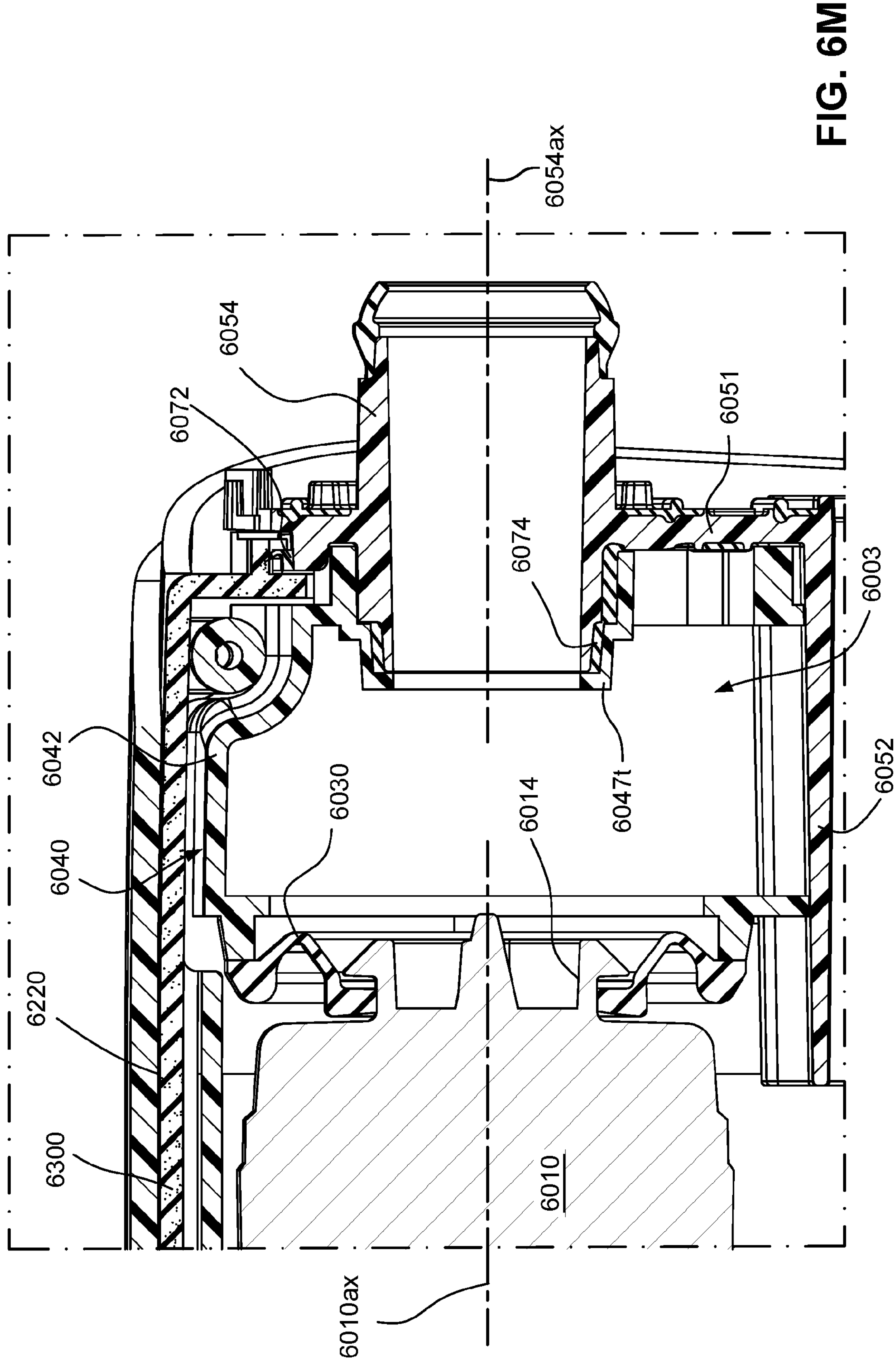

FIG. 6M is an enlarged cross-sectional view showing a portion of FIG. 6L.

Figure 6O:
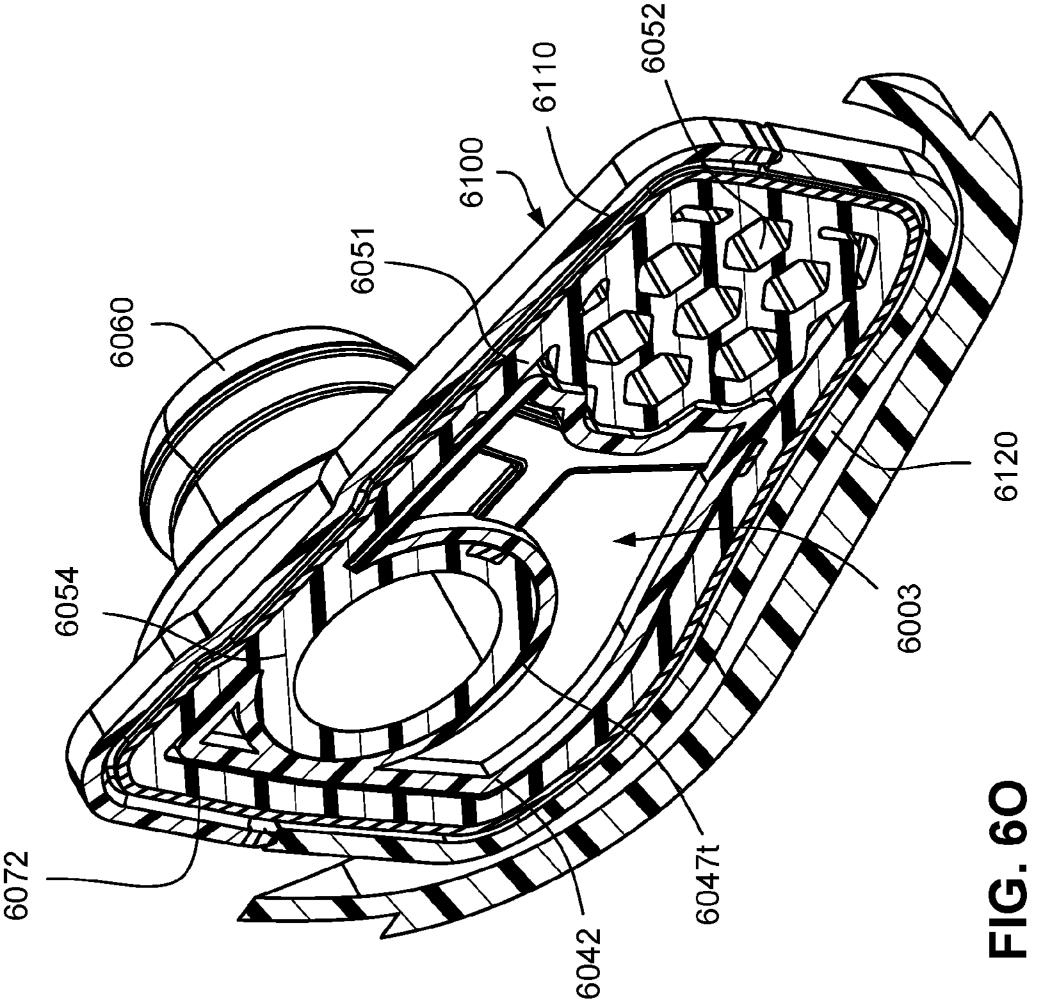
Figure 6N:
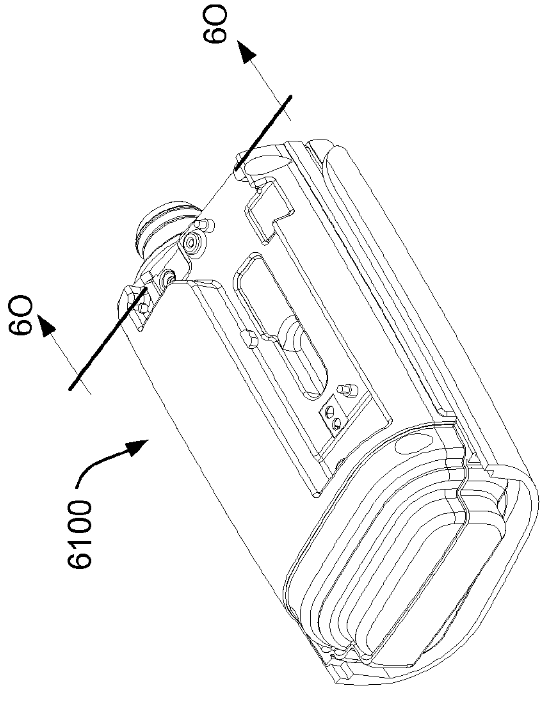

FIG. 6N is a perspective view of an enclosure of an RPT device according to an example of the present technology.

FIG. 6O is a perspective cross-sectional view through line 6O-6O of FIG. 6N.

Figure 6P:
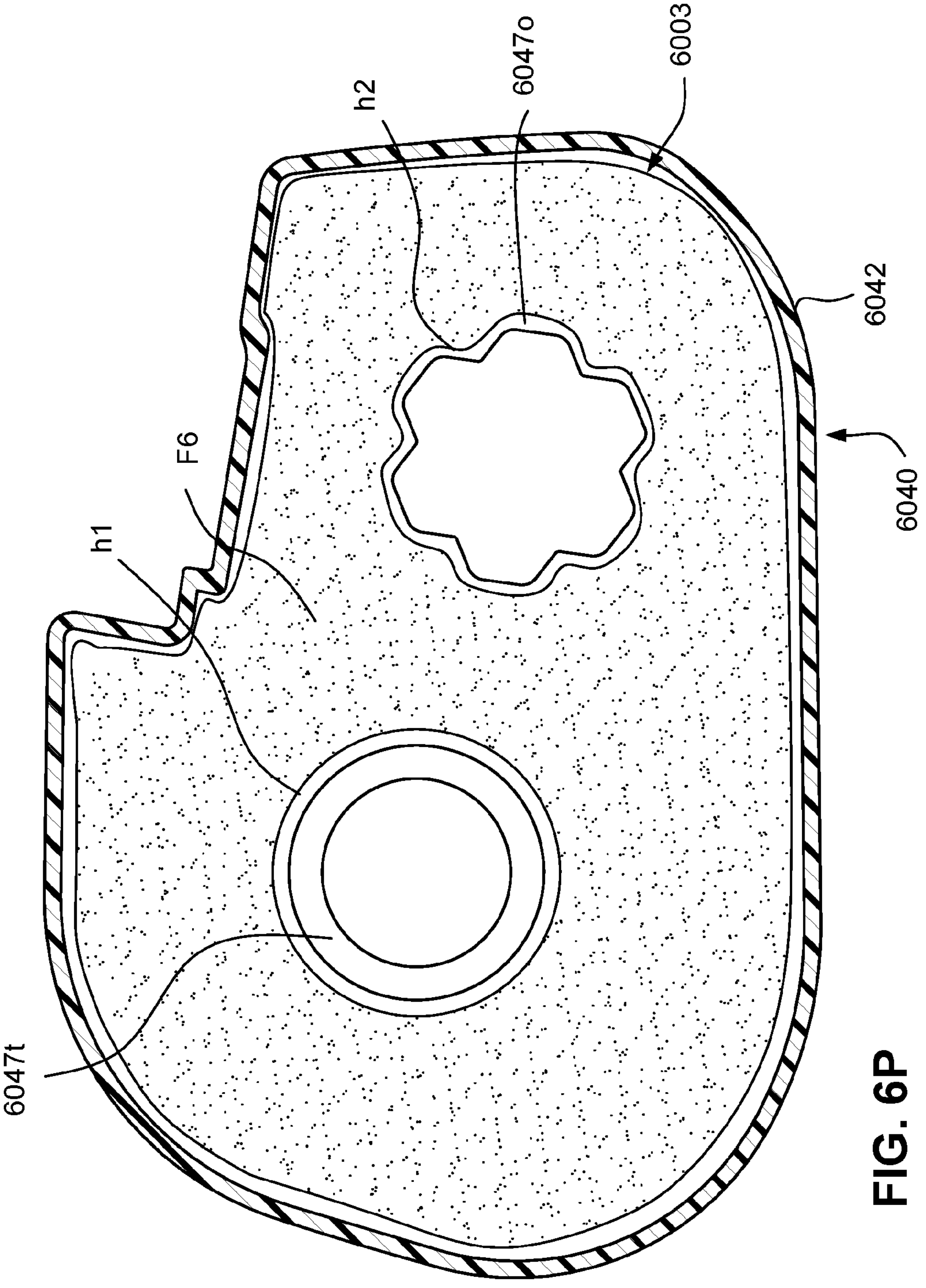

FIG. 6P is a cross-sectional view showing a main body and noise attenuating material (e.g., foam) of a blower outlet muffler according to an example of the present technology.

Figure 6Q:
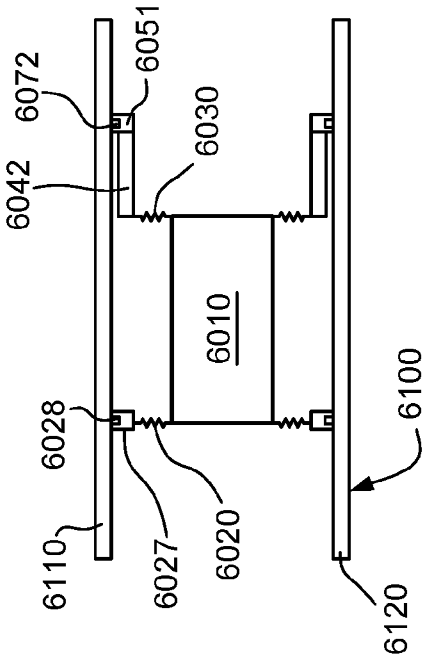

FIG. 6Q is a schematic diagram showing dynamic support of a blower within an enclosure according to an example of the present technology.

Figure 6R:
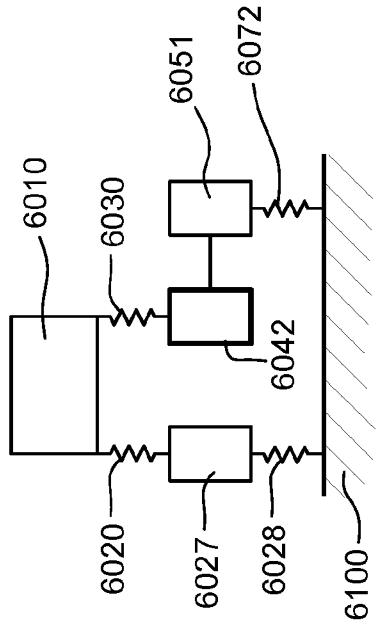

FIG. 6R is another schematic diagram showing dynamic support of a blower within an enclosure according to an example of the present technology.

Figure 7A:
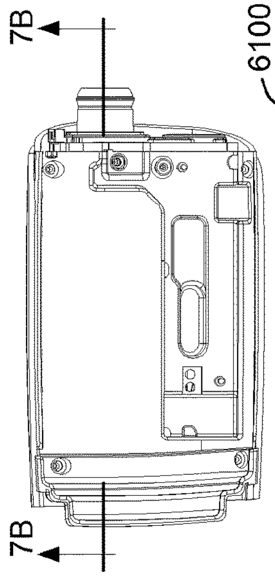

FIG. 7A is a top view of an enclosure of an RPT device according to an example of the present technology.

Figure 7B:
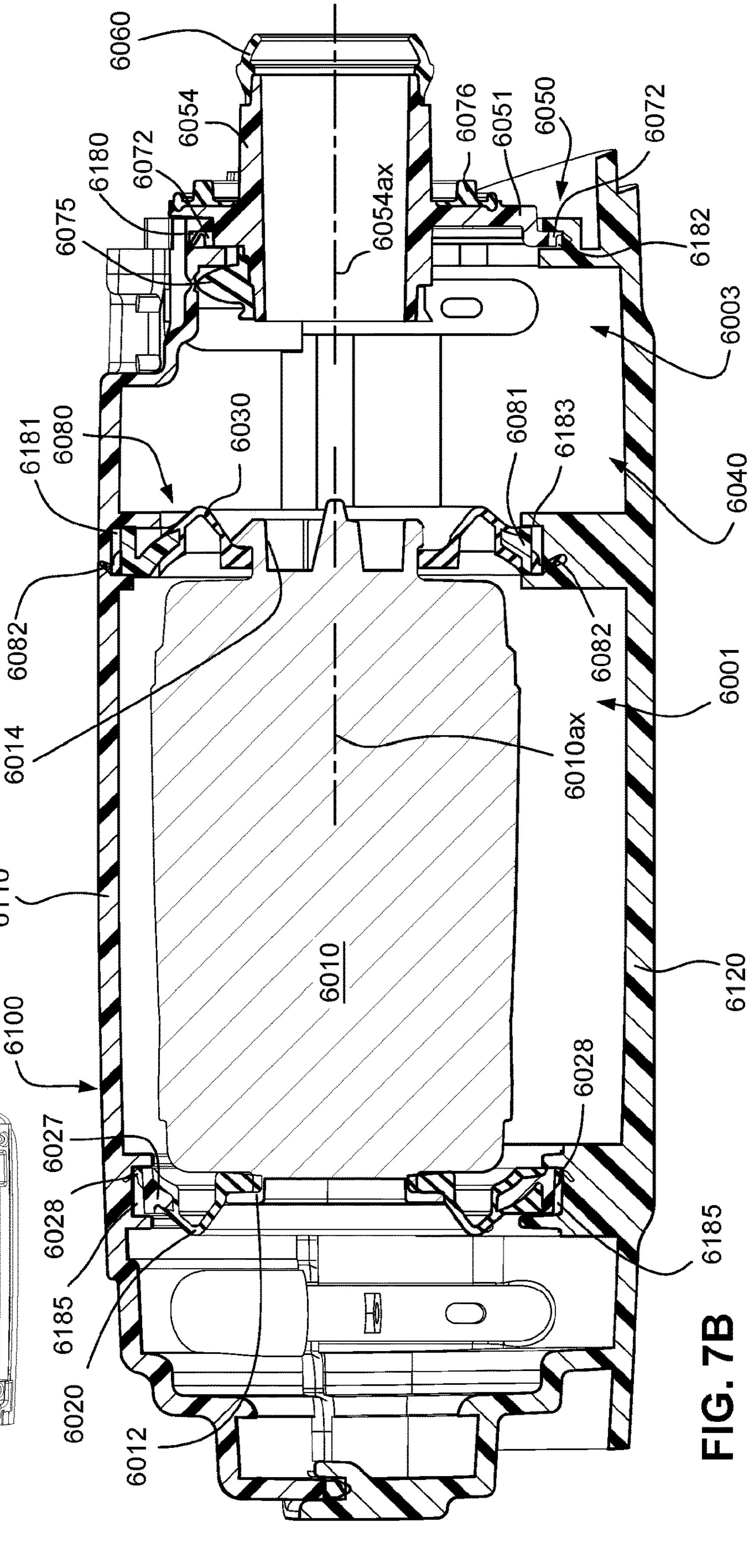

FIG. 7B is a cross-sectional view through line 7B-7B of FIG. 7A.

Figure 7C:
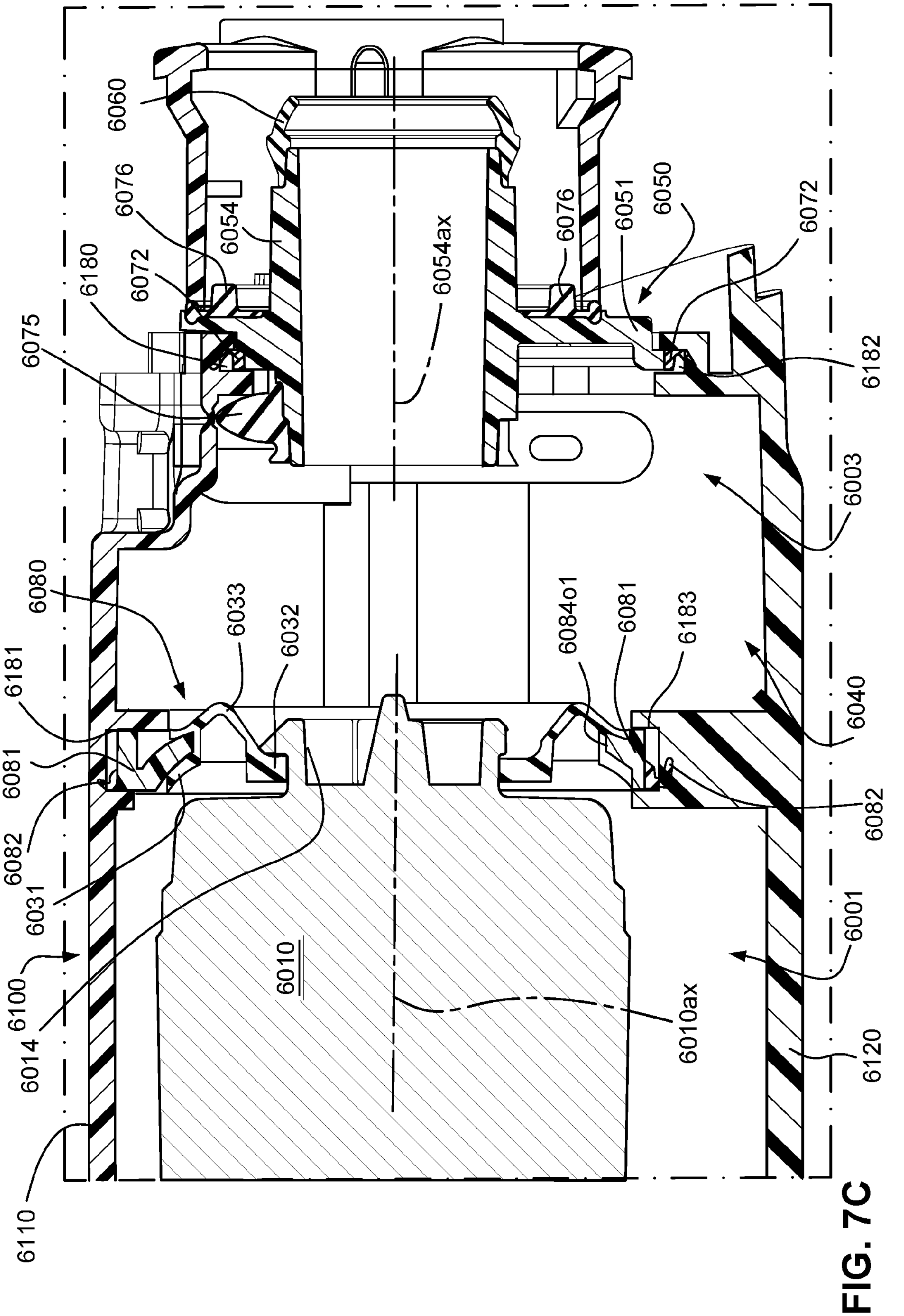

FIG. 7C is an enlarged cross-sectional view showing a portion of FIG. 7B.

Figure 7D:
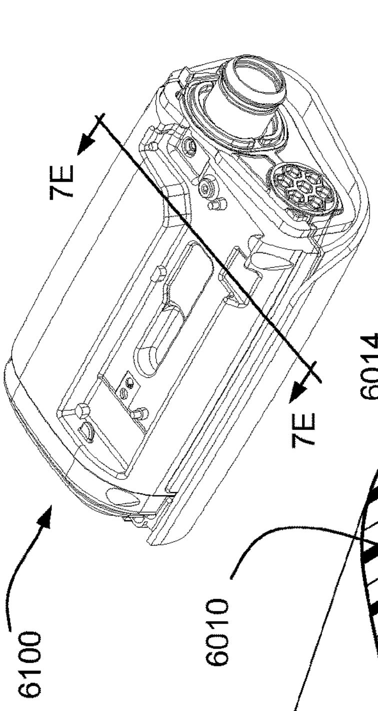

FIG. 7D is a perspective view of an enclosure of an RPT device according to an example of the present technology.

Figure 7E:
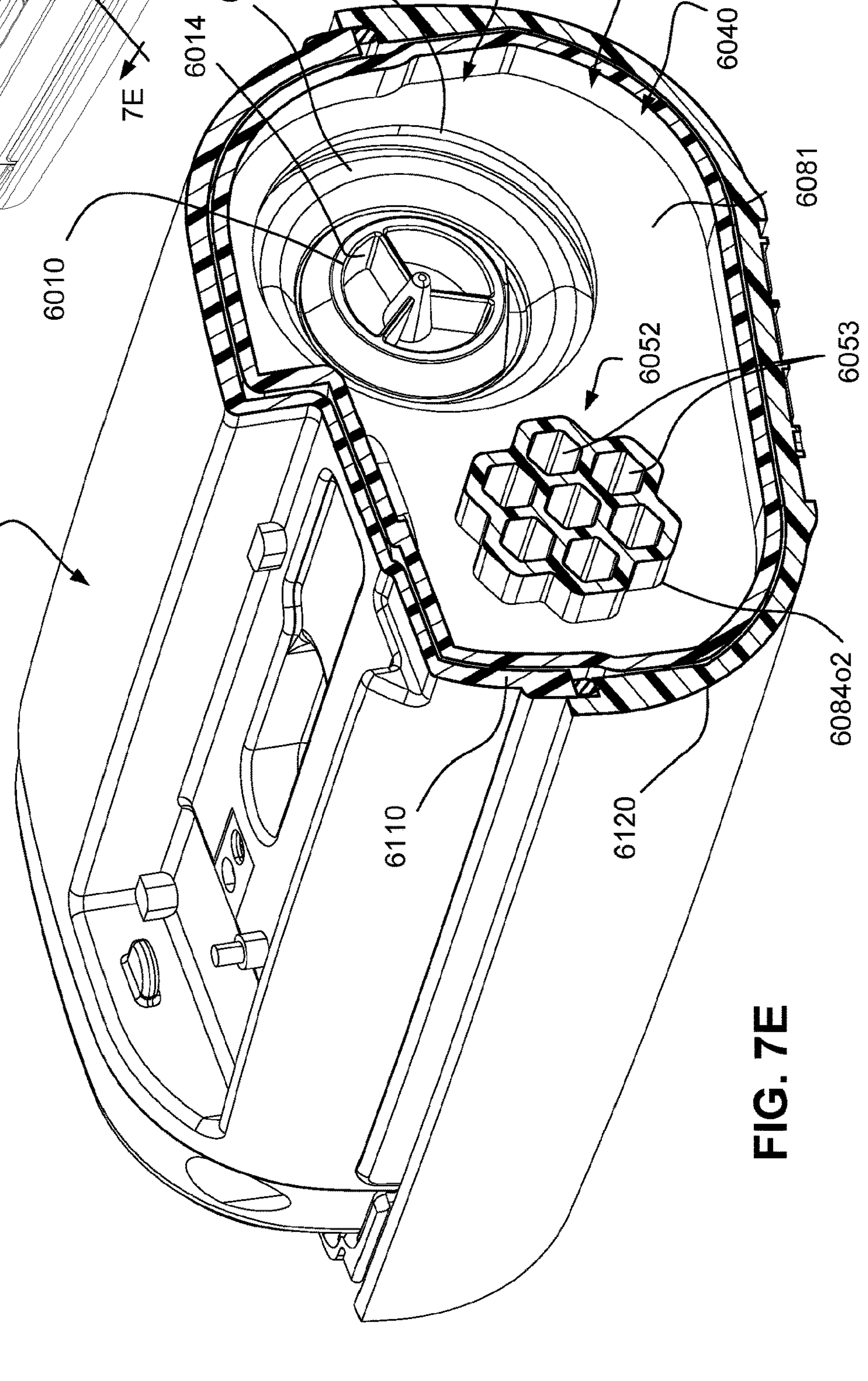

FIG. 7E is perspective cross-sectional view through line 7E-7E of FIG. 7D.

Figure 7F:
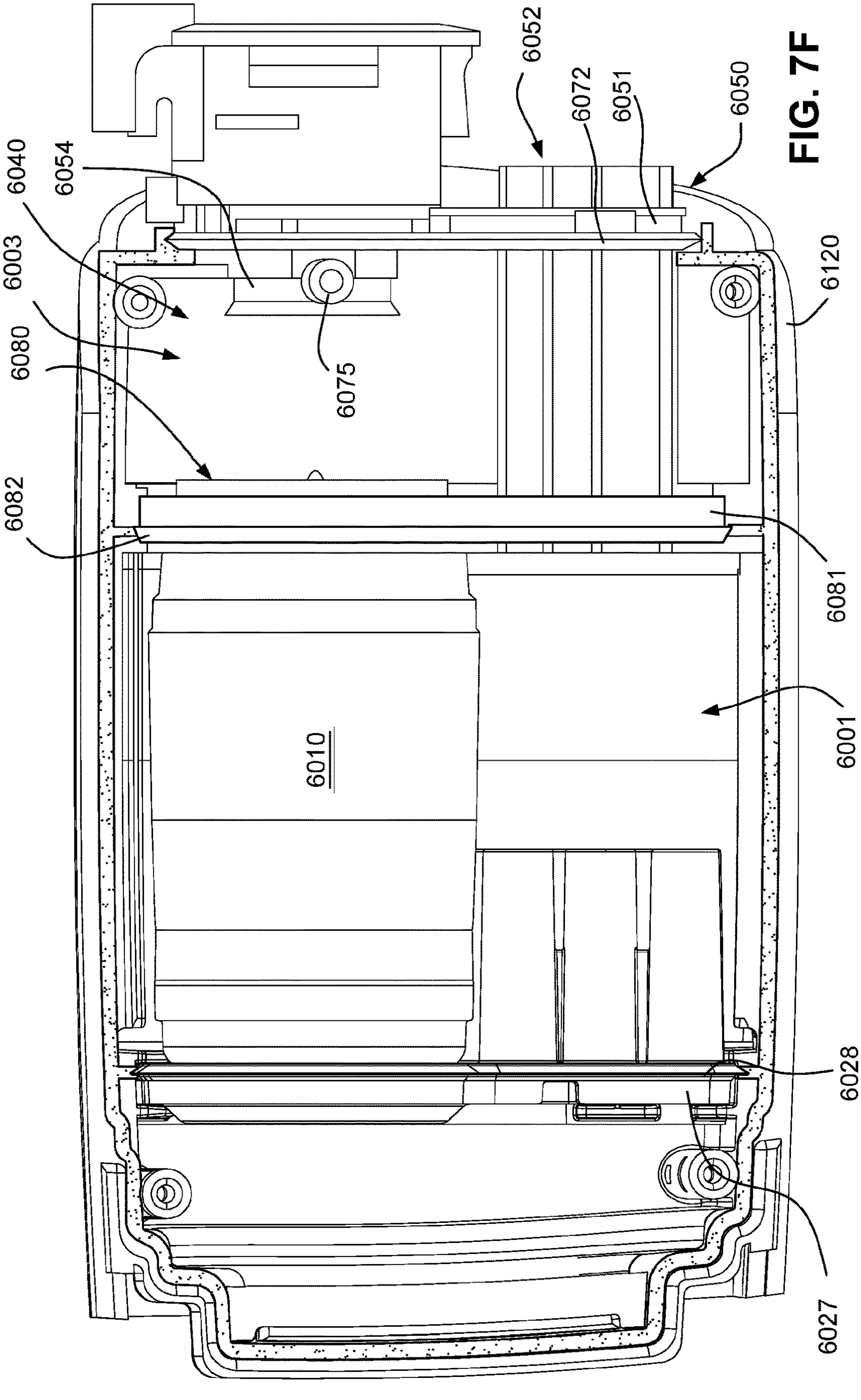

FIG. 7F is a top cross-sectional view showing internal components of the RPT device of FIG. 7B within a lower portion of the enclosure, with an upper portion of the enclosure removed, according to an example of the present technology.

Figure 7G:
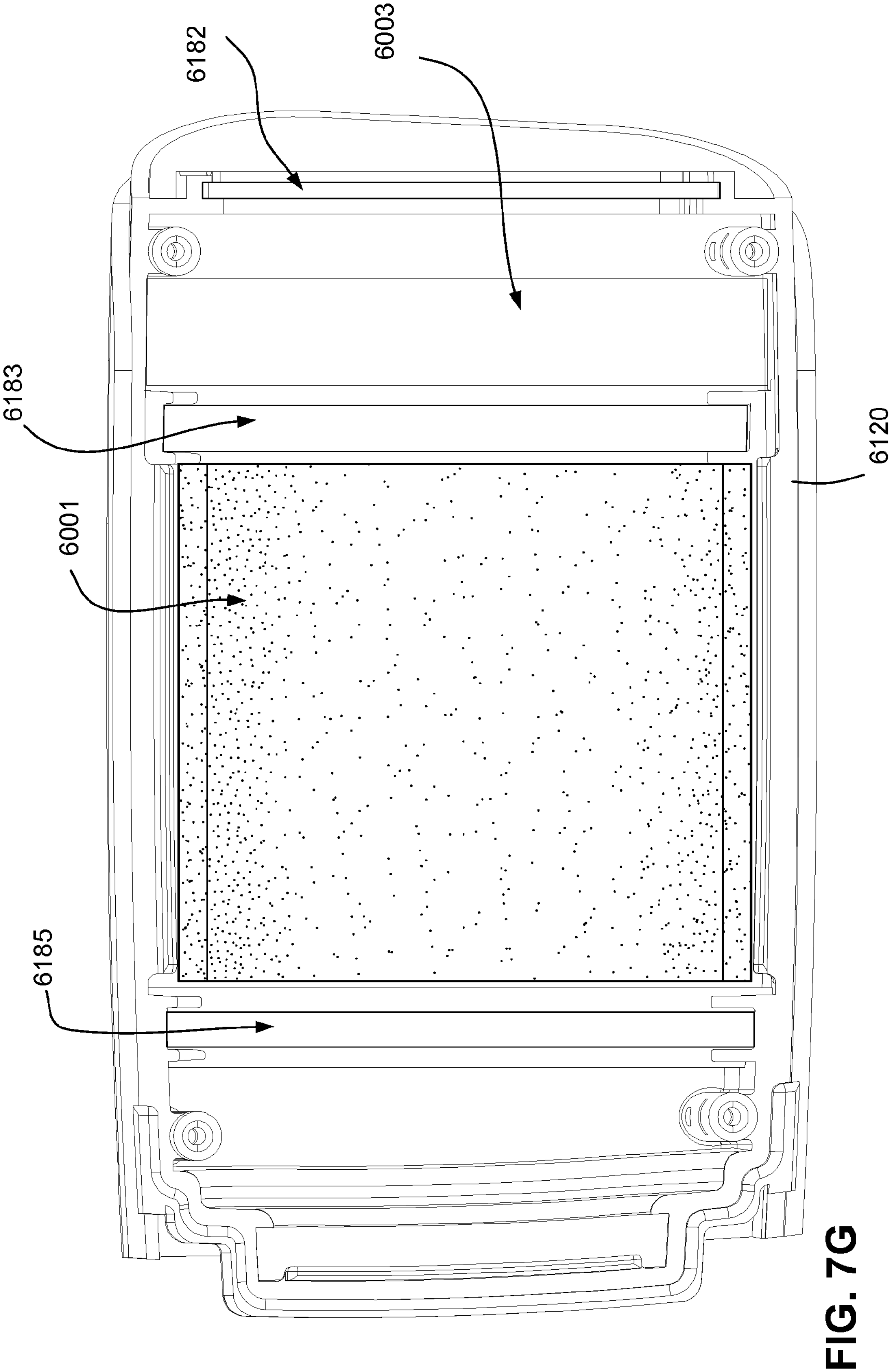

FIG. 7G is a top view showing a lower portion of the enclosure of the RPT device of FIG. 7B according to an example of the present technology.

Figure 7H:
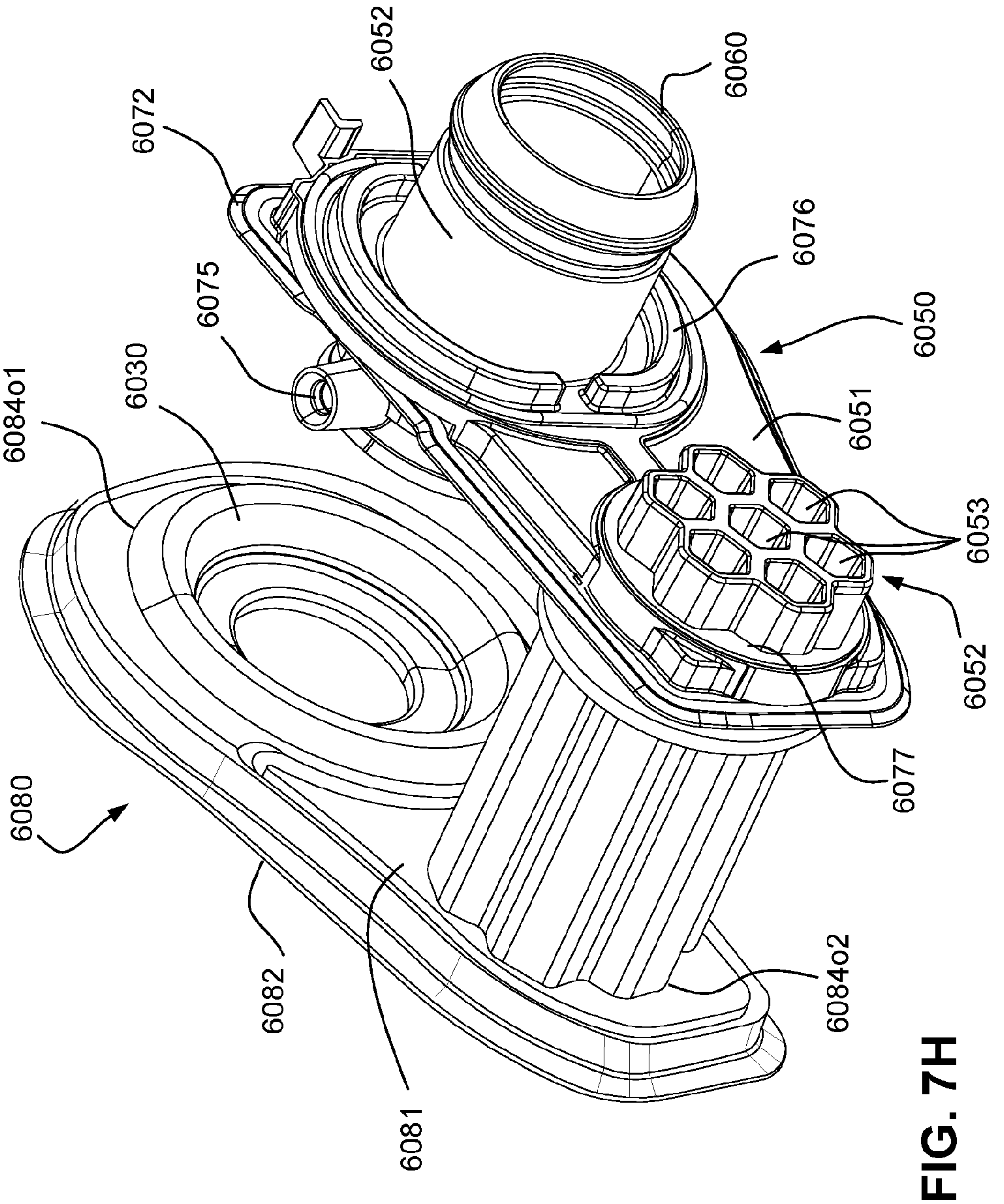

FIG. 7H is a perspective view showing an inlet/outlet assembly and a blower outlet end suspension assembly of the RPT device of FIG. 7B according to an example of the present technology.

Figure 7I:
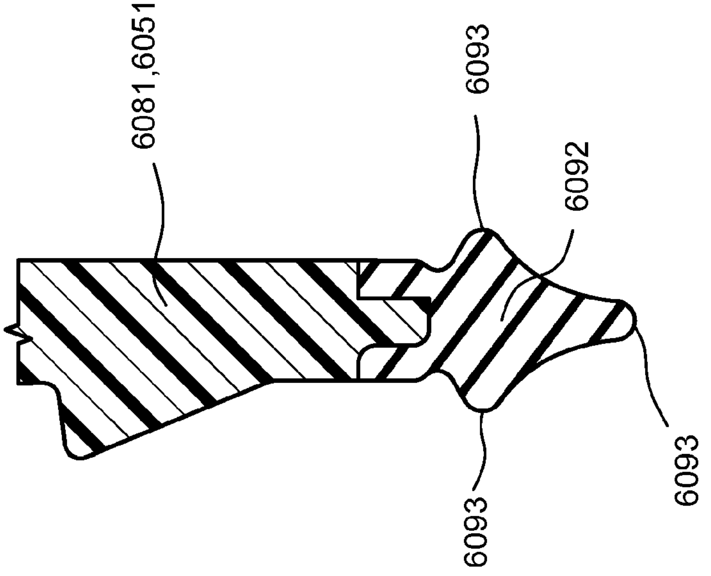

FIG. 7I is a cross-sectional view showing a multi-lobe seal for a base plate according to an example of the present technology.

Figure 7J:
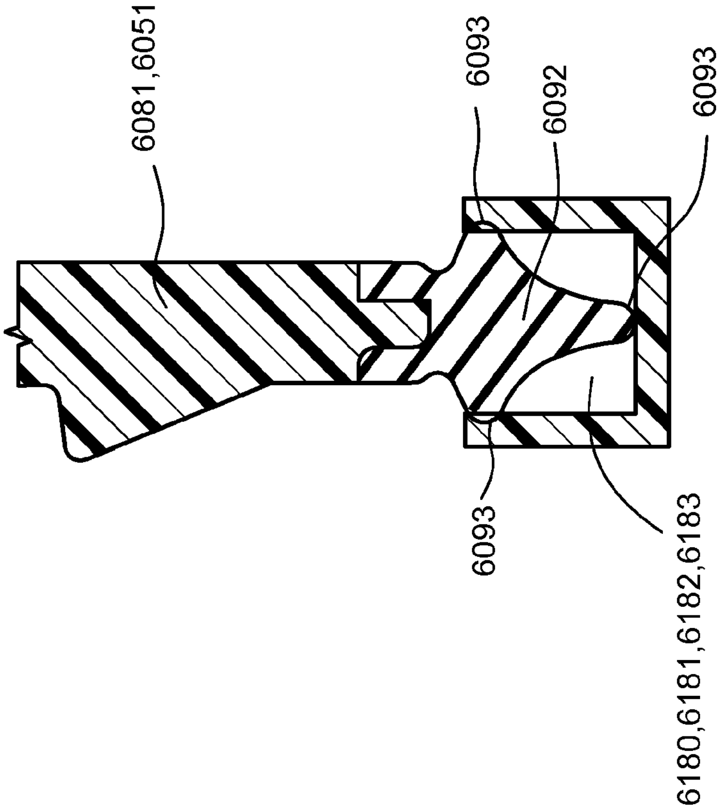

FIG. 7J is a cross-sectional view showing the multi-lobe seal of FIG. 7I engaged within a groove of a portion of an enclosure according to an example of the present technology.

Figure 7K:
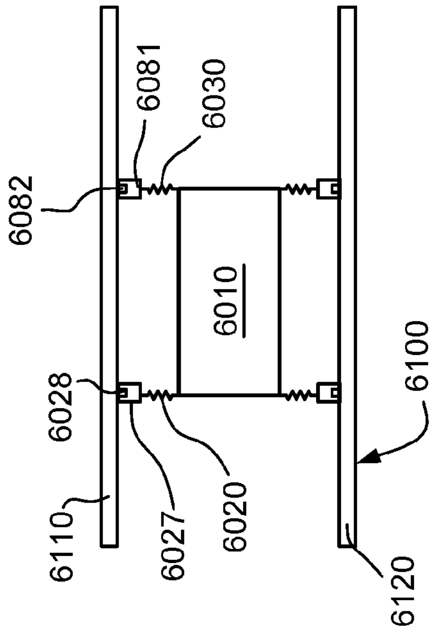

FIG. 7K is a schematic diagram showing dynamic support of a blower within an enclosure according to an example of the present technology.

Figure 7L:
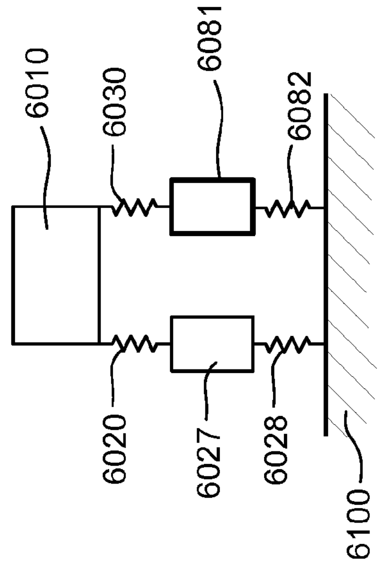

FIG. 7L is another schematic diagram showing dynamic support of a blower within an enclosure according to an example of the present technology.

4.4 Humidifier

Figure 8A:
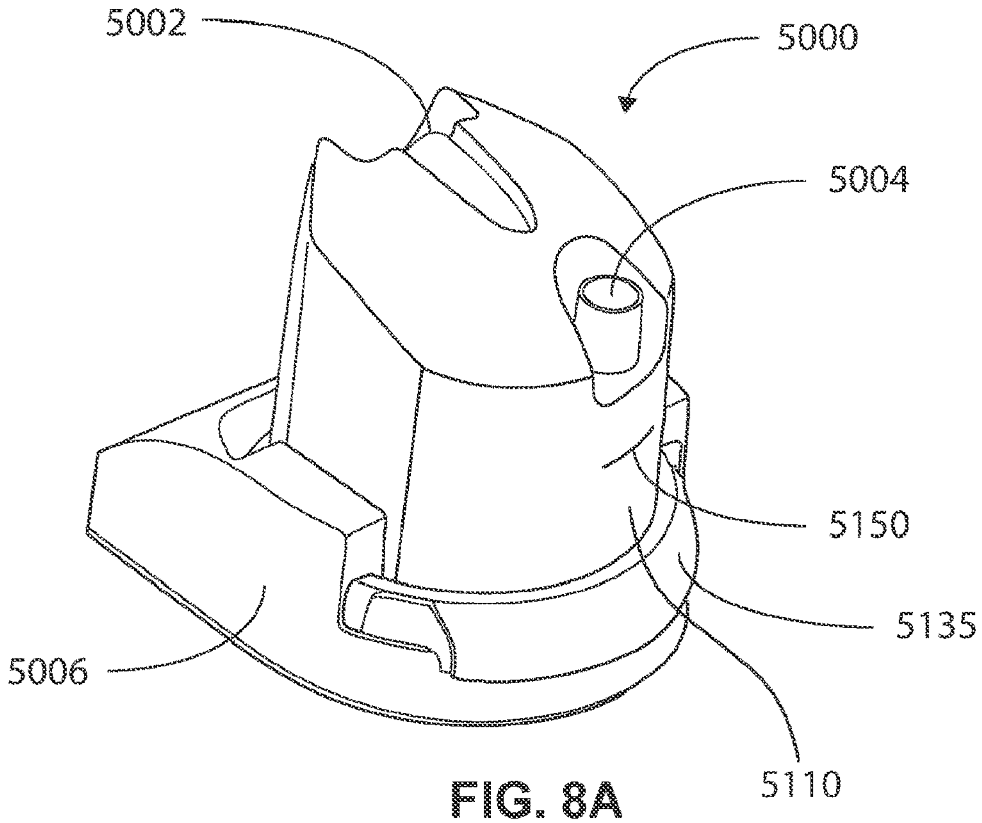

FIG. 8A shows an isometric view of a humidifier in accordance with one form of the present technology.

Figure 8B:
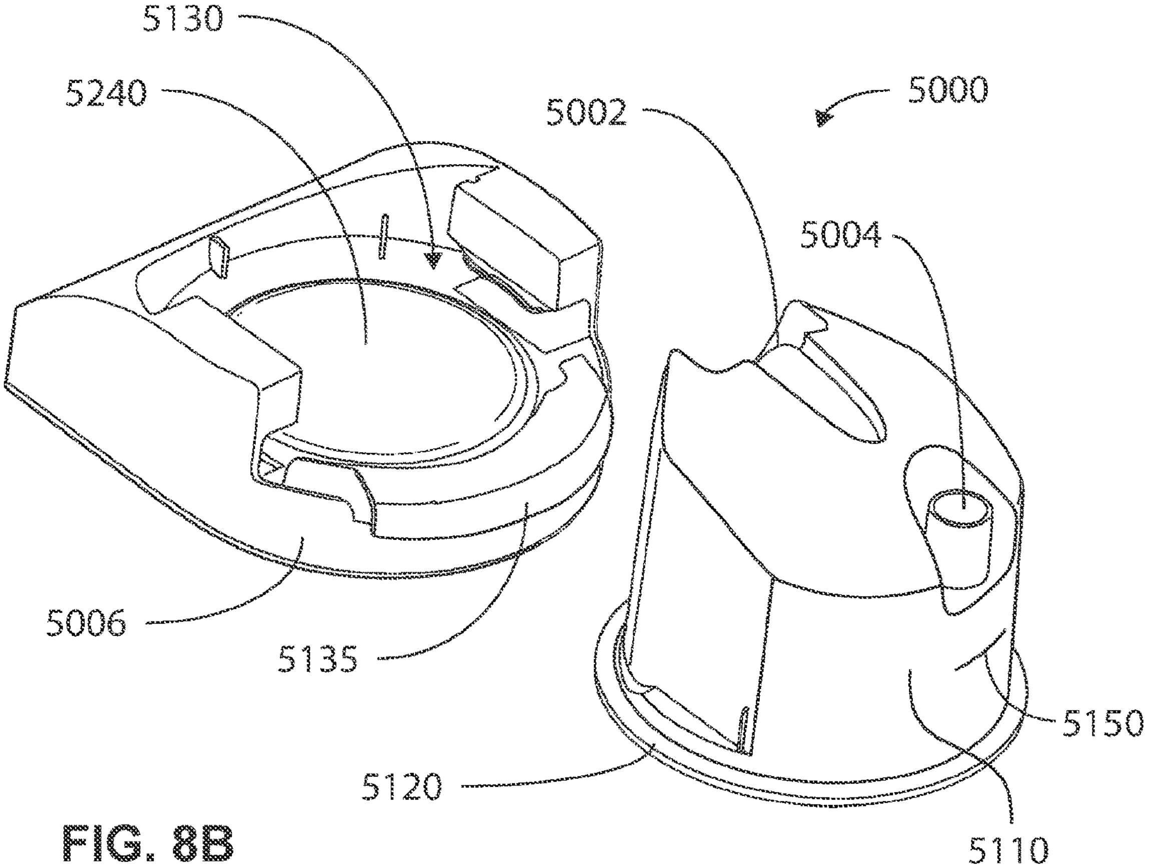

FIG. 8B shows an isometric view of a humidifier in accordance with one form of the present technology, showing a humidifier reservoir 5110 removed from the humidifier reservoir dock 5130.

4.5 Breathing Waveforms

Figure 9:
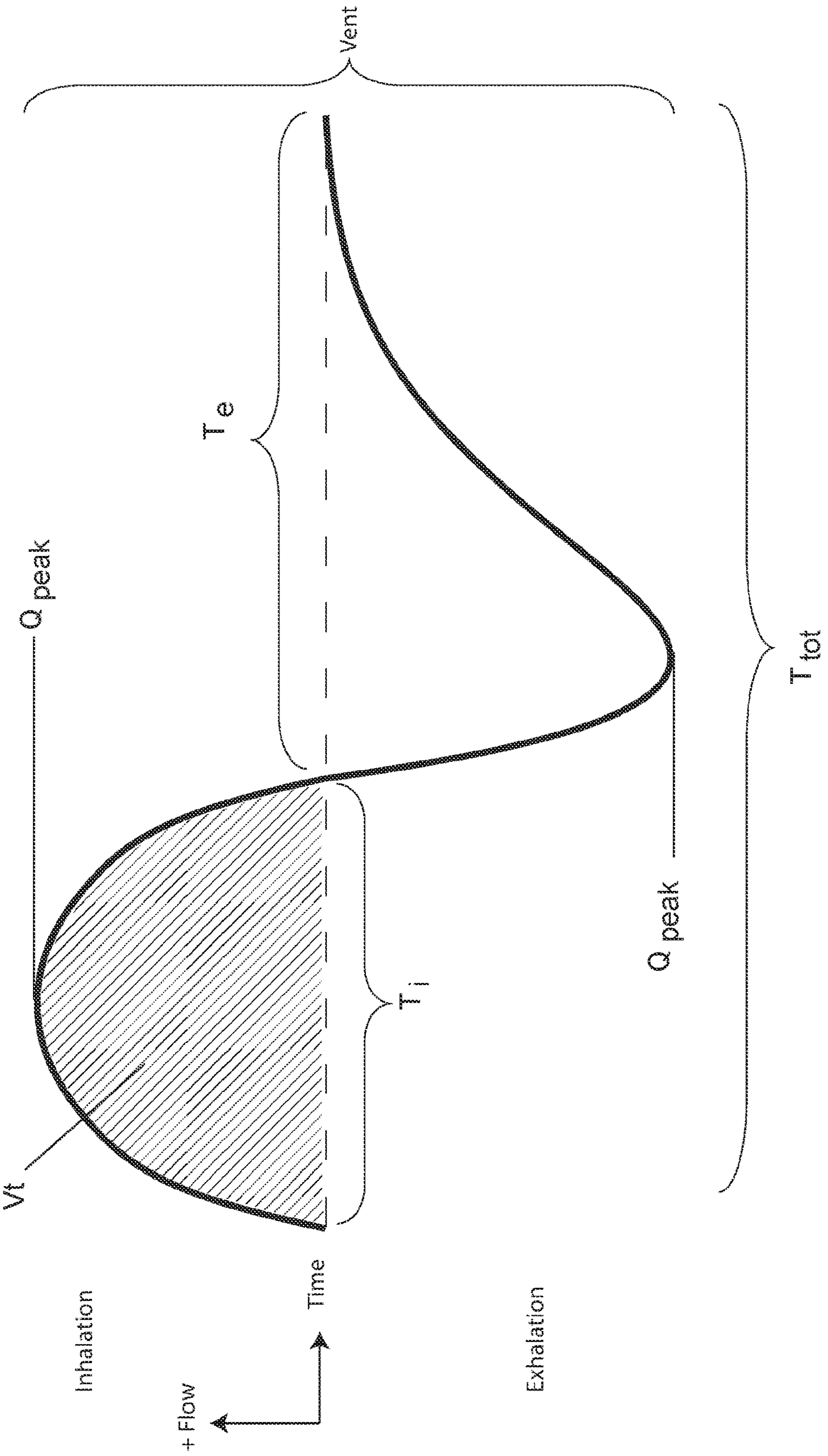

FIG. 9 shows a model typical breath waveform of a person while sleeping.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 6000 according to an example of the present technology for supplying a flow of air to the patient 1000 via an air circuit 4170 and a patient interface 3000, e.g., see FIG. 1.

5.3 Patient Interface

Figure 2A:
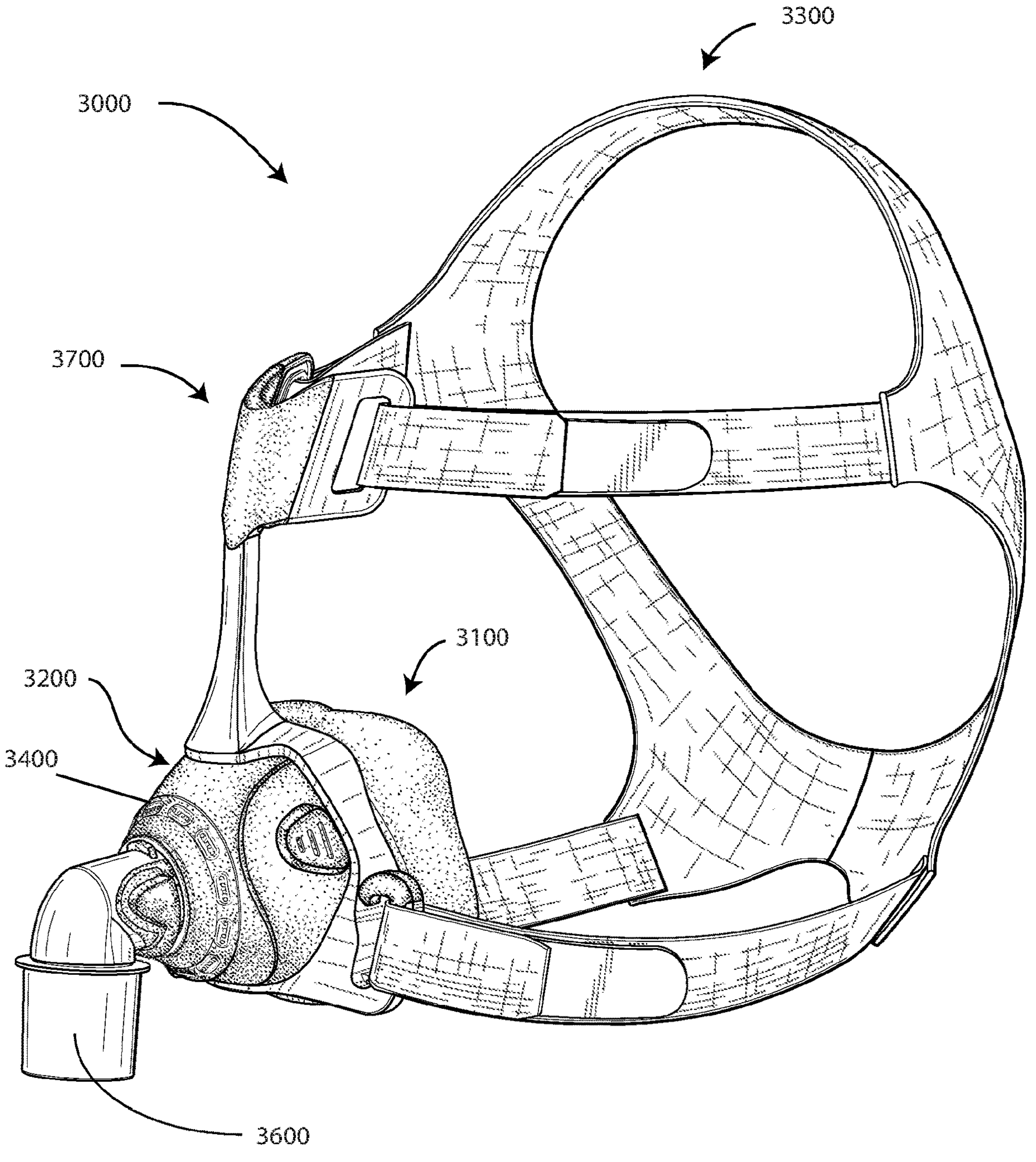

FIG. 2A shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

5.4 RPT Device

An RPT device 4000, 6000 in accordance with one aspect of the present technology comprises mechanical, pneumatic, and/or electrical components and is configured to execute one or more algorithms 4300, such as any of the methods, in whole or in part, described herein. The RPT device 4000, 6000 may be configured to generate a flow of air for delivery to a patient's airways, such as to treat one or more of the respiratory conditions described elsewhere in the present document.

In one form, the RPT device 4000, 6000 is constructed and arranged to be capable of delivering a flow of air in a range of −20 L/min to +150 L/min while maintaining a positive pressure of at least 6 cmH2O, or at least 10 cmH2O, or at least 20 cmH2O.

FIGS. 4A to 4E relate to an RPT device 4000 in accordance with one form of the present technology, which includes one or more aspects that may be combinable with alternative examples described herein, e.g., RPT device 6000. That is, the RPT device 6000 may include any and all of the features described in relation to the RPT device 4000. Likewise, the RPT device 4000 may include any and all of the features described in relation to the RPT device 6000. As shown in FIG. 4A, the RPT device 4000 may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

Figure 1:
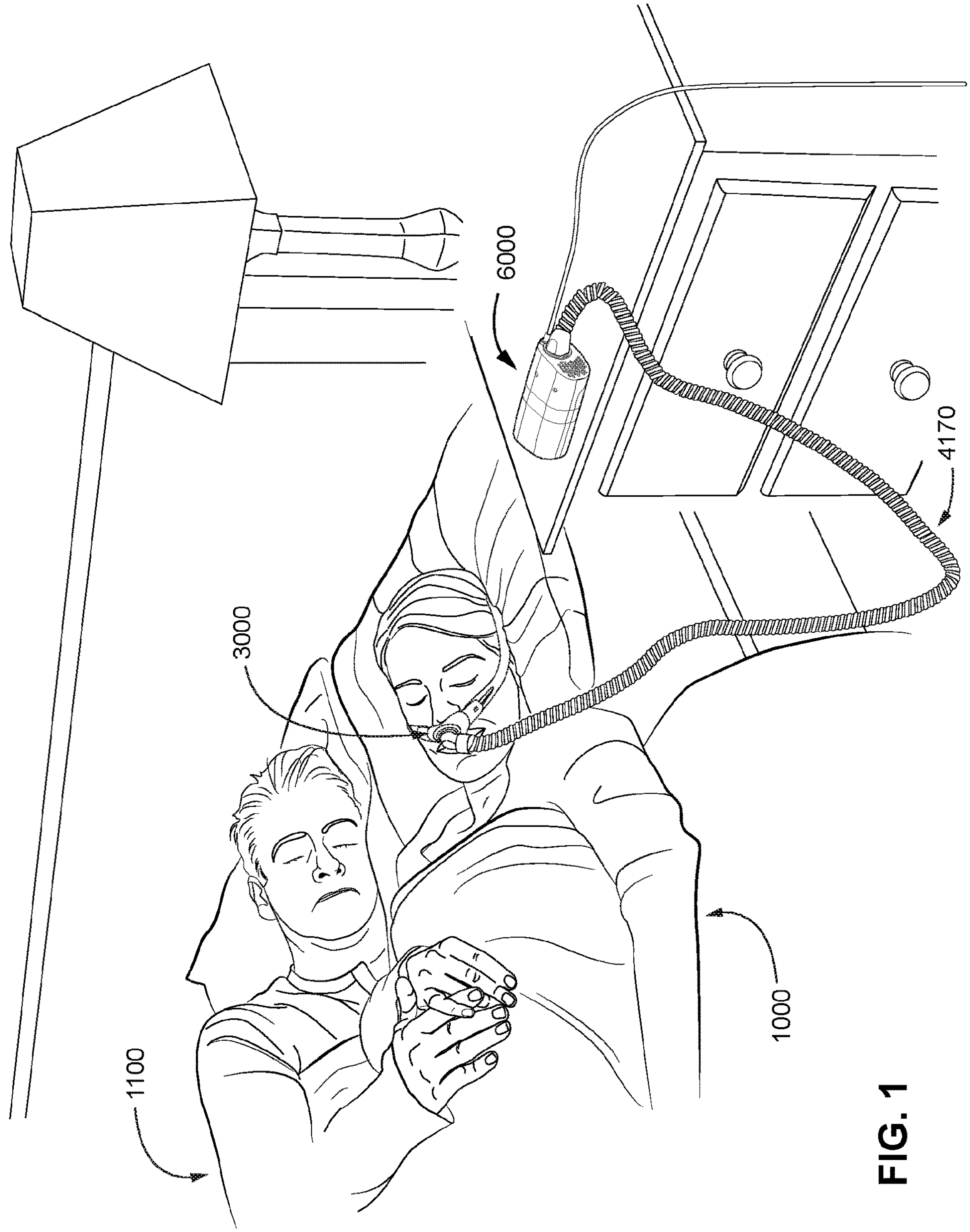
FIG. 3A-1 is a perspective view of an RPT device according to an example of the present technology.
Figures 2, 3A:
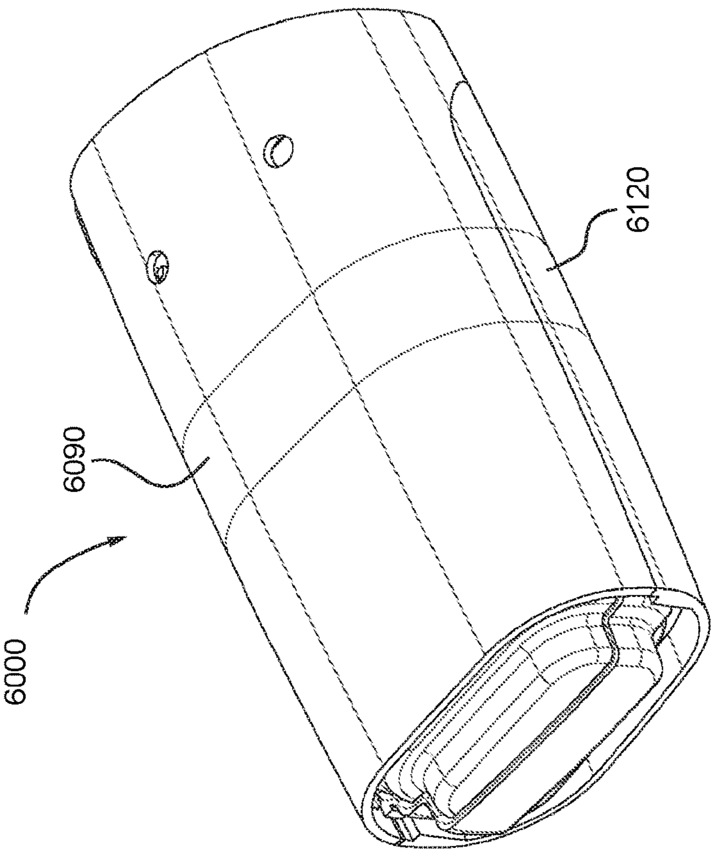
Figures 1, 3A:
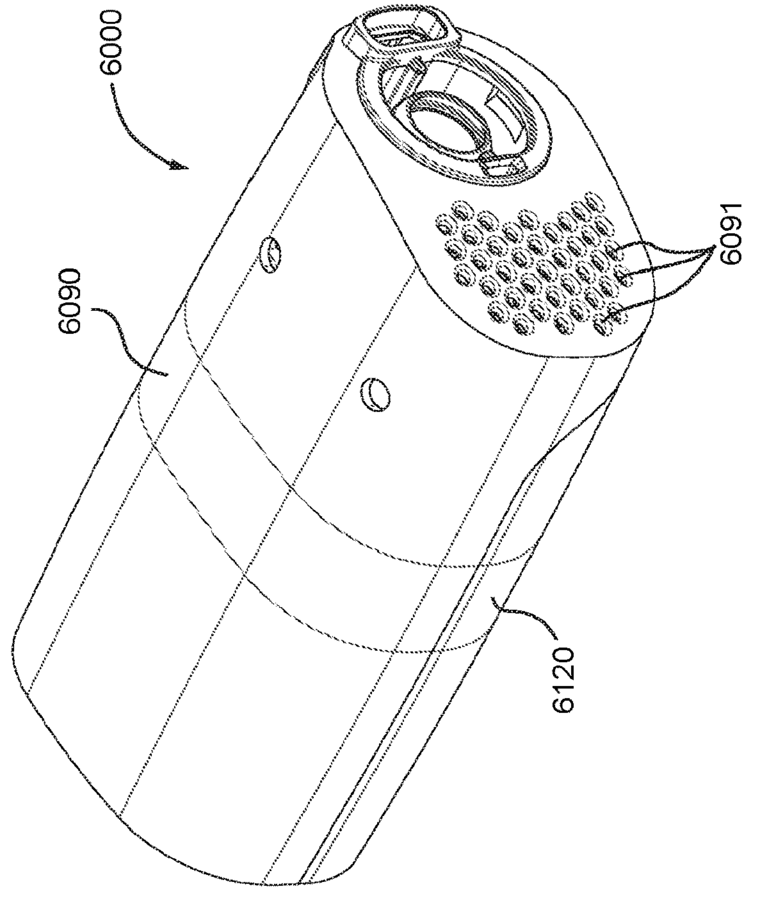

FIGS. 3A-1 and 3A-2 illustrate an RPT device 6000 according to an example of the present technology. As best shown in FIGS. 3B-1 to 3B-5, the RPT device 6000 is of a significantly reduced size compared to prior art RPT devices, including RPT device 4000. Because of the reduced size, standard noise reductions techniques can be more difficult to implement in RPT device 6000. One approach considered in the discussed RPT device 6000 includes amendments to various aspects of the housing of the device. As best shown in FIGS. 3C to 3L, the RPT device 6000 includes an enclosure 6100 (also referred to as a housing) to support and/or at least partially enclose one or more internal components of the RPT device 6000.

In the illustrated example, the enclosure 6100 is structured and arranged to at least partly support and/or enclose at least a blower 6010. The enclosure 6100 may also at least partly, directly or indirectly, support a blower suspension system (e.g., including a blower inlet end suspension 6020 to support the blower 6010 adjacent the blower inlet and a blower outlet end suspension 6030 to support the blower 6010 adjacent the blower outlet), an outlet muffler 6040, and/or an inlet/outlet assembly 6050 (see FIG. 3F) that includes an inlet tube array 6052 and an outlet tube 6054 (e.g., see FIGS. 3F to 3L). However, it should be appreciated that the enclosure 6100 may be structured and arranged to support and/or enclose more or fewer internal components than illustrated in the example.

In the illustrated example, the inlet tube array 6052 forms an inlet into the enclosure 6100 and the outlet tube 6054 forms an outlet out of the enclosure 6100. In this example, the inlet tube 6052 and the outlet tube 6054 are formed on the same side of the enclosure, which means that at least a first part of the air flow path flows in the opposite direction to that of a second part of the air flow path, e.g., the airflow path is substantially U-shaped. However, in alternative examples, the inlet and/or the outlet of the enclosure 6100 may be formed by one or more portions of the enclosure 6100 itself.

In an example, at least a portion of the enclosure 6100 may form a chamber that is structured and arranged so that the interior of the enclosure 6100 may be pressurized at a pressure at variance with ambient pressure. For example, the enclosure 6100 and internal components of the RPT device 6000 may cooperate to form at least a portion the air flow path under negative pressure, effectively forming at least a portion of a pneumatic block that extends from the inlet (e.g., inlet tube array 6052) into the enclosure 6100 and to the blower inlet of the blower 6010. A positively pressurised airflow may be generated at the blower outlet of the blower 6010 and passed on to the outlet (e.g., outlet tube 6054) out of the enclosure 6100. A pneumatically sealed engagement between blower outlet and the inlet of the outlet tube 6054 may mean that the enclosure 6100 is isolated from the high pressure imparted by the blower 6010. However, in an alternative arrangement, characterised by the absence of a direct pneumatic seal between the blower outlet and the inlet of the outlet tube 6054, a respective portion of the enclosure 6100 may actually be exposed to the high pressure imparted by the blower 6010, e.g., the enclosure 6100 may form at least a portion of a chamber arranged to guide pressurized airflow from the blower outlet to the inlet of the outlet tube 6054.

Figures 1, 3B:
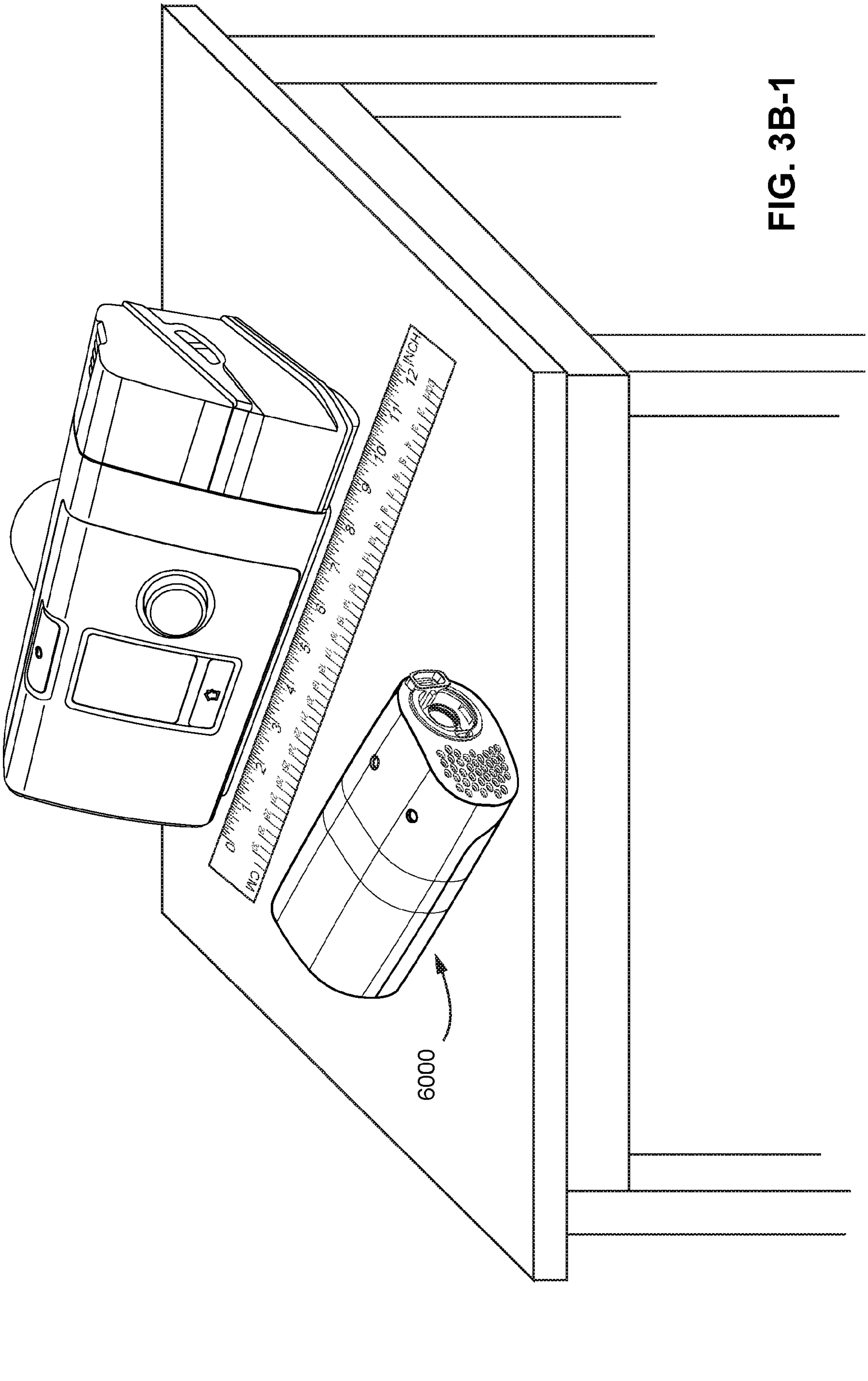
Figures 2, 3B:
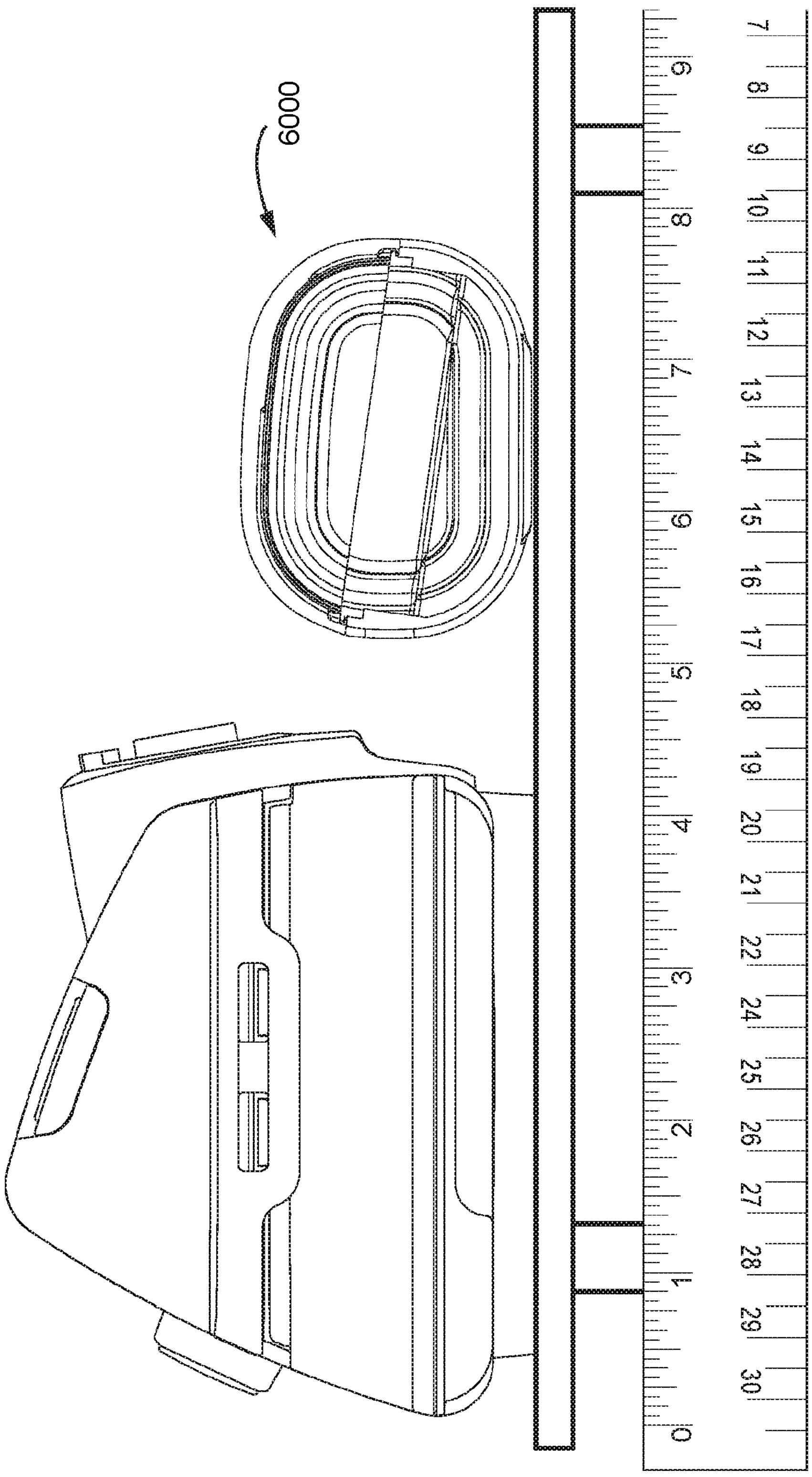
Figures 3, 3B:
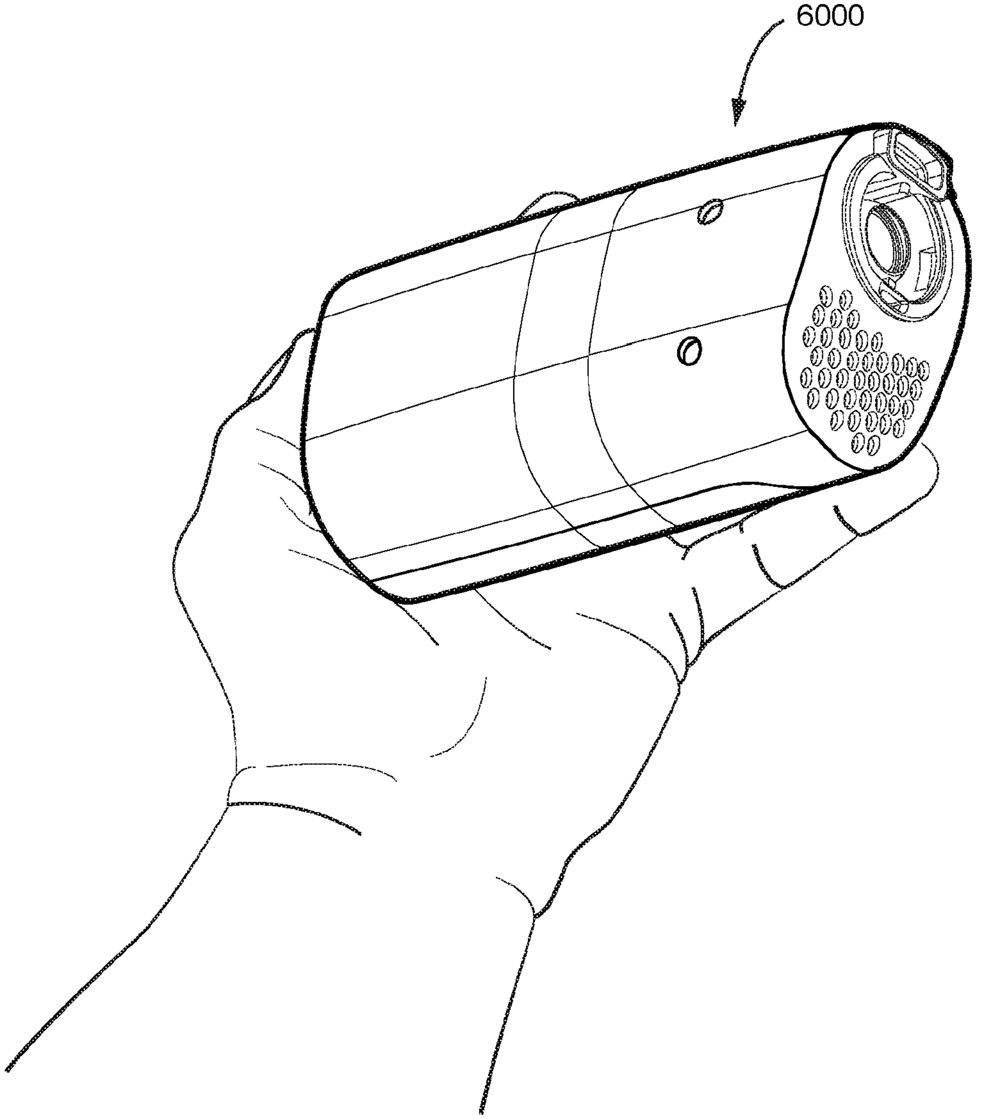
Figures 3, 3B, 4:
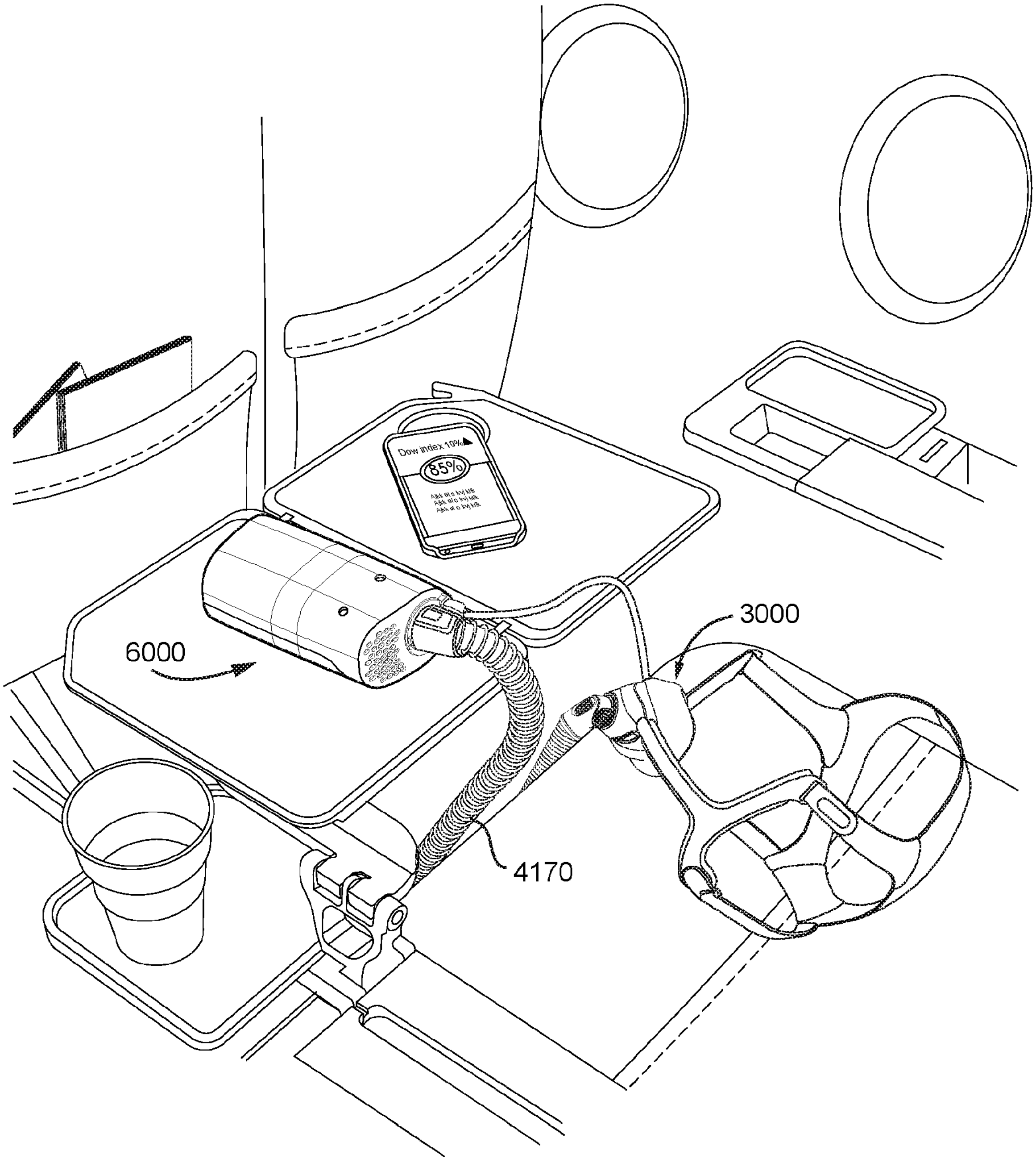
Figures 3, 3B, 4, 5:
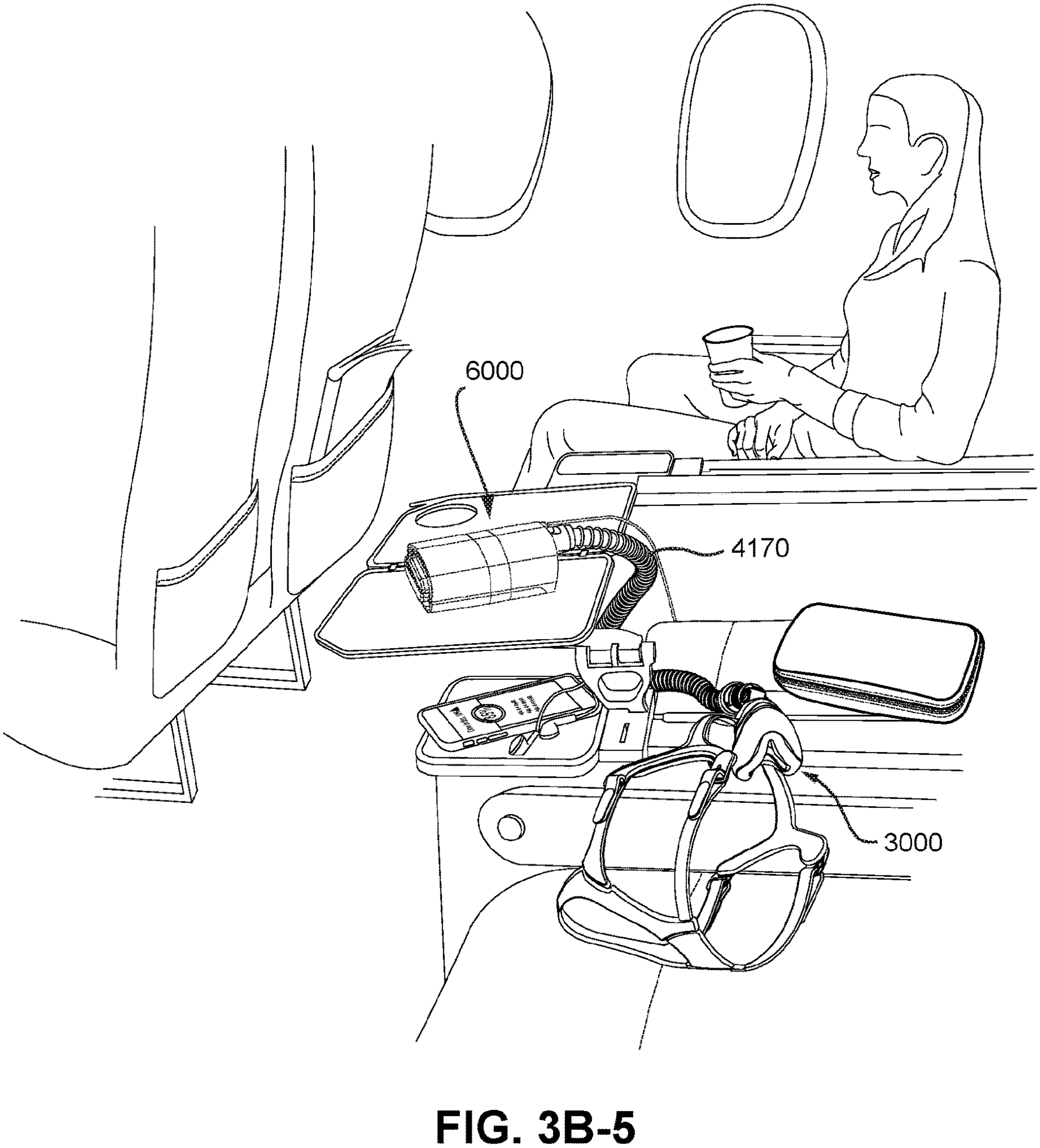

The RPT device 6000 is structured and arranged to reduce noise or sound output of the RPT device 6000 while maintaining a relatively small size. For example, as shown in FIG. 3B-3, the RPT device is small and light enough to allow the user to securely hold the device in a single hand. FIGS. 3B-1 and 3B-2 show size comparison between ResMed's AirSense 10 device and the RPT device 6000, which clearly illustrates the small and compact size of the RPT device 6000 which may be advantageous for travel (e.g., see FIGS. 3B-4 and 3B-5 showing the RPT device 6000 on a tray table of an airplane, which illustrates the size comparison to a smartphone), portability and useability around the house (e.g., can be used in the bedroom as shown in FIG. 1), easy manipulation for operational positioning/adjustment, etc. In an example, ResMed's AirSense 10 device is relatively quiet for use in the bedroom, but relatively large and cumbersome for travel (e.g., difficult and inconvenient to use in airplane). In contrast, ResMed's AirMini device is small and portable for travel, but relatively noisy (e.g., compared to ResMed's AirSense 10 device), which may be difficult for a patient to comply with therapy in the bedroom or a hospital. The RPT device 6000 according to an example of the present technology combines the benefits of the small compact size of ResMed's AirMini device with quietness similar to ResMed's AirSense 10 device (due to the noise reductions described herein) to provide a portable device that can be conveniently used anywhere, i.e., in the bedroom, in an airplane, etc. In addition, in the case where the enclosure 6100 is pressurised (positively and/or negatively), the RPT device 6000 is also arranged to be pneumatically sealed, so as to maintain this pressure. In an example, as shown in FIG. 3L, the interior of the enclosure 6100 may be subject to different pressures, e.g., ambient pressure at the inlet of the enclosure 6100, negative pressure (−P) along the interior flow path before the flow reaches the blower 6010 (i.e., at a negative pressure upstream of the blower), and positive or elevated pressure (+P) as the flow is pressurized within and at the outlet side of the blower 6010 (i.e., at a positive pressure downstream of the blower), between the blower outlet and the inlet of the outlet tube 6054.

In the illustrated example, the enclosure 6100 includes a first portion 6110 (an upper or top housing portion) and a second portion 6120 (a lower or bottom housing portion) that are connected or otherwise assembled to one another into an assembled configuration.

As described in greater detail below, the RPT device 6000 comprises a noise mitigating arrangement configured and arranged to reduce noise conducted or escaping through an air path (or air gap) at the joint or interface between the first portion 6110 and the second portion 6120 of the enclosure 6100 when in the assembled configuration. The noise mitigating arrangement may also be configured and arranged to reduce noise radiated by, or propagating through, one or more walls or joints of the RPT device. Although the noise mitigating arrangement is described herein with reference to an RPT device, it should be appreciated that aspects of the technology may be suitable for other applications.

Figure 3C:
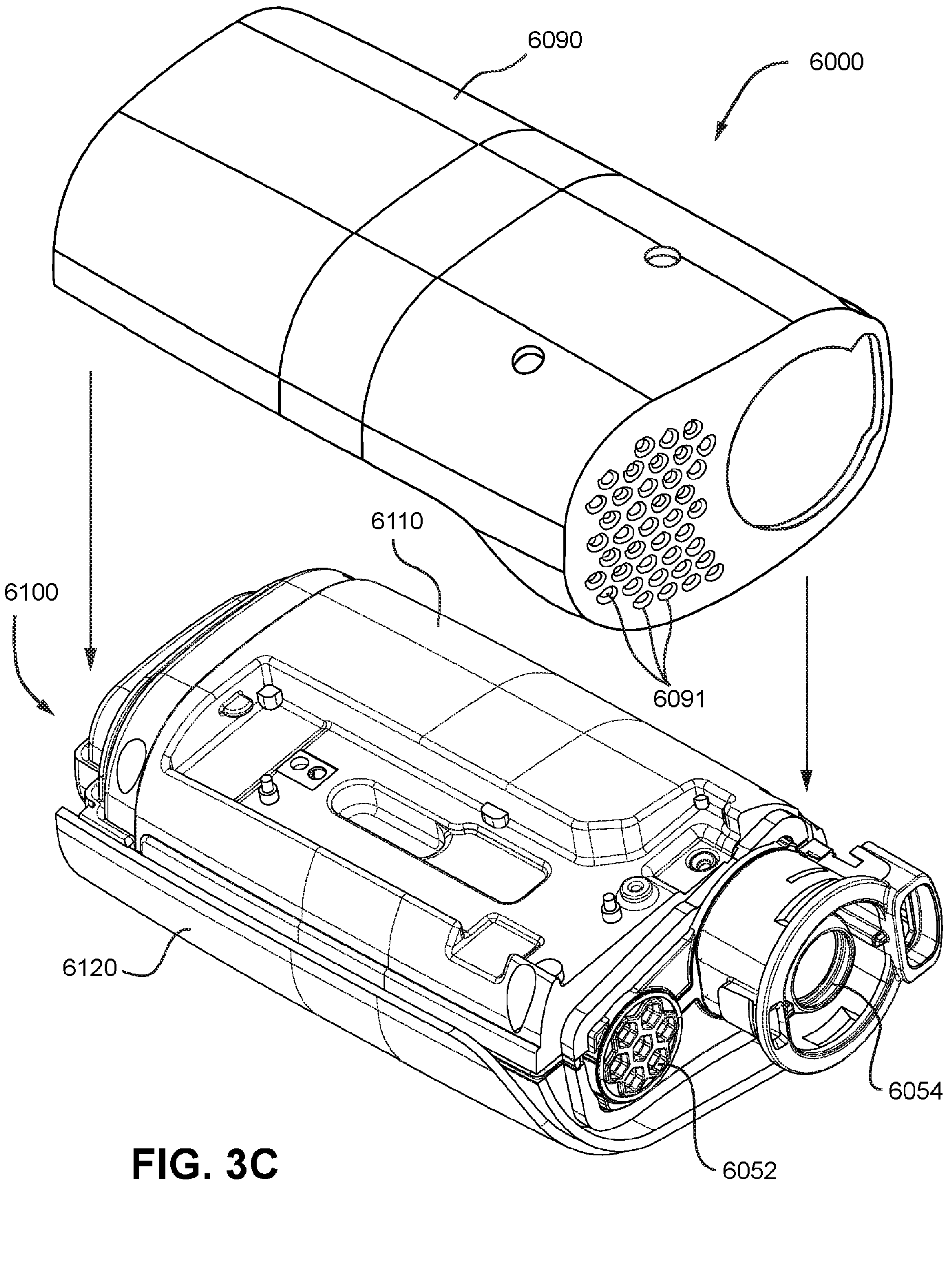
FIG. 3C is an exploded view of the RPT device of FIG. 3A showing a top case (6090) and an enclosure according to an example of the present technology.
Figure 3D:
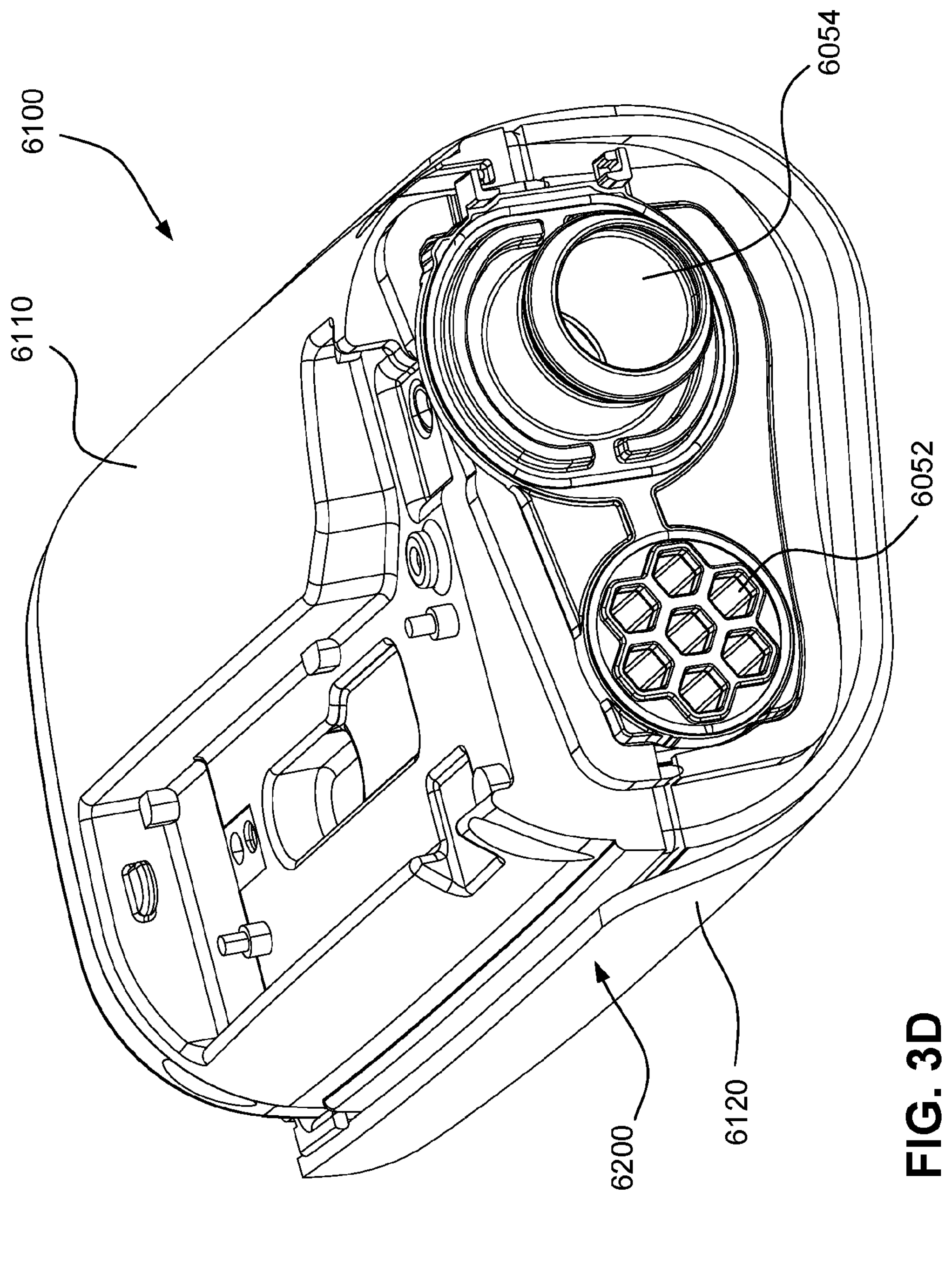
FIG. 3D is a perspective view showing the enclosure of the RPT device according to an example of the present technology.
Figure 3E:
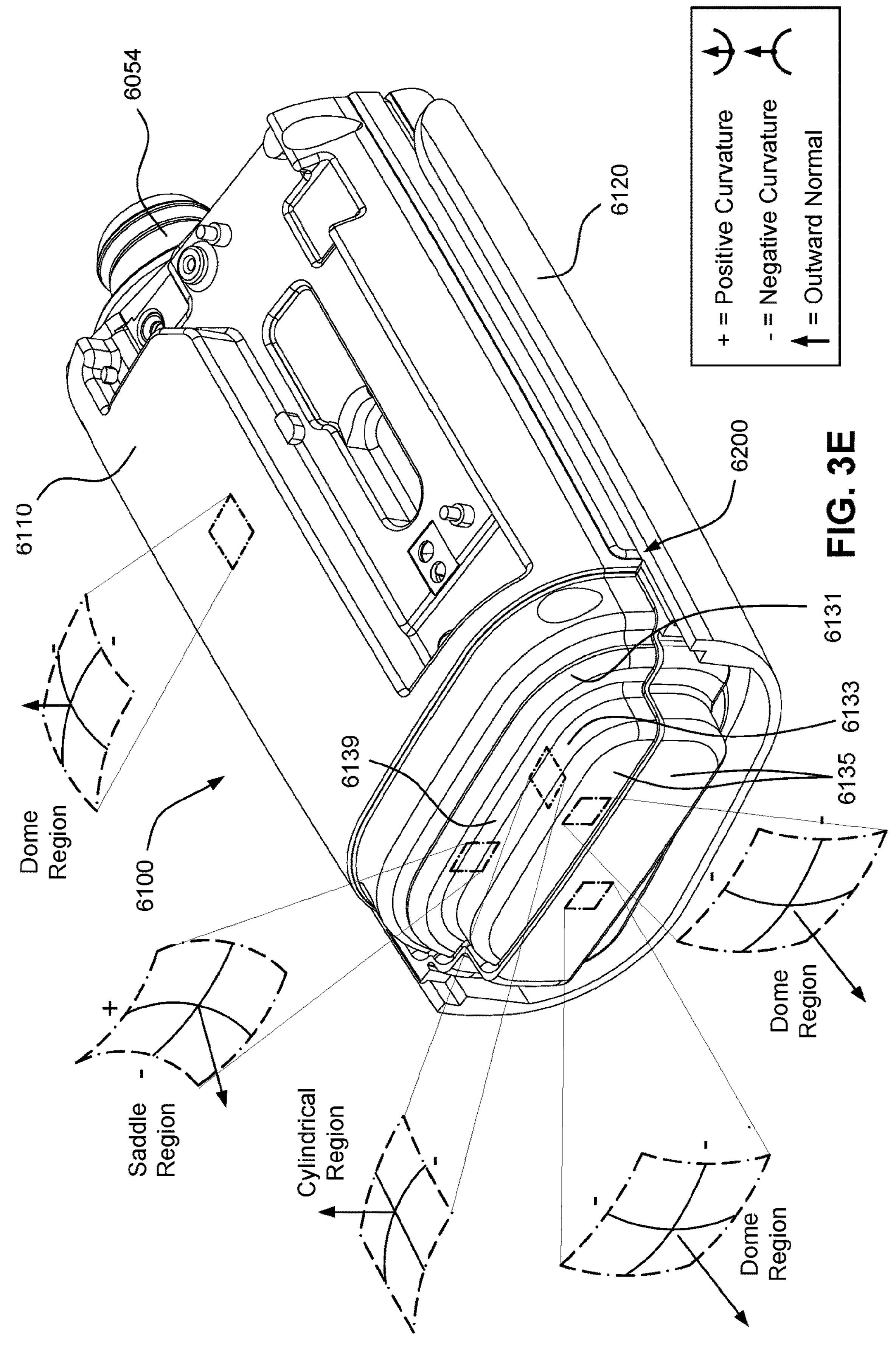
FIG. 3E is another perspective view of the enclosure of FIG. 3D.

In the illustrated example, as shown in FIGS. 3A to 3C, the RPT device 6000 comprises a second top case 6090 that is connected or otherwise assembled to at least partially cover the first portion 6110, thus forming an outer top surface of the enclosure 6100. In illustrated example, the second portion 6120 (the lower or bottom housing portion) of the enclosure 6100 may serve as a bottom case to both the upper portion 6110 and the top case 6090. Thus, the top case 6090 and the second portion 6120 may cooperate to form the external casing or external housing of the RPT device 6000 (see FIGS. 3A and 3B). In some examples, the upper portion 6110 may be of a more rigid construction and fulfil various supporting and sealing functions, whilst the top case 6090 may be less rigid and fulfil a somewhat cosmetic function. In such instances, the top case 6090 may also be referred as "fascia". In an example, the top case 6090 may also function as at least a secondary acoustic insulator, as there may or may not be specific sound proofing on its interface perimeter with the enclosure 6100. For example, the top case 6090 may comprise an overmold constructed of a relatively soft material (e.g., a rubber such as TPE or silicone) on interior and/or exterior surfaces thereof, to provide specific sound damping and/or tactile properties. TPE may have certain advantages over silicone in terms of reducing radiated noise.

In an example, a printed circuit board assembly (PCBA) and/or one or more user interfaces may be supported within an interior space formed between the top case 6090 and the first portion 6110 of the enclosure 6100, i.e., PCBA is exterior to the air flow path. In some cases, the PCBA may be attached to and supported by the first portion 6110.

In an alternative example, a separate top case 6090 may not be provided. In such example, the first portion 6110 (an upper or top housing portion) may in the form of a top case so the first and second portions 6110, 6120 cooperate to form the external casing or external housing of the RPT device 6000.

5.4.1 RPT Device Mechanical & Pneumatic Components

An RPT device may comprise one or more of the following components in an integral unit. In an alternative form, one or more of the following components may be located as respective separate units.

5.4.1.1 Enclosure

In the illustrated example, the first portion 6110 comprises one or more first wall portions 6112 that form one or more portions of the top, side(s) and/or end(s) of the enclosure 6100, e.g., a top wall portion, opposing side wall portions, and an end wall portion (e.g., see FIGS. 3N-3 and 3S to 3W).

As illustrated, the first wall portion 6112 of the first portion 6110 of the enclosure 6100, includes a first interior surface 6114, a first exterior surface 6116 and a first intermediate surface 6118 located between the first interior surface 6114 and the first exterior surface 6116 (e.g., see FIGS. 3N-3 and 3S to 3W). In an example, the PCBA and/or one or more user interfaces (e.g., button (e.g., power button, wireless connection button), switch, dial, display) may be mounted or otherwise supported by the first portion 6110. For example, the PCBA and/or one or more user interfaces may be supported on the first exterior surface 6116 (e.g., outside the air flow path of the enclosure 6100 which is under pressure in use). Alternatively, the PCBA and/or one or more user interfaces may be supported within the interior of the enclosure and protrude through one or more openings in the first portion 6110.

In the illustrated example, the second portion 6120 comprises one or more second wall portions 6122 that form one or more portions of the bottom, side(s) and/or end(s) of the enclosure 6100, e.g., a bottom wall portion, opposing side wall portions, and an end wall portion (e.g., see FIGS. 3N-3 and 3S to 3T).

As illustrated, the second portion 6120 of the enclosure 6100 includes a second interior surface 6124, a second exterior surface 6126 and a second intermediate surface 6128 located between the second interior surface 6124 and the second exterior surface 6126 (e.g., see FIGS. 3N-3 and 3S to 3T).

Figure 3F:
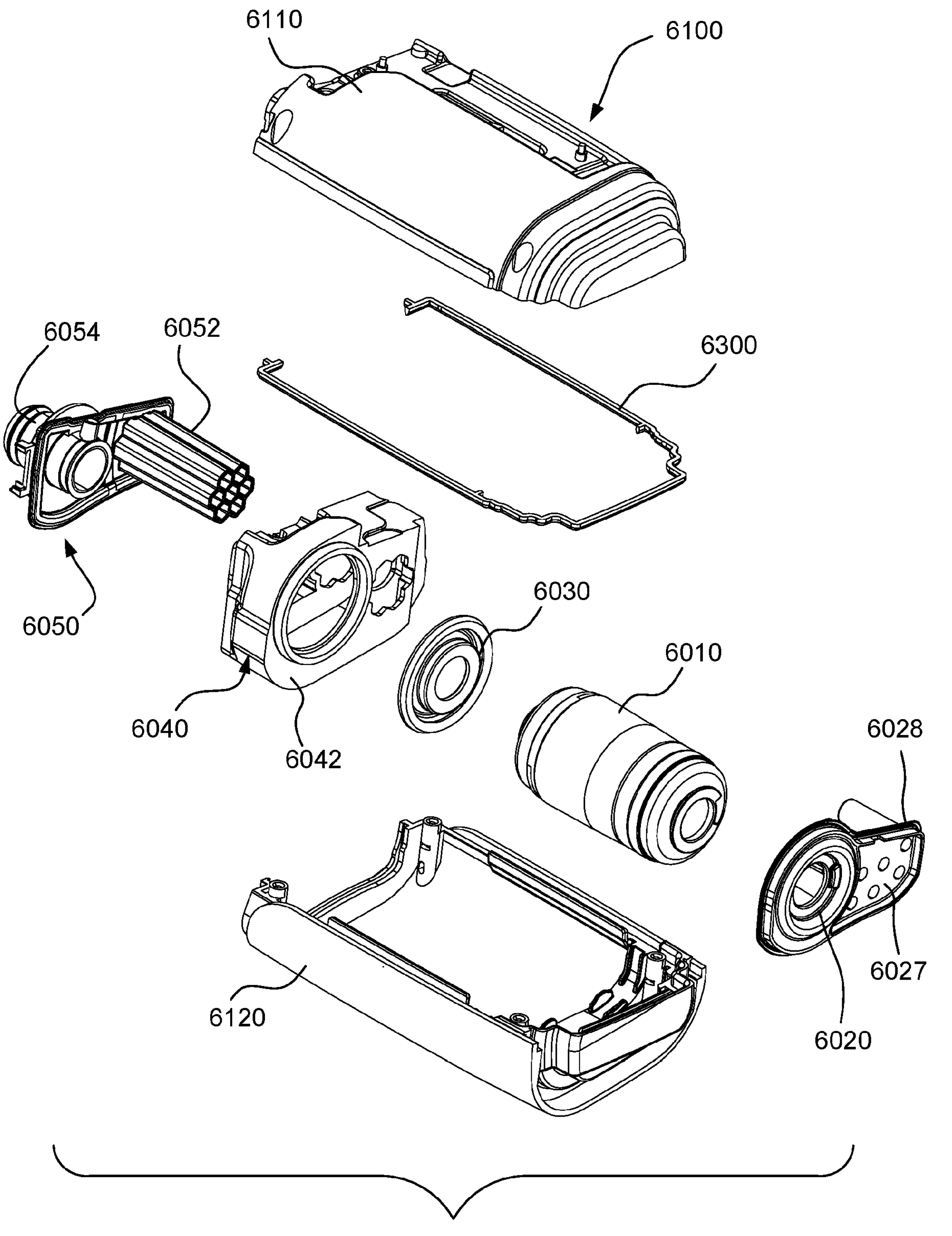
FIG. 3F is an exploded view showing the enclosure and internal components of the RPT device according to an example of the present technology.
Figure 3G:
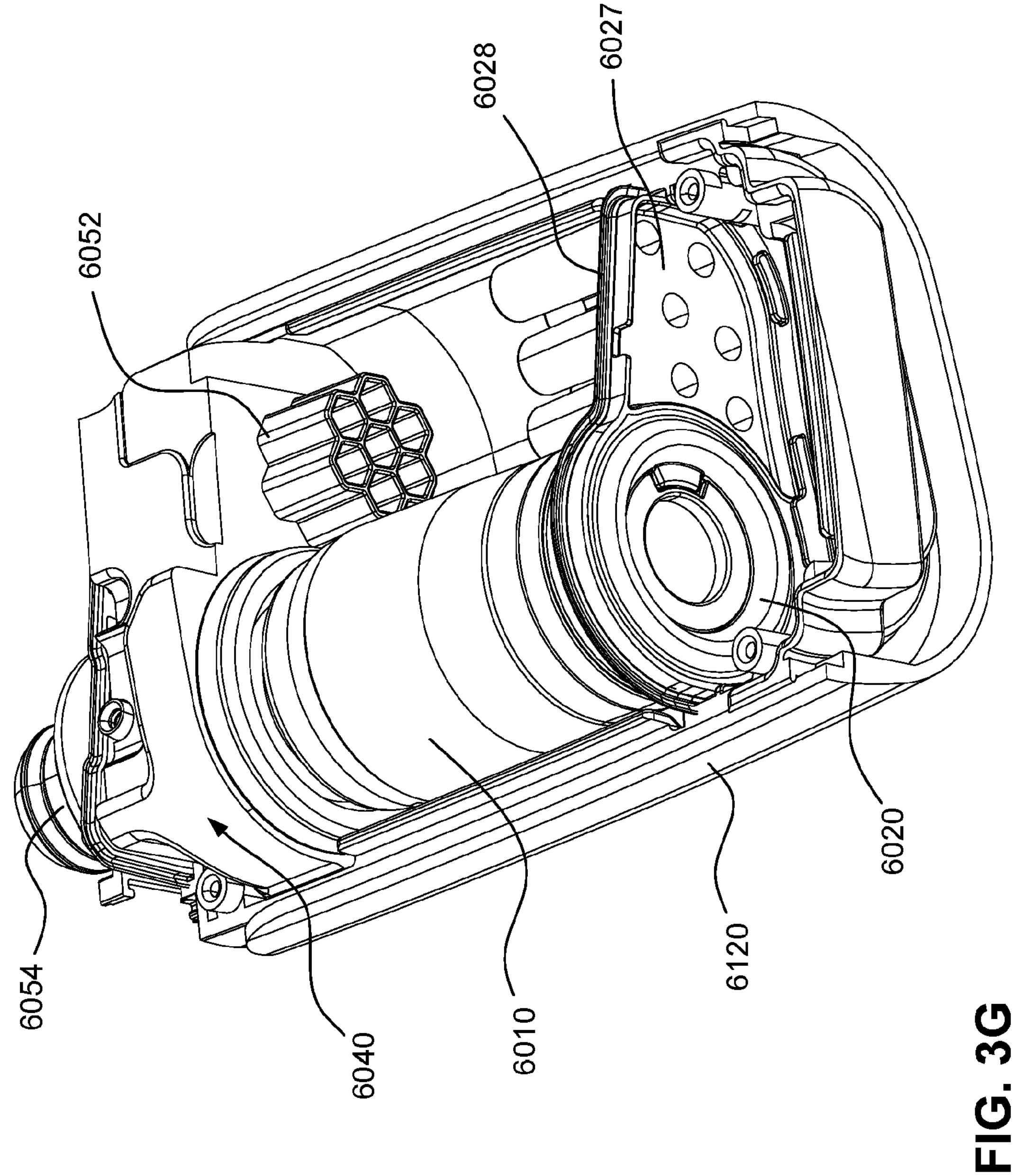
FIG. 3G is a perspective view showing internal components of the RPT device within a lower portion of the enclosure, with an upper portion of the enclosure removed, according to an example of the present technology.
Figure 3H:
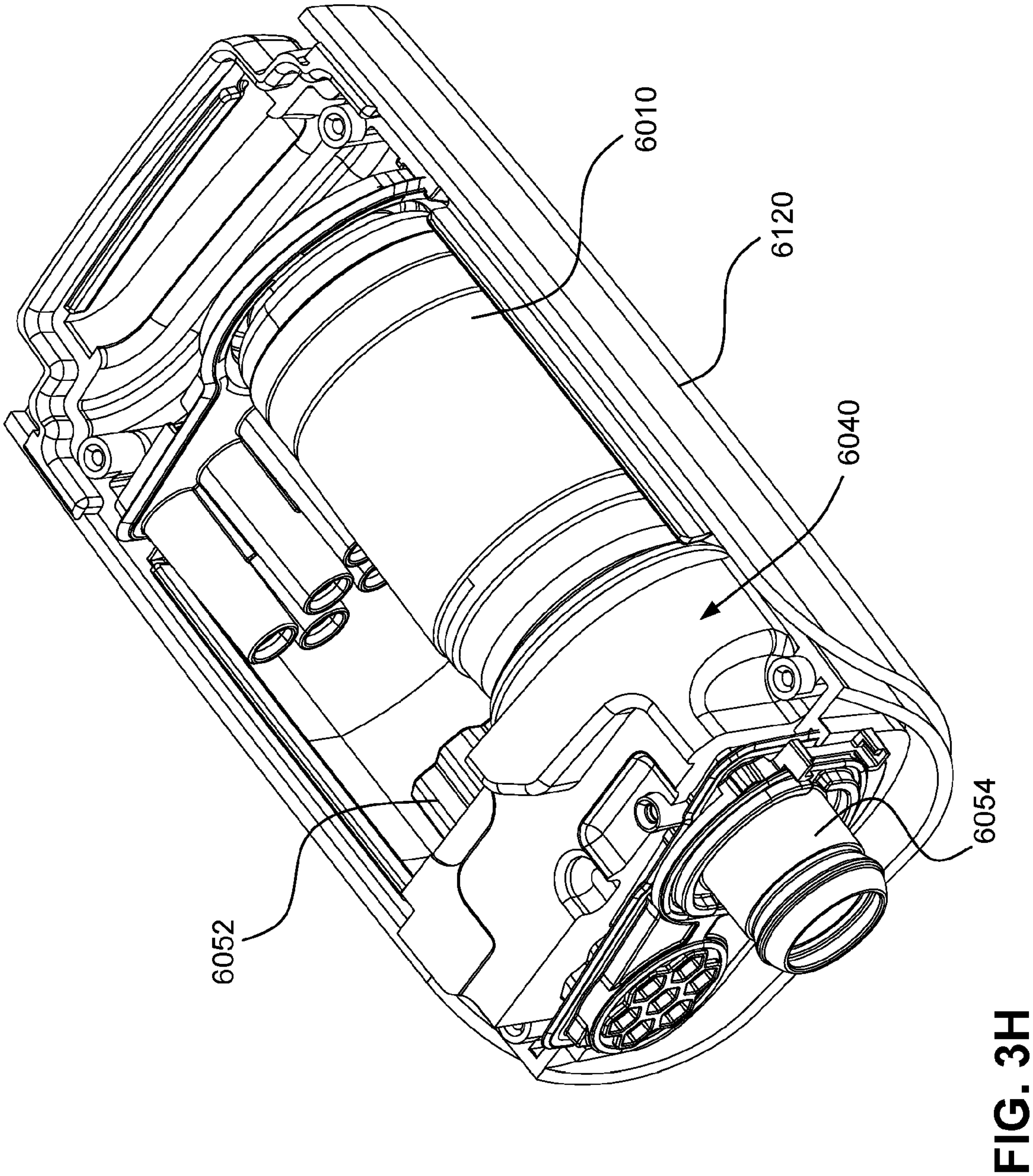
FIG. 3H is another perspective view of the internal components of the RPT device within a lower portion of the enclosure of FIG. 3G.
Figure 3I:
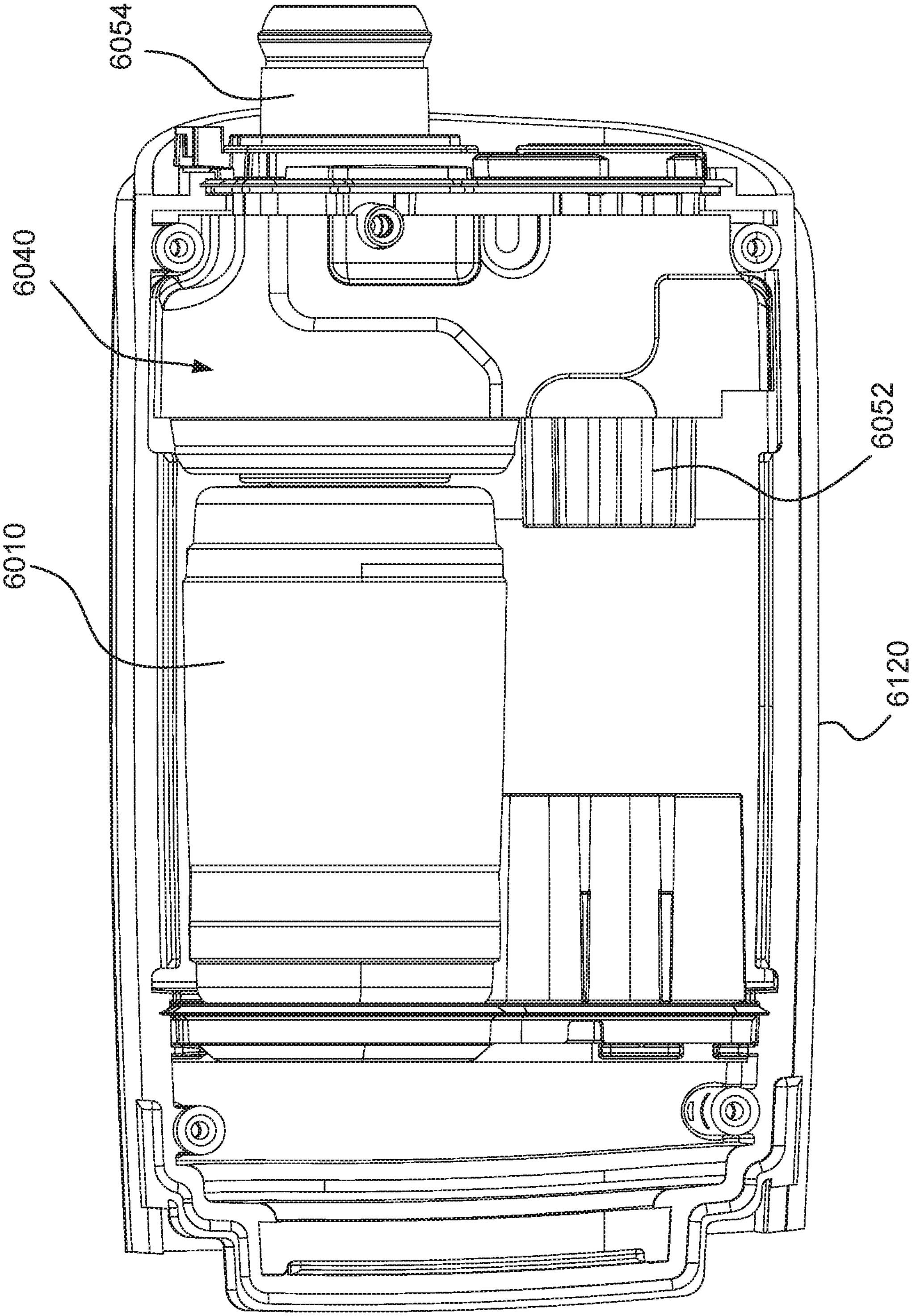
FIG. 3I is a top view showing internal components of the RPT device within a lower portion of the enclosure, with an upper portion of the enclosure removed, according to an example of the present technology.
Figure 3J:
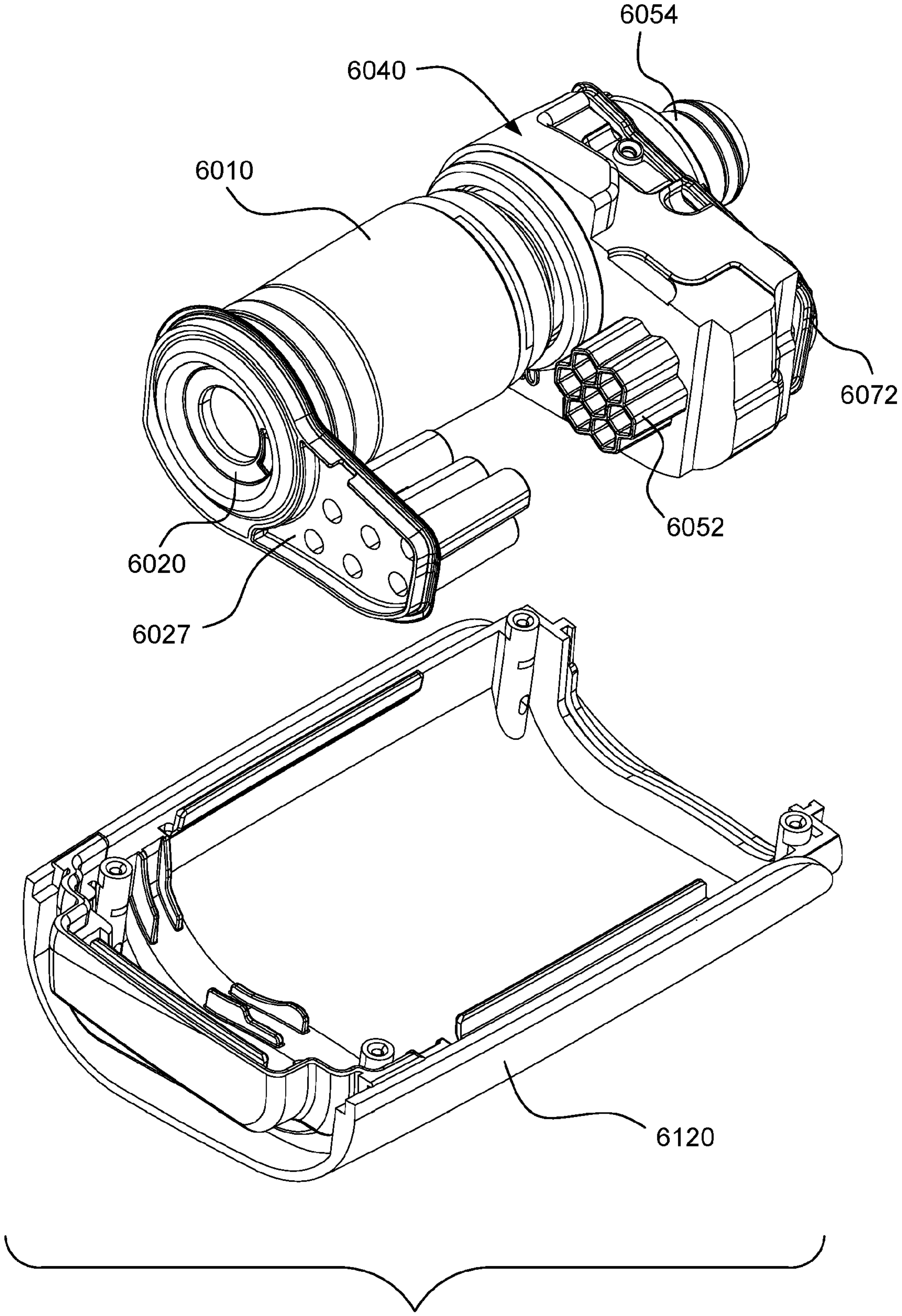
FIG. 3J is an exploded view showing internal components of the RPT device and a lower portion of the enclosure according to an example of the present technology.
Figure 3L:
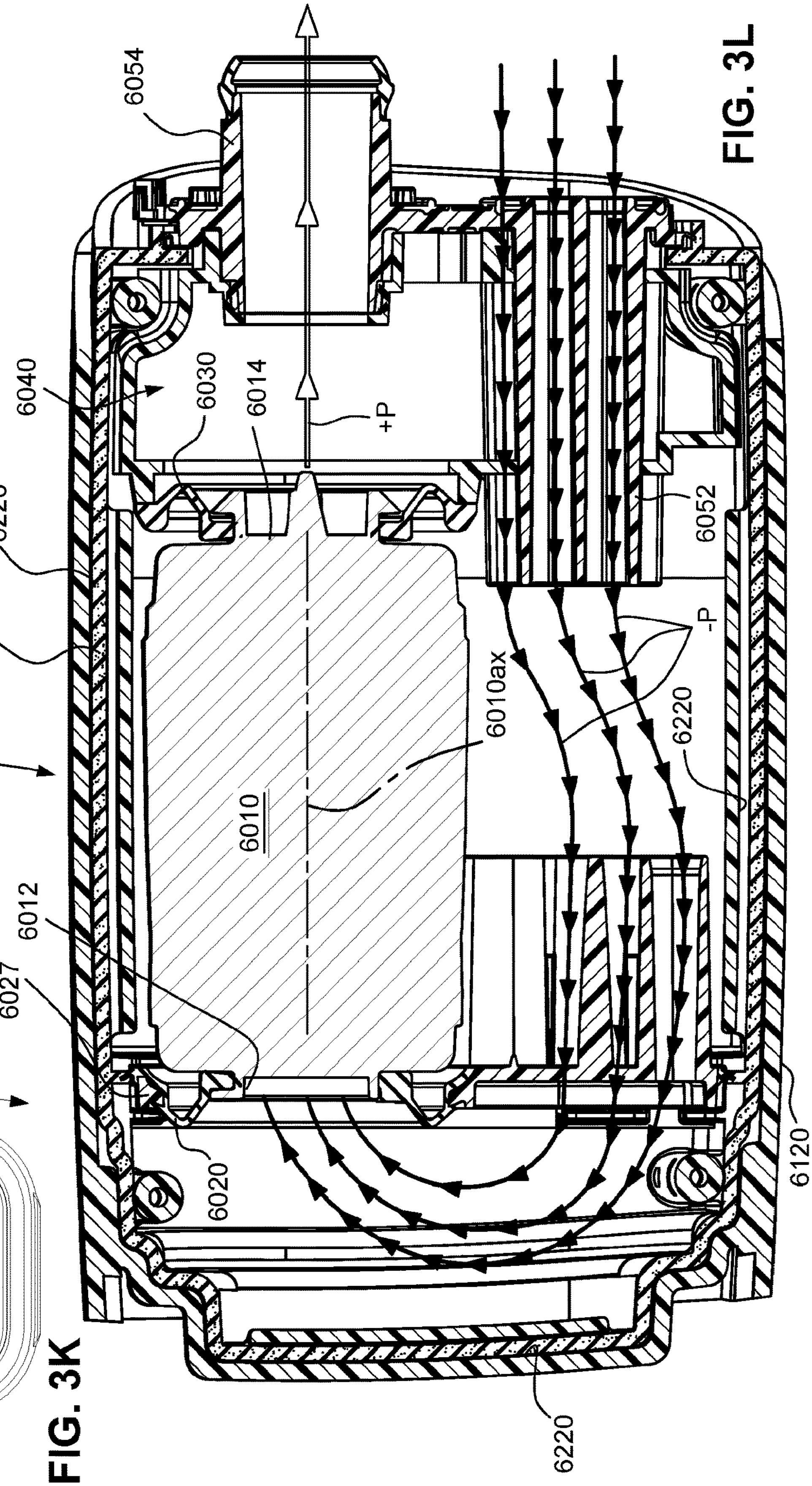
FIG. 3L is a cross-sectional view through line 3L-3L of FIG. 3K.
Figure 3K:
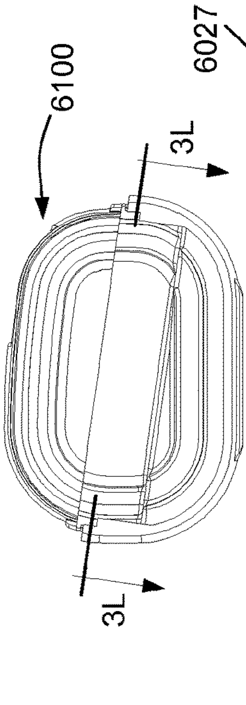
FIG. 3K is an end view of the enclosure of FIG. 3E. A further cover may be included on the illustrated end.
Figure 3N:
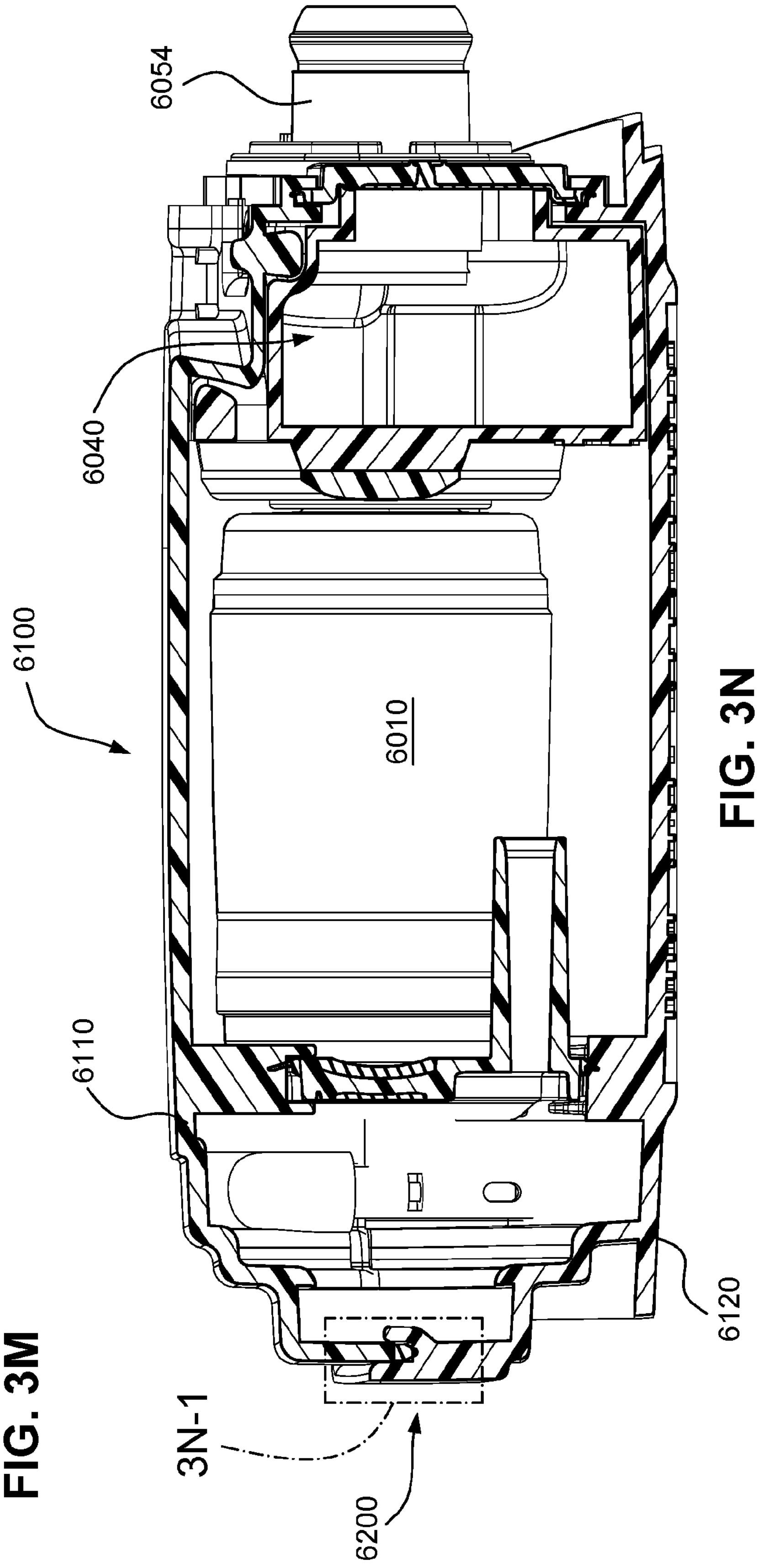
FIG. 3N is a cross-sectional view through line 3N-3N of FIG. 3M.
Figure 3M:
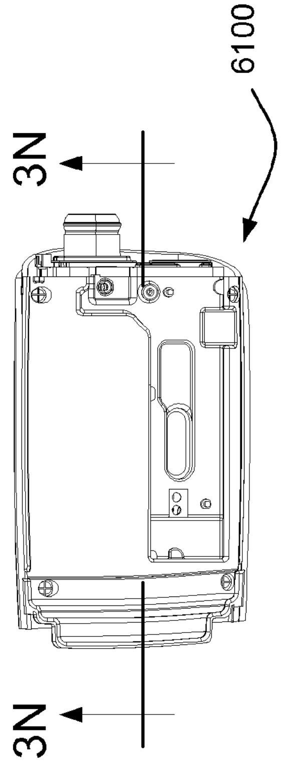
FIG. 3M is a top view of the enclosure of FIG. 3E.
Figures 2, 3N:
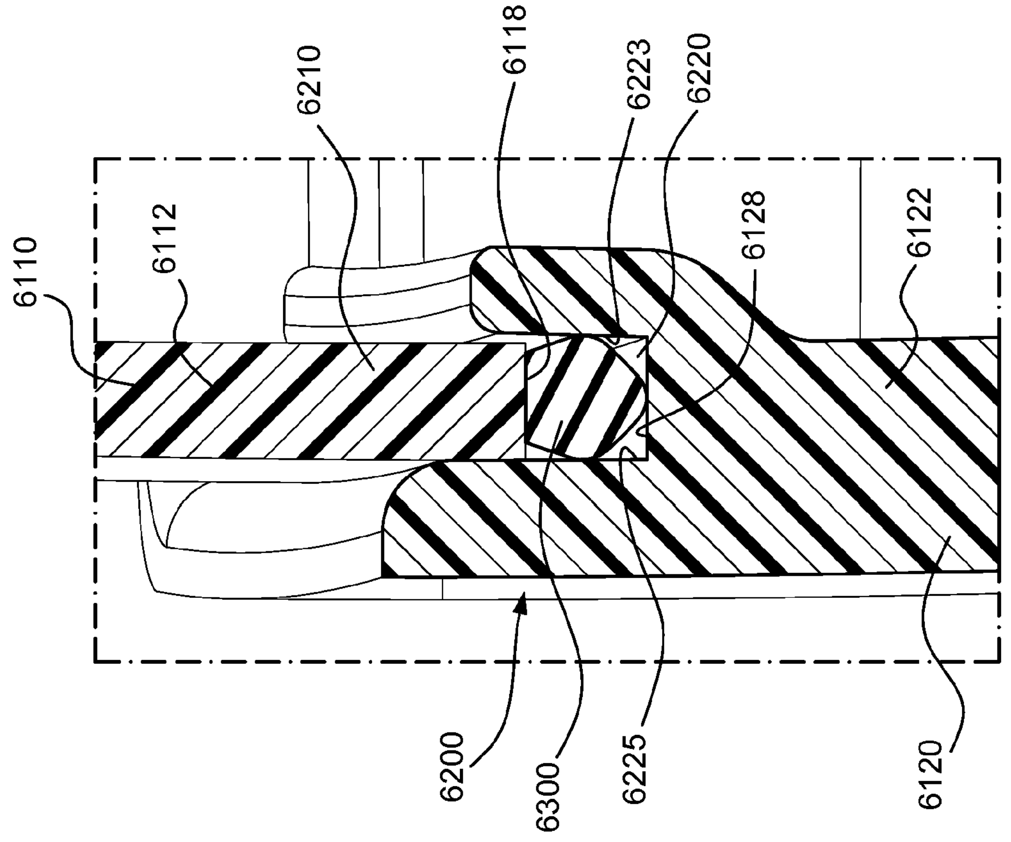
Figures 1, 3N:
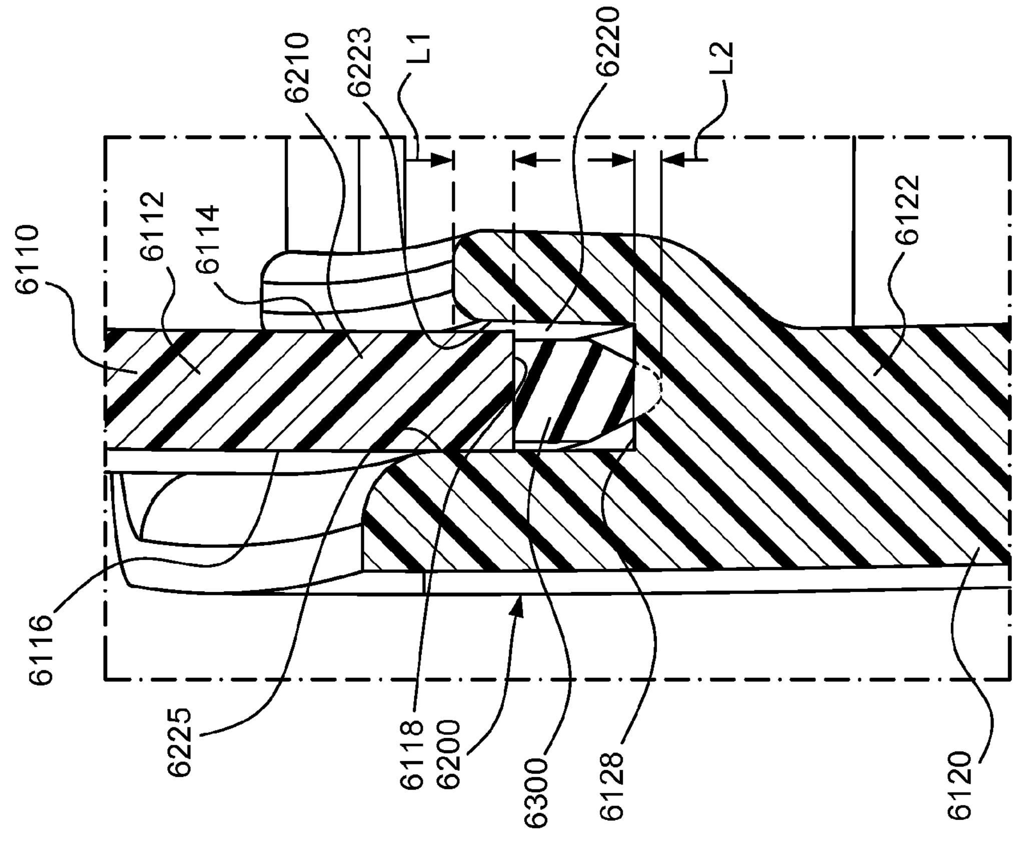
Figures 3, 3N, 4:
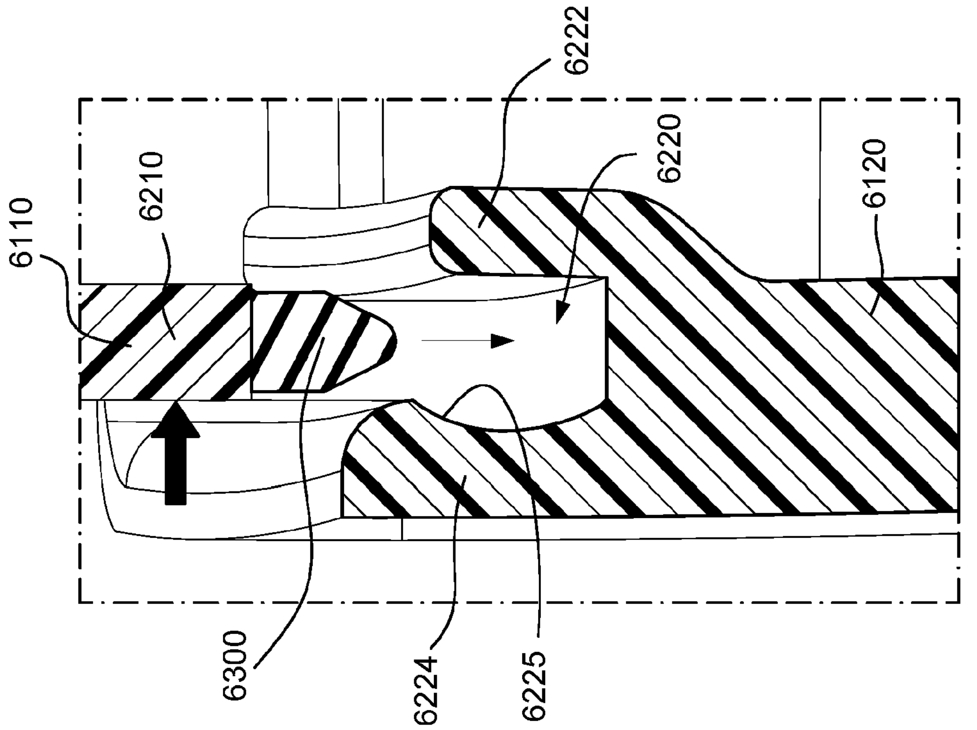
Figures 3, 3N:
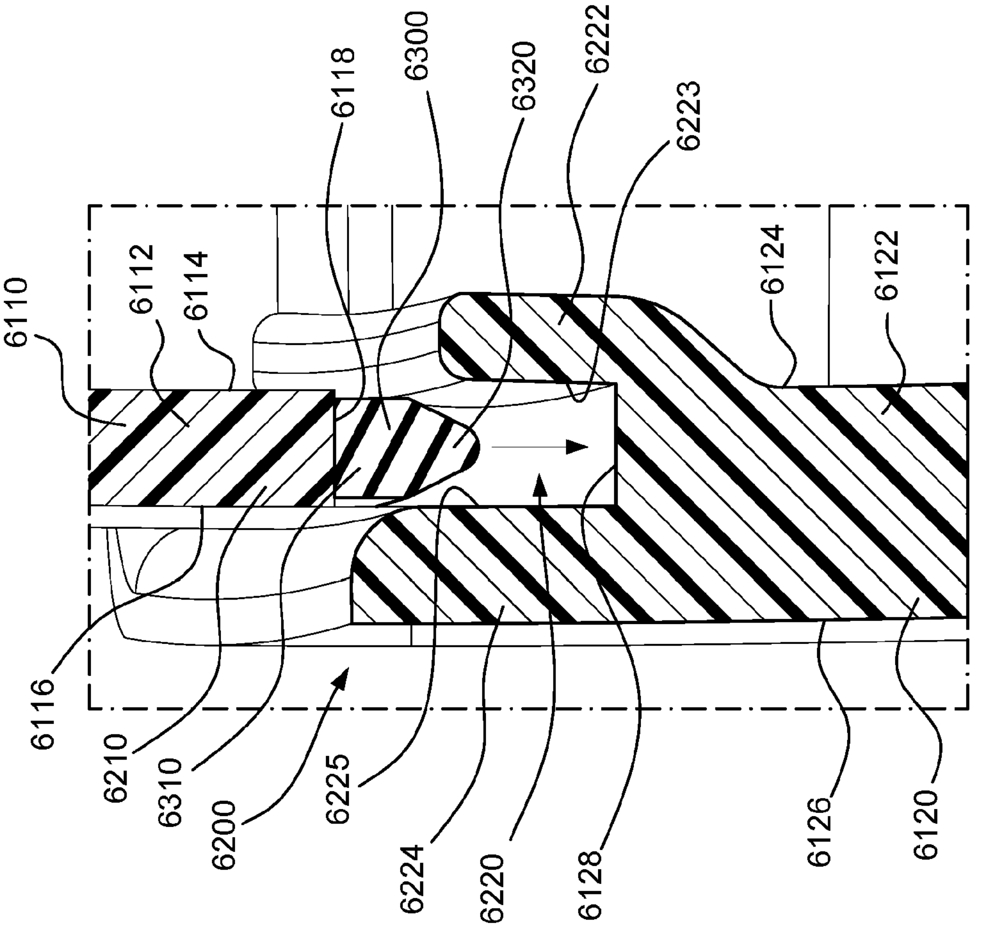

In the illustrated example, the first portion 6110 is assembled to the second portion 6120 so that one or more first wall portions 6112 are assembled adjacent one or more second wall portions 6122 in an assembled configuration (e.g., see FIGS. 3N-1 and 3N-2). A noise mitigating arrangement is provided to the enclosure 6100 to reduce conducted noise through an air path (or air gap) at the joint or interface between adjacent first and second wall portions when in the assembled configuration.

In the illustrated example, the noise mitigating arrangement comprises a wall constrainment arrangement 6200 and a seal 6300, e.g., a gasket. As described in greater detail below, the wall constrainment arrangement 6200 is configured and arranged to constrain or limit lateral movement of the first portion 6110 and the second portion 6120 (e.g., constrain lateral movement (i.e., see arrows L,R in FIG. 3P) of the first wall portion 6112 and the second wall portion 6122 when in an assembled configuration), and the seal 6300, e.g., gasket, is configured and arranged to form a seal between mating surfaces of the first portion 6110 and the second portion 6120 in the assembled configuration. As shown in FIG. 3F, the seal 6300, e.g., gasket, can be a separate component. However, the seal, e.g., gasket, may also be overmolded onto either the periphery of the first portion 6110 or the periphery of the second portion 6120. Alternatively, a portion of the seal, e.g., gasket, may be overmolded onto the periphery of the first portion 6110 and a portion of the seal, e.g., gasket, may be overmolded onto the periphery of the second portion 6120.

In an example, the wall portions of the first portion 6110 and the second portion 6120 each comprise a relatively rigid material (e.g., polypropylene). As would be discussed further in the text, the seal 6300, e.g., gasket, can comprise a resiliently flexible or deformable material (e.g., viscoelastic material, TPE, TPU, TPV). In an example, an overmold constructed of a relatively soft material (e.g., TPE or silicone) may be provided (e.g., by overmolding) to interior and/or exterior surfaces of one or more wall portions of the first portion 6110 and/or the second portion 6120 to provide damping properties for attenuating wall-radiated noise. Also, the rigidity or stiffness of wall portions of the first portion 6110 and/or the second portion 6120 may be controlled to dampen radiated noise.

Wall Constrainment Arrangement

In one example, the wall constrainment arrangement 6200 comprises a tongue and groove engagement arrangement between the first portion 6110 and the second portion 6120 along at least a portion of the engagement perimeter or engaged peripheral edge (i.e., along at least a portion of the joint or interface between adjacent first and second wall portions when in the assembled configuration).

In this example, the first portion 6110 comprises the tongue 6210 of the tongue and groove engagement arrangement, and the second portion 6120 comprises the groove 6220 of the tongue and groove engagement arrangement (e.g., see FIG. 3N-3). However, in an alternative example, the positions of the tongue and the groove may be reversed, i.e., the second portion 6120 may comprise the tongue and the first portion 6110 may comprise the groove. In a further alternative example, each of the first and the second portions 6110 and 6120 may include both tongue portions and groove portions, arranged for engagement with respective groove portions and tongue portions of the opposing portion.

In the illustrated example, the tongue 6210 is provided along the entire periphery of the peripheral edge of the first portion 6110, and the groove 6220 is provided to selected portions along the periphery of the peripheral edge of the second portion 6120. That is, in the illustrated example, the groove 6220 does not extend continuously along the periphery of the second portion 6120, i.e., the groove 6220 is distributed in sections along the periphery (e.g., groove provided to each of opposing side wall portions and one of the end wall portions of the second portion 6120 as shown in FIGS. 3L, 3S and 3T). However, it should be appreciated that the groove may be distributed along the periphery in other suitable manners. Moreover, in alternative examples, it should be appreciated that the groove may extend continuously along the entire peripheral edge of the second portion 6120. Likewise, in alternative examples, it should be appreciated that the tongue may be provided to the periphery of the first portion in other suitable manners, e.g., one or more tongues provided to one or more selected portions of the first portion 6110 along its periphery.

When the first and second portions 6110, 6120 are in an assembled configuration, the tongue 6210 is engaged within the groove 6220 so that lateral movement of the tongue 6210 is constrained on both sides along at least the engaged portion of the peripheral edge of the first and second portions 6110, 6120.

The tongue 6210 is arranged at the peripheral edge or free end of the first portion 6110, and provides the first intermediate surface 6118 between the first interior surface 6114 and the first exterior surface 6116 (e.g., see FIG. 3N-3). The groove 6220 is arranged at the peripheral edge or free end of the second portion 6120. The groove 6220 is formed by two side walls 6222, 6224, and provides second intermediate surface 6128, inner side wall surface 6223, and outer side wall surface 6225 (e.g., see FIG. 3N-3). In this example, the two intermediate surfaces 6118 and 6128 extend generally horizontally (this is to say that they are substantially parallel to the flat horizontal supporting surface BP on which the RPT device 6000 would generally be positioned in its standard operational configuration (i.e. FIG. 3P)), whilst the inner and outer side wall surfaces would be generally vertical (they are substantially transverse to the flat horizontal surface on which the RPT device 6000 would generally be positioned in its standard operational configuration). Because of this orientation, when the first and second portion are brought together and fastened to each other, usually by way of screws, the tightening of the screws applies a pressure force that is transverse to the intermediate surfaces and brigs them into an abutment engagement with each other. The seal 6300, e.g., gasket, is compressed between intermediate surfaces 6118 and 6128, effecting a compression acoustic and/or pneumatic seal between them and between the first and the second portions 6110 and 6120.

In the illustrated example, one of the side walls 6222, 6224 of the groove 6220 may be longer and/or thicker than the other of the side walls 6222, 6224 of the groove 6220, e.g., outer side wall 6224 may be longer and thicker than the inner side wall 6222 as shown in FIG. 3N-3. Such an arrangement may provide an increased support in an outward lateral direction. However, it should be appreciated that the side walls of the groove may include similar lengths and/or thicknesses.

In the assembled configuration, the lateral constraint is effected by way the first exterior surface 6116 of the tongue 6210 engaging the surface 6225 of the outer side wall of the groove 6220 and/or the first interior surface 6114 of the tongue 6210 engaging the surface 6223 of the inner side wall of the groove 6220 along at least a portion of the engaged peripheral edge (e.g., see FIGS. 3N-1 and 3N-2). Because of this engagement, lateral movement of each of the tongue and the groove, and consequently the lateral movement of the engaged peripheral edge, is constrained on both sides. Furthermore, any friction arising from the seal 6300 being compressed between surfaces 6128 and 6118 will improve lateral constrainment. In an example, the tongue 6210 and the groove 6220 may be configured and dimensioned (e.g., tolerances tightly controlled) so that one or both sides of the tongue are directly engaged with the sides of the groove when in the assembled configuration, i.e., the first exterior surface 6116 of the tongue 6210 engages the outer side wall surface 6225 of the groove 6220 and/or the first interior surface 6114 of the tongue 6210 engages the inner side wall surface 6223 of the groove 6220 along at least a portion of the engaged peripheral edge in the assembled configuration.

In an example, the tongue and groove engagement arrangement is such that, in an assembled configuration, at least 1 to 5 mm (e.g., 2 to 3 mm) of the tongue 6210 is received within the groove 6220, which provides sufficient depth of overlap of the tongue 6210 with the side walls 6222, 6224 of the groove 6220 for constrainment (e.g., see overlap length L1 in FIG. 3N-1).

In an example, the side walls 6222, 6224 of the groove 6220 fit tightly on both sides of the tongue, the minimised gap and the appreciable depth overlap between the tongue and groove creating a tortuous path for sound waves propagating through the tongue and groove engagement arrangement (no direct line of sight or path for noise). Also, the tight tolerance with which the side walls of the groove enclose or overlap the tongue from both sides, can reduce twisting and wall deformation. The rigidity of the tongue and groove engagement arrangement secures the first and second portions 6110, 6120 together (at least laterally), potentially providing self-retention, a rigid composite structure (assists with case stiffness and hence reduces radiated noise), and reduced likelihood of rattling under vibration.

In an example, one or both of the side walls of the groove 6220 may include an undercut or inward taper/curvature adapted to engage the tongue 6210. For example, the outer side wall surface 6225 of the outer side wall 6224 of the groove 6220 may be in the form of an inverted trapezoid and/or be slightly rounded to enhance engagement with the tongue 6210, thereby enhancing rigidity/stiffness of the enclosure. That is, as shown in FIG. 3N-4, the slightly rounded inner surface 6225 of the outer side wall 6224 of the groove provides a sort of spring-load so that the first portion 6110 with the tongue 6210 is flexed inwardly or squished (or compressed) to assemble the tongue 6210 into the groove 6220, and the biased tongue and groove engagement retains the first and second portions 6110, 6120 together so that they vibrate together and there is no secondary rattling noise of them vibrating against one another (i.e., overall less vibration). Thus, in some embodiments, the undercut/taper/curvature ensures that, upon insertion of the tongue 6210, only a limited portion of the surface 6225 is abuttingly engaged with a respective surface of the tongue 6210, thus minimising the friction between both surfaces, whilst ensuring the constrainment of the tongue-and-groove arrangement.

In an example, the lateral movement may be constrained continuously for the length of the engaged edge. In an alternative example, constrainment of the lateral movement may be distributed along the length of the engaged edge, e.g., tongue and groove arrangement provided in spaced apart segments (e.g., spaced apart teeth engageable within respective spaced apart grooves).

Figure 3P:
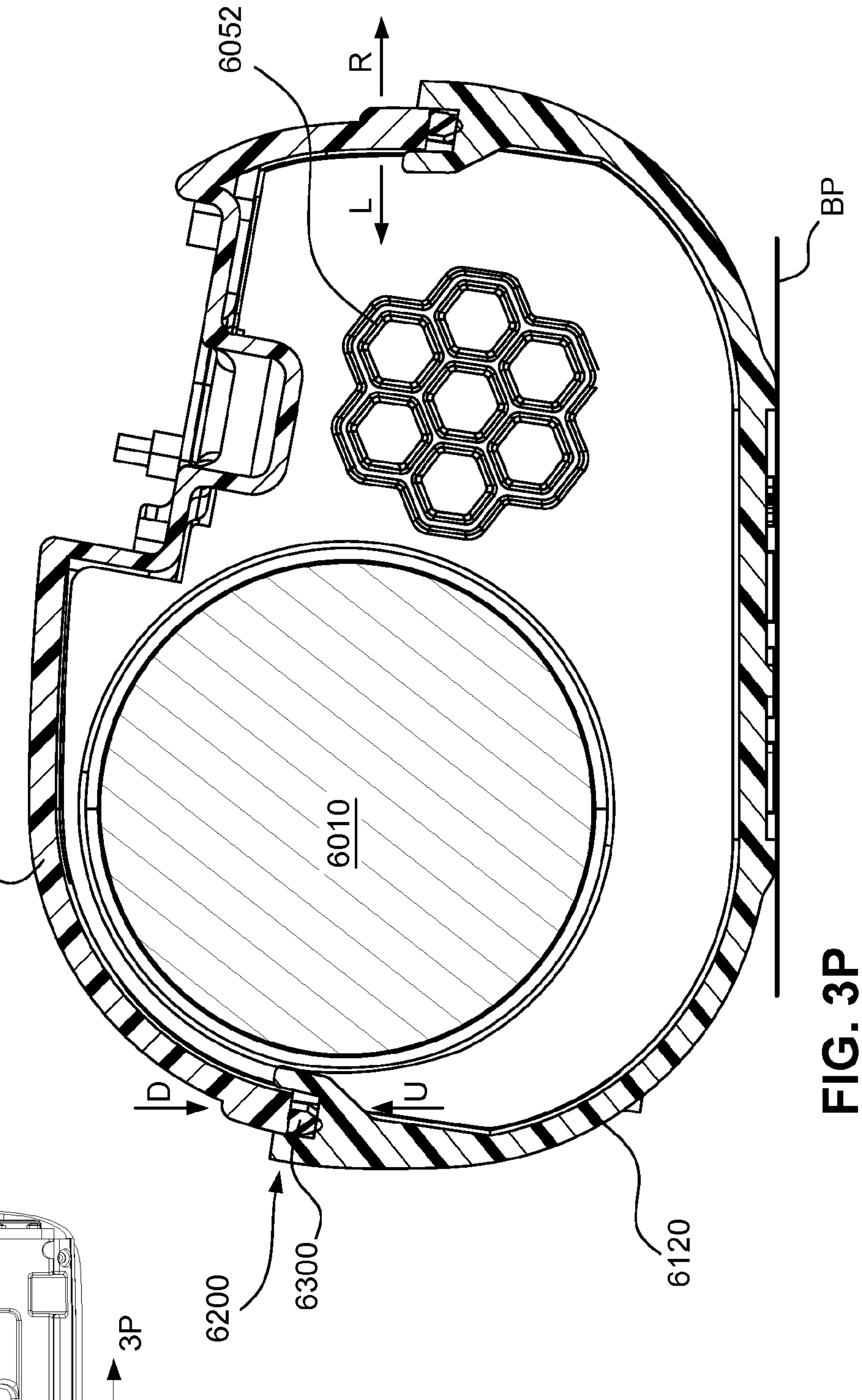
FIG. 3P is a cross-sectional view through line 3P-3P of FIG. 3O.
Figure 3O:
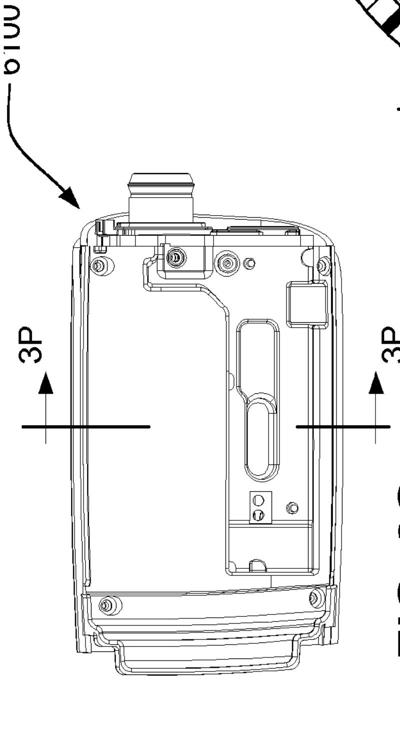
FIG. 3O is a top view of the enclosure of FIG. 3E.

In the illustrated example, the bottom of the enclosure 6100 (e.g., the bottom wall portion of the second portion 6120) includes a bottom surface defining a bottom plane BP that is substantially horizontal when the RPT device 6000 is in a normal, operational orientation (e.g., see FIG. 3P). In reference to FIG. 3P, the tongue and groove engagement arrangement is configured and arranged to constrain lateral movement of the first wall portion of the first portion 6110 and the second wall portion of the second portion 6120, which lateral movement is related to movement extending generally in a direction that is parallel to the bottom plane BP, i.e., left L and right R as viewed in FIG. 3P (e.g., sideways or horizontally towards and away from the interior of the enclosure). It should be appreciated that such constrainment of lateral movement is not limited to movement only extending generally in a direction that is parallel to the bottom plane, but may be slightly askew or angled relative to the bottom plane, i.e., the tongue and groove engagement arrangement is configured and arranged to constrain movement of the first and second wall portions that are generally sideways when the RPT device 6000 is in a normal, operational orientation. Such constrainment of the walls prevents any wall deflection that can lead to air gaps between the walls and hence acoustic leaks. It also increases the overall stiffness of the enclosure, thus reducing the vibration and the transmitted noise emitted by the enclosure.

Gasket

In the illustrated example, the seal 6300 may be a gasket that is arranged to be in compression between the first intermediate surface 6118 of the first portion 6110 and the second intermediate surface 6128 of the second portion 6120 in use, so as to form a seal between the first portion 6110 and the second portion 6120 along at least a portion of the engagement perimeter or engaged peripheral edge (i.e., along at least a portion of the joint or interface between adjacent first and second wall portions when in the assembled configuration). In the illustrated example, the surfaces 6118, 6128 are flat, and the seal 6300, e.g., gasket, is arranged to form a seal between two flat surfaces 6118, 6128. However, it should be appreciated that the surface 6118 and/or the surface 6128 may not be flat, and at least a portion of the surface 6118 and/or the surface 6128 may include a curvature. As such, the seal 6300, e.g., gasket, may be configured and arranged to form a seal between flat and/or non-flat (e.g., curved) surfaces. In an example, the seal 6300 may be a sealing bead arranged to form a seal between the surfaces 6118, 6128.

In the illustrated example (e.g., see FIGS. 3U to 3W), the seal 6300, e.g., gasket, is provided or otherwise secured to the first intermediate surface 6118 of the first portion 6110 (e.g., the tongue 6210), and the seal 6300, e.g., gasket, is configured and arranged to sealingly engage and form a compression seal with the second intermediate surface 6128 of the second portion 6120 in the assembled configuration (e.g., see FIG. 3N-2). In an alternative example, as shown in FIGS. 3X and 3Y, the seal 6300, e.g., gasket may be provided or otherwise secured to the second intermediate surface 6128 of the second portion 6120, and the seal, e.g., gasket, is configured and arranged to sealingly engage and form a compression seal with the first intermediate surface 6118 of the first portion 6110 in the assembled configuration. FIG. 3Z shows another example of the seal 6300, e.g., gasket, provided to the groove 6220 of the second portion 6120, in which the seal 6300, e.g., gasket, includes an alternative shape, e.g., bead-like gasket or a sealing bead with a semi-circularly shaped cross-section. However, it should be appreciated that the seal 6300, e.g., gasket, may not necessarily be integrally attached to the first or the second portion, but be provided as a separate structure from the first and second portions and arranged between the first intermediate surface and the second intermediate surface in the assembled configuration. In an alternative arrangement, each of the portions may have a seal, e.g., gasket, associated with it.

In the illustrated example, the seal 6300, e.g., gasket, is provided along the entire periphery of the peripheral edge of the first portion 6110, i.e., seal, e.g., gasket, extends continuously along the entire first intermediate surface 6118 of the first portion 6110 (e.g., the tongue 6210). However, it should be appreciated that the seal, e.g., gasket, may be provided to the periphery of the first portion in other suitable manners, e.g., seal provided to one or more selected portions of the first portion 6110 along its periphery.

In the illustrated examples in FIGS. 3N-1 to 3N-3, the seal 6300, e.g., gasket, is of a width (also thickness) that is smaller than the width/thickness of the underlying intermediate surface 6118. Thus, the seal, e.g., gasket, may be of a width/thickness that is smaller than that of at least one of the intermediate surfaces 6118 and 6128. This may be linked to the intended sealing configuration (under pressure) or to the specific manufacturing process employed. The seal 6300, e.g., gasket, comprises a resiliently flexible or deformable material (e.g., viscoelastic material, TPE, TPU, TPV) that is able to, under pressure, deform so as to seal or fill in any air gaps at least between the first and second intermediate surfaces 6118, 6128 (e.g., due to surface imperfections and/or variation in flatness across the surface), thereby preventing conducted noise from escaping the enclosure at the joint or interface between the first portion 6110 and the second portion 6120 when in the assembled configuration. In addition to providing a seal between 6118 and 6128, the seal, e.g., gasket, when compressed, may also bulge laterally (with respect to the direction of applied force) such that it contacts at least one of the groove inner walls 6223, 6225, thereby increasingly seal effectiveness and further reducing the possibility of noise transfer. Increased applied force will lead to increased lateral deformation until both walls 6223, 6225 are contacted, at which point the deformation of the seal ceases as its deformation is bounded on all sides 6118, 6128, 6223, 6225. This may be advantageous in preventing over-stressing of the seal and/or providing the path least navigable by noise.

In an example, the seal 6300, e.g., gasket, may be removably attached or permanently attached (e.g., by way of over-molding or adhesive) to the first intermediate surface 6118 of the first portion 6110 or to the second intermediate surface 6128 of the second portion.

In the illustrated example, the seal 6300, e.g., gasket, comprises a cross-sectional shape that is configured and arranged to enhance sealing under pressure. For example, the seal 6300, e.g., gasket, shown in FIGS. 3V and 3N-3, includes a relatively thick region 6310 that provides a base for attachment to the first portion 6110, and a relatively thin region 6320 that provides a free end or engagement surface for engagement with the second portion 6120 (e.g., the seal, e.g., gasket, is thicker at the base and middle than at the edge). The relatively thin region 6320 at the free end provides a smaller surface area adapted to engage the second intermediate surface 6128 of the second portion 6120, which increases the concentration of force per unit area to enhance sealing when in the assembled configuration.

Exemplary shapes for the seal 6300, e.g., gasket, include: substantially D-shaped, substantially double chamfer, substantially triangular, substantially circular or semi-circular, or substantially D-ring shaped. For example, the free end or engagement surface of the seal 6300, e.g., gasket, may include at least one surface that does not extend parallel to the second intermediate surface 6128 of the second portion 6120, i.e., at least one surface is curved or sloped and may provide a taper towards the free end of the seal, e.g., gasket.

In an example, the seal 6300, e.g., gasket, includes a thickness that is sufficient to limit appreciable sound propagation therethrough, e.g., thickness of the seal is 1-5 mm, e.g., at least 2-3 mm. Moreover, the relatively thick seal, e.g., gasket, when inserted into the tongue and groove engagement arrangement, enhances the torturous path at the interface between the first and second portions 6110, 6120, which diminishes the amount of sound that can pass through, thus creating a more effective acoustic seal.

In an example, the seal 6300, e.g., gasket, includes a length that is sufficient to allow the seal, e.g., gasket, to collapse or compress between the first and second intermediate surfaces 6118, 6128 in the assembled configuration. That is, in the assembled configuration, the tongue 6210 overlaps with the side walls of the groove 6220 in a space between the first and second intermediate surfaces 6118, 6128. The seal 6300, e.g., gasket, includes a length that is sufficiently longer than the length of this space between the first and second intermediate surfaces 6118, 6128 into which is it is located in the assembled configuration so that the seal 6300, e.g., gasket, will deform laterally to form the seal for preventing conducted noise. This is visualised in the hypothetic example shown in FIG. 3N-1, which shows the seal, e.g., gasket, in a hypothetic assembled configuration, in which it is overlapped with the second portion without any compression or deformation. As seen there, the seal, e.g., gasket, is about 1-5 mm longer than the space between the first and second intermediate surfaces to ensure sufficient compression or deformation (e.g., see length L2 in FIG. 3N-1). Thus, the collapsing seal design leverages the principle of conservation of volume and allows the seal, e.g., gasket, to collapse until constrained by the tongue and groove arrangement.

FIG. 3N-2 shows an example of the seal 6300, e.g., gasket, in the assembled configuration when compressed between the first and second intermediate surfaces 6118, 6128. In an example, the seal, e.g., gasket, may compress or collapse so that the deformed seal also engages the outer side wall surface 6225 of the groove 6220 and/or the inner side wall surface 6223 of the groove 6220. This allows the seal, e.g., gasket, to further fill in the space between the first and second portions 6110, 6120 to enhance sealing for reducing noise propagation. In an example, in the assembled configuration, the seal 6300, e.g., gasket, engages at least one of the intermediate surface 6128, outer side wall surface 6225 and/or inner side wall surface 6223 of the groove 6220.

In an example, the seal 6300, e.g., gasket, may comprise a creep-prone material (e.g., TPE, TPU, TPV) that may creep or collapse over time until constrained by the tongue and groove geometry, i.e., seal, e.g., gasket, deforms and fills in or conforms to the open space in the tongue and groove engagement. This may further increase the contact area of the seal, e.g., gasket, with the groove and provide better acoustic isolation. It may also provide a rigid support of the walls of the enclosure, reducing the deformation of the walls and shifting of the walls with respect to each other with time. Also, it may prevent the walls from vibrating independently, the improved vibration dampening further improving the quality and longevity of the seal and the acoustic performance of the resulting structure. Even if it is not creep-prone, the material of the seal, e.g., gasket, is generally non-compressible, but flexible/deformable (e.g., silicone or cross-linked rubbers) and configured to absorb mechanical pressure.

In an example, as shown in FIG. 3P, the seal 6300, e.g., gasket, is configured and arranged to be compressed or squeezed in a direction that is generally perpendicular to the bottom plane BP, i.e., compressed pair of forces U/D applied when the portions 6110 and 6120 are screwed together as part of the assembly process (as viewed in FIG. 3P). That is, force is applied to the top and bottom of the seal, e.g., gasket, (via the first and second intermediate surfaces) to compress the seal, e.g., gasket, and form the seal (e.g., axial or face type seal). More even distribution of the applied compression forces along the engagement edge will lead to more uniform deformation along the length of the seal, e.g., gasket. As the pressure forces in this case is provided by fastening screws, it is recommended that a larger number of more evenly distributed attachment points (the points where the screws are applied) are used. Thus, instead of using 2 or 3 screws to attach the first and the second portion to each other, a larger number (say 4 to 8) screws may be used, preferably evenly spaced along the attachment periphery.

The compression provided by the screws is generally upward/downwards (or vertical) when the RPT device 6000 is in a normal, operational orientation. In an example, the direction of compression may be perpendicular to the direction of lateral constrainment provided by the tongue and groove engagement arrangement. However, it should be appreciated that compression is not limited to only extending in a direction that is generally perpendicular to the bottom plane BP in FIG. 3P, but may be slightly askew or angled relative to the bottom plane.

In an example, the seal 6300, e.g., gasket, is placed under a load, but due to the incompressible nature of the material (e.g., TPE), the seal, e.g., gasket, will deform rather than compress (because the volume of the seal, e.g., gasket, remains substantially constant). The deformation will result in the seal firmly engaging at least one of the surfaces 6128, 6225, 6223 of the groove 6220, and may engage one or both side wall surfaces 6225, 6223 as well (with a commensurate lateral force that is transverse to the direction of the applied load). In an example, i.e., in the case where the seal, e.g., gasket, interacts primarily with the intermediate surface 6128, the force can be concentrated in a smaller area (e.g., thin region 6320 of seal 6300, e.g., gasket, as shown in FIG. 3N-3) so that the sealing force is higher rather than having the load spread out over the entire surface of the groove.

As noted above, interior and/or exterior surfaces of the first portion 6110 and/or the second portion 6120 may include a coating or overmold constructed of a relatively soft material (e.g., TPE or silicone), e.g., to provide damping properties for attenuating wall-radiated noise. In an example, the tongue and/or groove of the first portion 6110 and/or the second portion 6120 may be coated or overmolded (e.g., separately or along with the coating provided to the remainder of the first portion 6110 and/or the second portion 6120) with a relatively soft material (e.g., TPE or silicone), e.g., to enhance sealing, damping and/or retention of the first portion 6110 and the second portion 6120.

In the illustrated example, the tongue and groove engagement arrangement along with the seal 6300, e.g., gasket, provides a system to reduce conducted and radiated noise through the interface between the first portion 6110 and the second portion 6120 of the enclosure 6100 when in the assembled configuration. In this case, a compression seal is formed at least between horizontally (generally parallel to horizontal supporting surface BP in the operational configuration of the device) facing surfaces 6118, 6128 of the first and second portions 6110, 6120 and the seal 6300, e.g., gasket, whilst a containment arrangement is at least partly defined by vertically orientated (inner and outer) surfaces 6114, 6116, 6223, 6225 (transverse to the horizontal supporting surface BP in the operational configuration of the device) of the first and second portions 6110, 6120 (e.g., see FIGS. 3N-1 and 3N-2). In the illustrated example, the seal 6300, e.g., gasket, is structured and arranged to provide at least an acoustic seal, and may also provide a pneumatic seal between the pressurized enclosure and ambient. That is, in an operational configuration of the RPT device, the pressure inside the enclosure adjacent the engagement edge may be elevated compared to ambient (i.e., pressure difference across a wall portion of the enclosure), and the seal 6300, e.g., gasket, along the engagement edge may provide both an acoustic (i.e. noise mitigation) seal and a pneumatic seal between the pressurized enclosure (e.g., one or more pneumatic chambers along the flow path) and ambient. Moreover, the interior of the enclosure may be subject to different pressures, e.g., ambient pressure at the inlet of the enclosure, negative pressure along the interior flow path before the flow reaches the blower, and positive or elevated pressure as the flow is pressurized within and at the outlet side of the blower.

In the above described examples, the seal is effected by the seal 6300, e.g., gasket, being compressed between sealing surfaces of the two engaging portions of the enclosure. In this case, any pressure within the enclosure will actually push the two portions apart and may reduce the quality of the "compression" seal. In an alternative example, usually effected with a flap-like gasket materials of a smaller thickness, the pneumatic pressure within the enclosure may press the gasket surface against a respective sealing surface, thus possibly enhancing the seal between the first and second portions 6110, 6120.

Figure 3R:
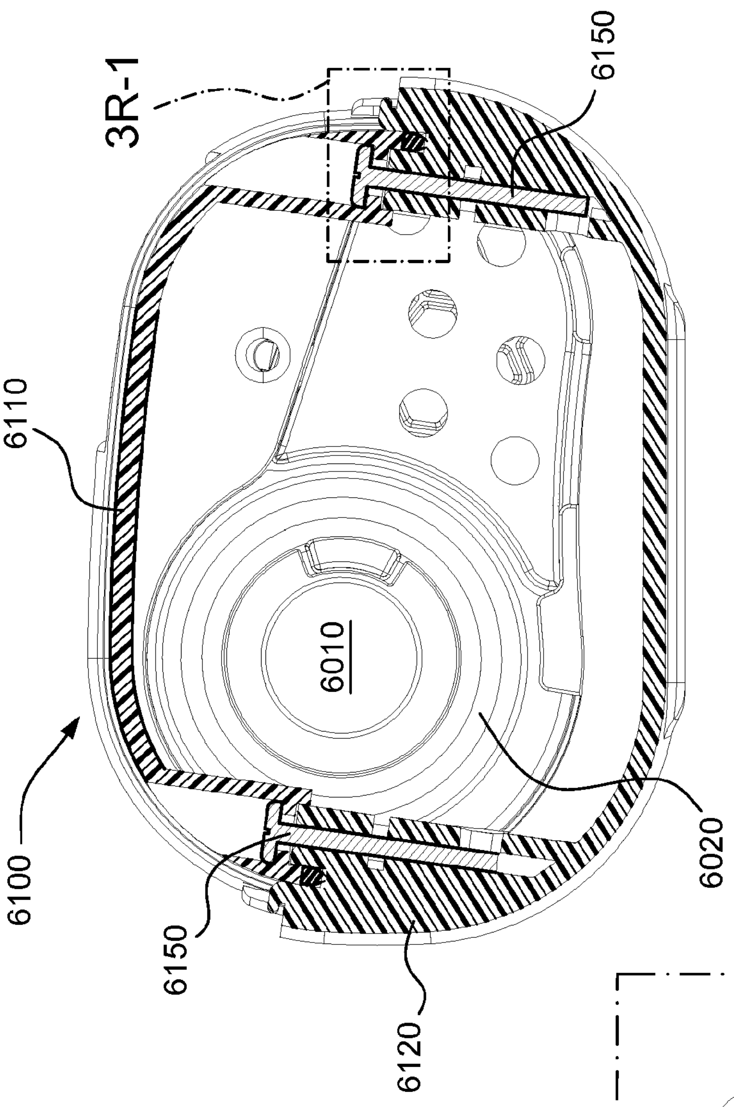
FIG. 3R is a cross-sectional view through line 3R-3R of FIG. 3Q.
Figure 3Q:
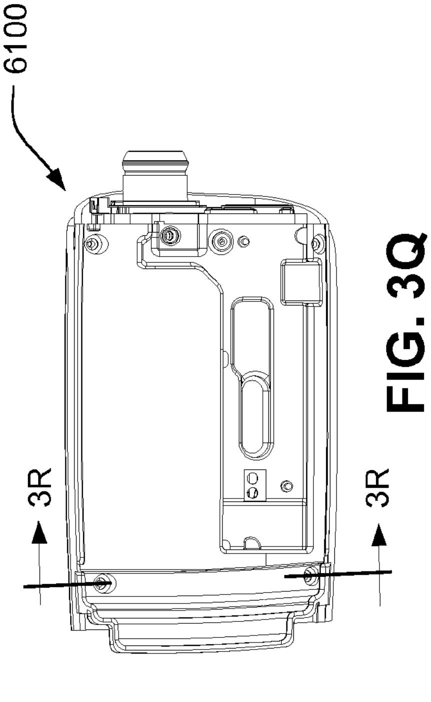
FIG. 3Q is a top view of the enclosure of FIG. 3E.
Figures 1, 3R:
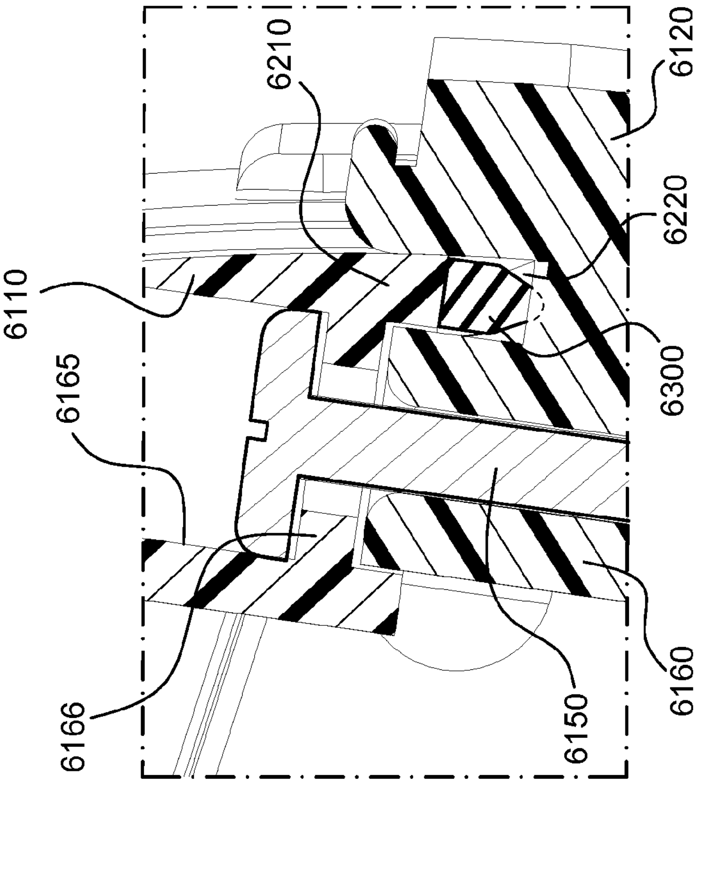
Figure 3S:
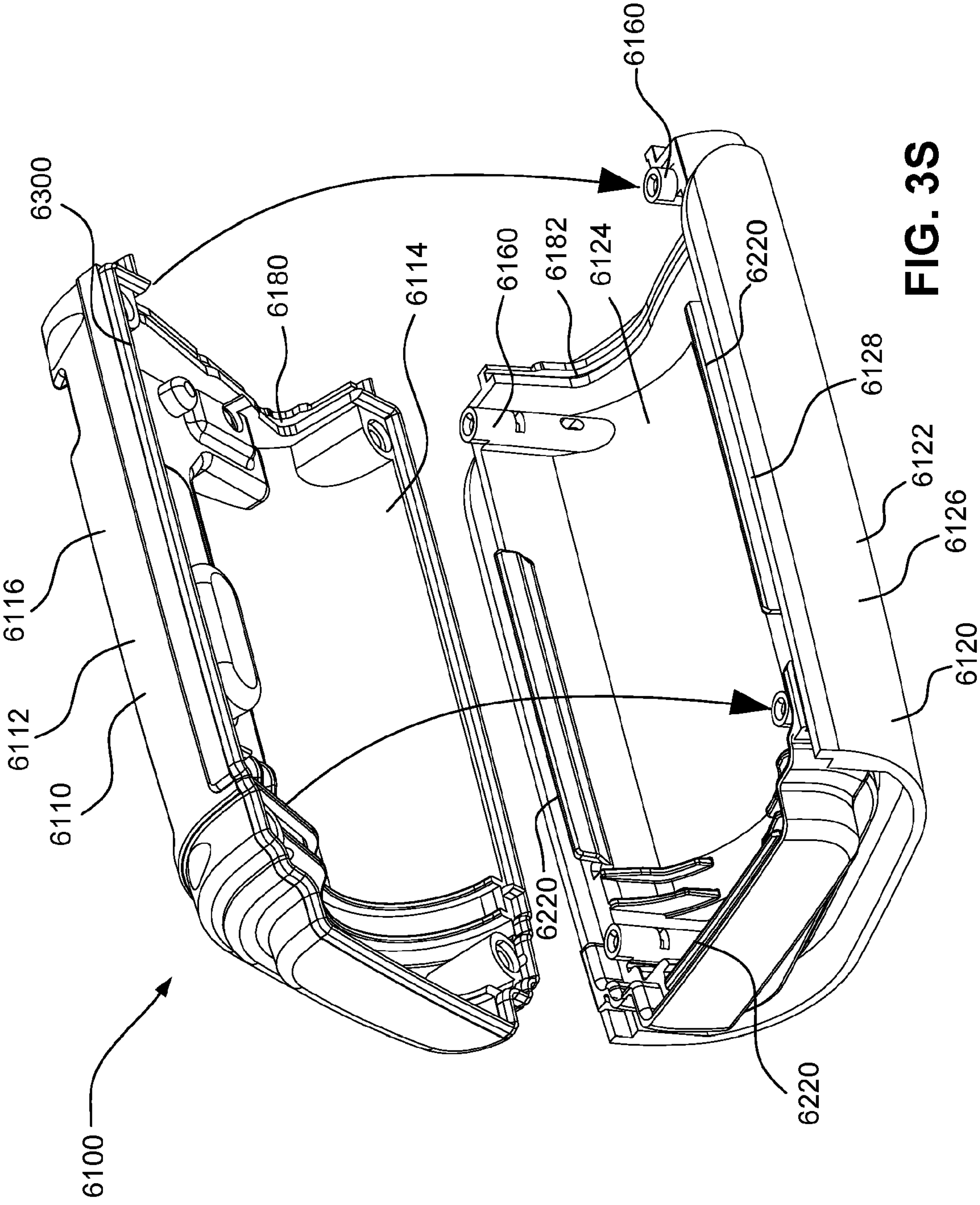
FIG. 3S is a perspective view showing assembly of the upper and lower portions of the enclosure according to an example of the present technology.
Figure 3T:
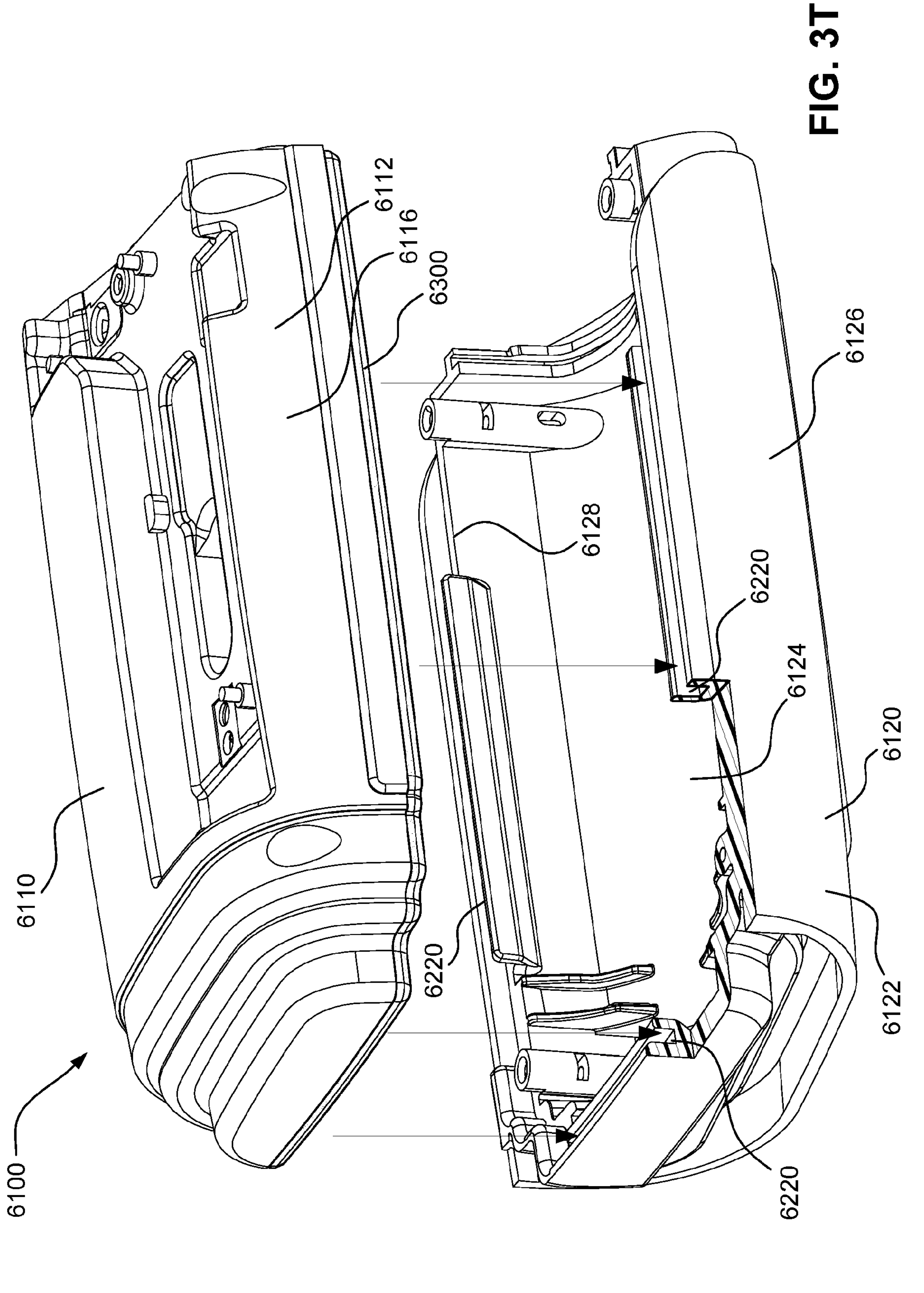
FIG. 3T is a partial cross-sectional view showing assembly of the upper and lower portions of the enclosure according to an example of the present technology.
Figure 3V:
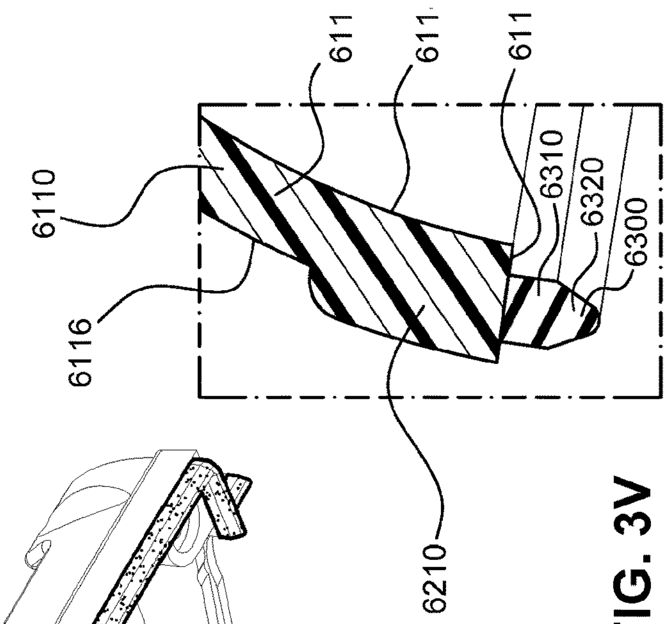
FIG. 3V is a cross-sectional detail view through line 3V-3V of FIG. 3U.
Figure 3U:
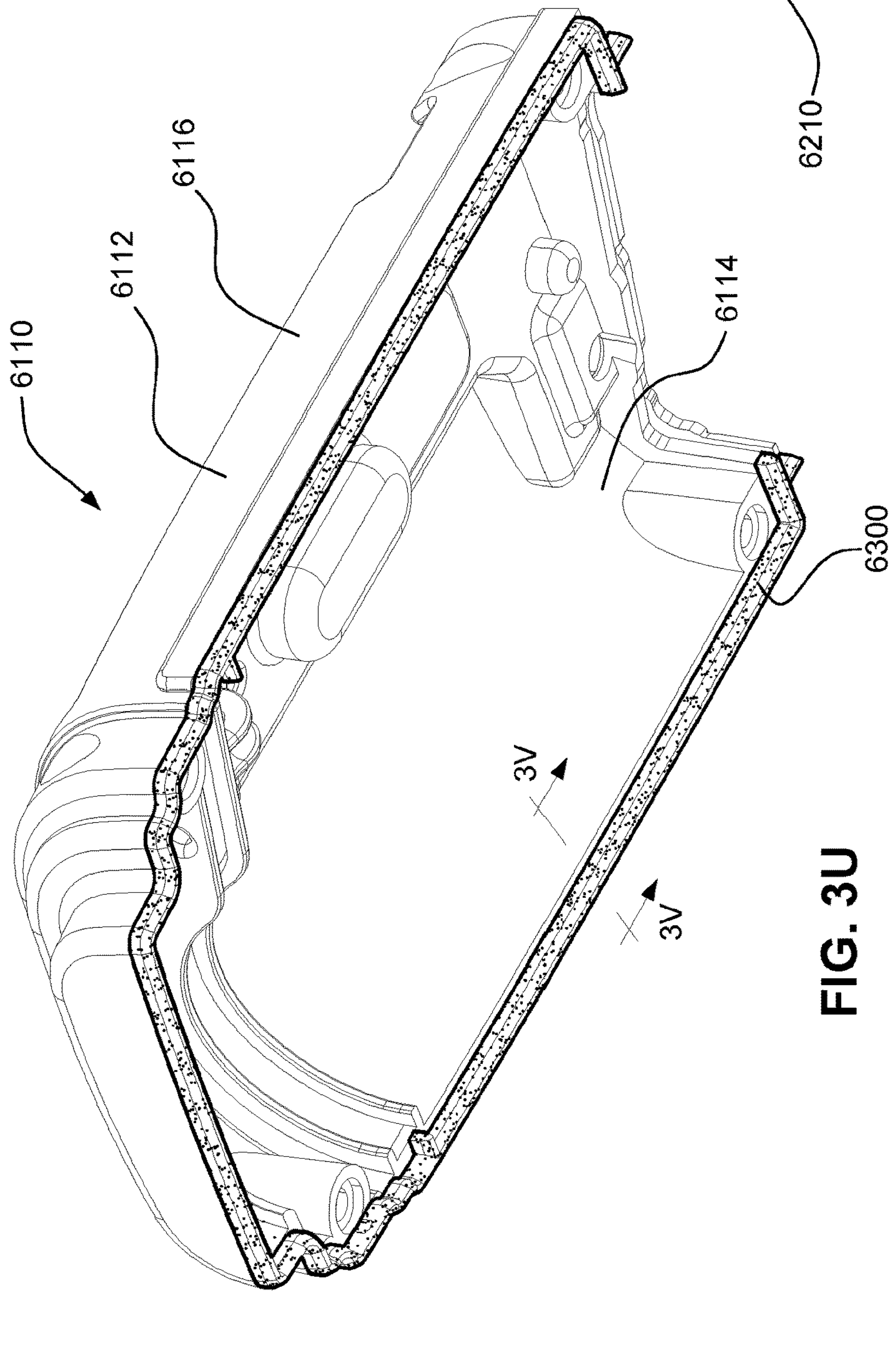
FIG. 3U is a perspective view showing an upper portion of the enclosure according to an example of the present technology.
Figure 3W:
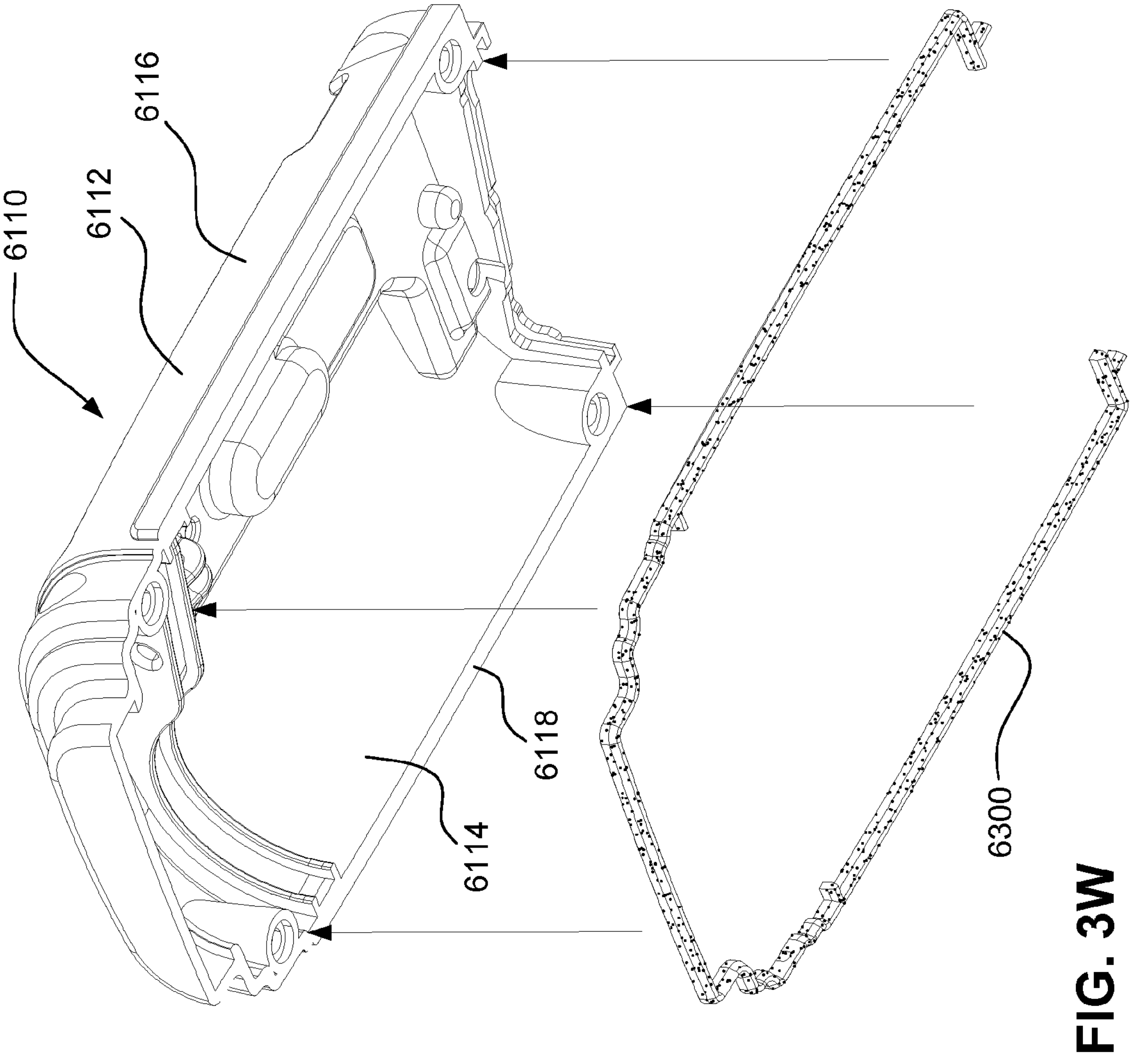
FIG. 3W is an exploded view of the upper portion of the enclosure of FIG. 3U.
Figure 3Y:
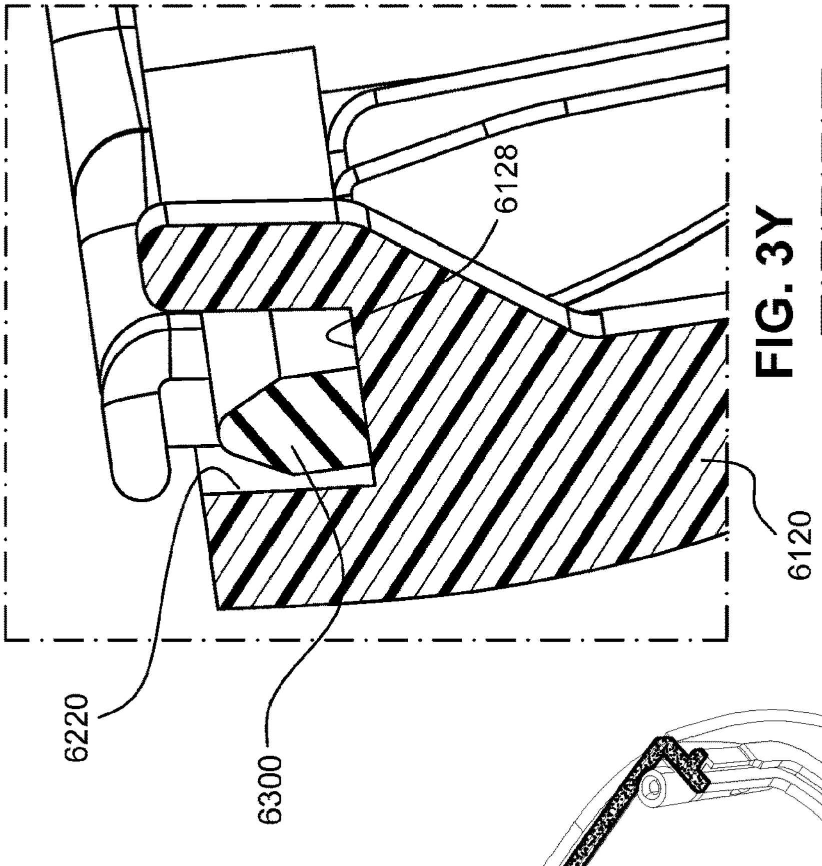
FIG. 3Y is a cross-sectional view through line 3Y-3Y of FIG. 3X.
Figure 3Z:
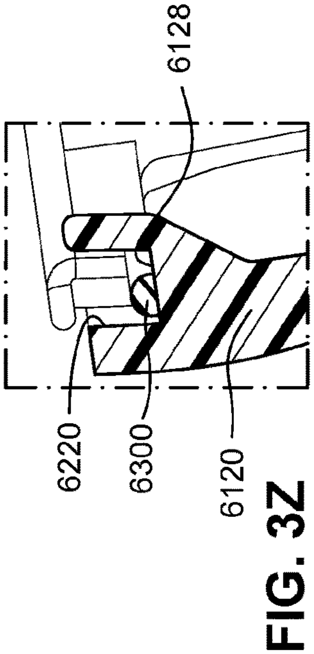
FIG. 3Z is a cross-sectional view similar to FIG. 3Y and showing another possible shape of the seal, e.g., gasket, according to an example of the present technology.
Figure 3X:
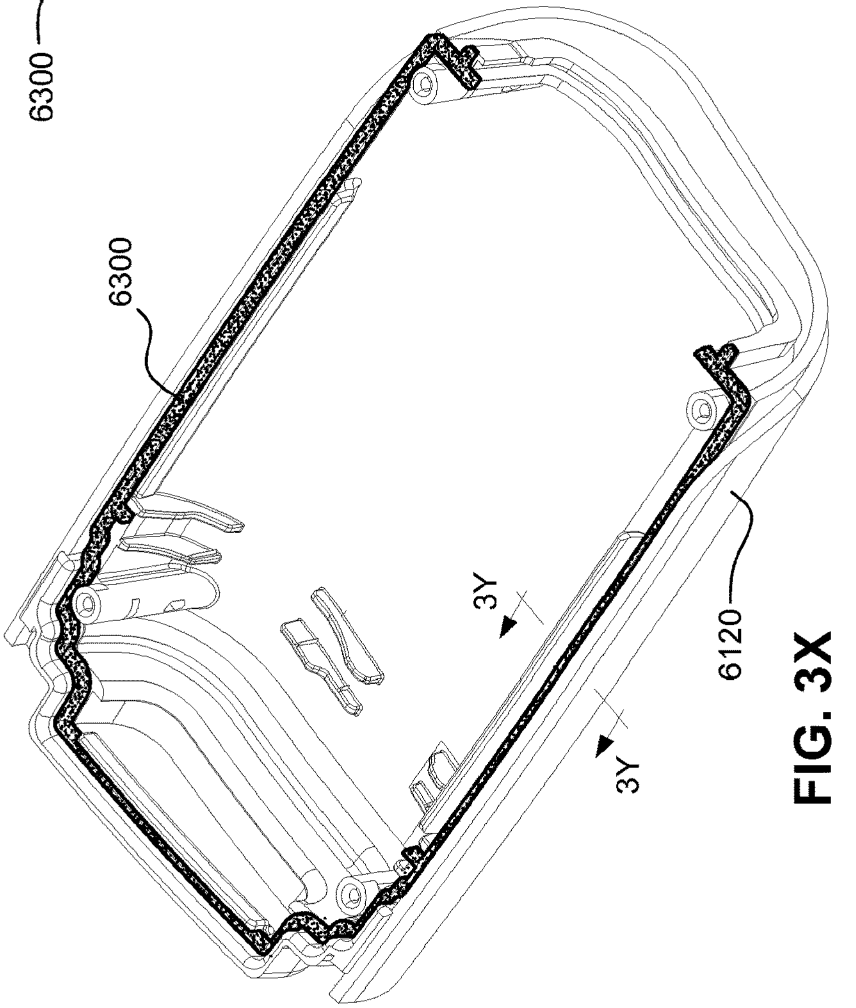
FIG. 3X is a perspective view showing a lower portion of the enclosure according to another example of the present technology.

As already mentioned in the above description, in the illustrated examples, the first portion 6110 may be removable secured to the second portion 6120 in the assembled configuration by one or more fasteners 6150, e.g., one or more threaded screws (see FIG. 3R). Fasteners of different types and dimensions (i.e., length) can be used, providing they effect sufficient load to generate seal, e.g., gasket, compression and seal formation. For example, as shown in FIGS. 3S and 3R-1, the second portion 6120 includes one or more bosses 6160 (e.g., 4 bosses), each of which includes a fastener receiving hole. The first portion 6110 includes a corresponding number of fastener holes 6165 (e.g., 4 holes), each of which includes an interior flange 6166 (see FIG. 3R-1). When the first and second portions 6110, 6120 are assembled to one another (i.e., the tongue is engaged within the groove), each of the flanges 6166 engages or abuts a corresponding one of the bosses 6160 which provides a stop during assembly (see FIG. 3R-1). This stop prevents the tongue 6210 from further insertion into the groove 6220, to indicate that the first and second portions 6110, 6120 have reached a fully assembled configuration. Moreover, this stop may ensure that the tongue 6210 has reached a predetermined level of overlap (e.g., see overlap length L1 in FIG. 3N-1) with the side walls of the groove 6220 for constrainment, and that the seal 6300, e.g., gasket, has reached a predetermined level of compression (e.g., see length L2 in FIG. 3N-1) for acoustic and/or pneumatic sealing. The first and second portions 6110, 6120 are removably secured by the fastener(s) 6150, each of which extends through the aligned fastener holes until the head of the fastener 6150 abuts the flange 6166 (e.g., see FIGS. 3R and 3R-1). It should be appreciated that the stop arrangement may be modified to adjust the predetermined level of overlap/compression, e.g., modify the position of the flange 6166 within the hole, modify the thickness of the flange 6166.

It should be appreciated that one or more aspects of the noise mitigating arrangement described in relation to RPT device 6000 may be incorporated into alternative examples of RPT devices. For example, the RPT device 4000 in FIG. 4A includes a version of the noise mitigating arrangement described herein, e.g., the chassis 4016 that encloses blower 4142 includes a first portion 6110 with a tongue 6210 and a seal 6300, and a second portion 6120 with grooves 6220. In an assembled configuration, the tongue 6210 is received within the grooves 6220 for lateral constrainment of the first and second portions 6110, 6120, and the seal 6300, e.g., gasket, forms a compression seal between the first and second portions 6110, 6120.

5.4.1.2 Air filter(s)

An RPT device 4000, 6000 in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.3 Muffler(s)

An RPT device 4000, 6000 in accordance with one form of the present technology may include a muffler 4120, or a plurality of mufflers 4120, e.g., as schematically shown in FIG. 4B.

Inlet Muffler

In one form of the present technology, an inlet muffler 4122 is located in the pneumatic path upstream of a pressure generator 4140, e.g., as schematically shown in FIG. 4B.

FIGS. 5A to 5K show the RPT device 6000 including a muffling system according to an example of the present technology. The muffling system may comprise one or more inlet mufflers arranged upstream of the blower inlet 6012 of the blower 6010 and/or one or more outlet mufflers arranged downstream of the blower outlet 6014 of the blower 6010. The muffling system is configured and arranged to reduce a noise output of the RPT device 6000 in use.

In the illustrated example, the RPT device 6000 comprises two inlet mufflers (i.e., a device inlet muffler 6350 and a blower inlet muffler 6400) and a blower outlet muffler 6040. The device inlet muffler 6350 and the blower inlet muffler 6400 are arranged along the air flow path upstream of the blower inlet 6012, i.e., between the inlet (e.g., inlet tube array 6052) into the enclosure 6100 and the blower inlet 6012 of the blower 6010. As described below, the blower inlet muffler 6400 may be configured and arranged to reduce a noise output generated by the blower 6010 and/or emanating from the blower inlet 6012 of the blower 6010 in use. The blower inlet muffler 6400 may include one or more components.

In the illustrated example, the blower 6010 includes a single inlet 6012 and a single outlet 6014, which are coaxial. It should be appreciated that the RPT device may include a blower (or blowers) having different configurations, e.g., blower including more than one blower inlets and/or more than one blower outlets, which may be arranged in alternative configurations with respect to one another (e.g., coaxial and/or axially offset from one another, or even angled with respect to one another). Moreover, it should be appreciated that the muffling system according to examples of the present technology may be applicable to RPT devices with alternative blower configurations, e.g., blower inlet muffler arranged upstream of each of the more than one blower inlet of the blower and/or blower outlet muffler arranged downstream of each of the more than one blower outlet of the blower.

In the illustrated example, the enclosure 6100 and internal components of the RPT device 6000 cooperate to form two inlet chambers, i.e., a first chamber 6001 (also referred to as a main chamber or device inlet chamber) and second chamber 6002 (also referred to as a blower inlet chamber) that may be relatively smaller than the first chamber 6001. As illustrated, the blower 6010 is supported in the device inlet chamber 6001, and receives air at the blower inlet 6012 from the blower inlet chamber 6002 (i.e., blower inlet 6012 is located downstream of the chambers 6001, 6002). Various components shown best in FIG. 3F, such as the blower outlet end suspension 6030, the blower outlet muffler 6040, the inlet/outlet assembly 6050, and the blower inlet end suspension 6020 (as described above), can form at least some of the boundaries of the device inlet chamber 6001 (FIG. 5A) and/or the blower inlet chamber 6002 (FIG. 5A). The blower inlet end suspension 6020 and the blower outlet end suspension 6030 support the blower 6010 within the device inlet chamber 6001 and separate and seal air flow through the device inlet chamber 6001 from air flow through an interior of the blower 6010. The inlet tube array 6052 of the inlet/outlet assembly 6050 forms an inlet into the device inlet chamber 6001, and a flow tube array 6025 is arranged to allow air to flow from the device inlet chamber 6001 to the blower inlet chamber 6002.

In the illustrated example, the air flow path of the RPT device 6000 is structured and arranged such that air enters the enclosure 6100 via the inlet tube array 6052, and passes through the inlet tube array 6052 into the device inlet chamber 6001. The device inlet chamber 6001 receives air from the inlet tube array 6052 and delivers the air to the flow tube array 6025 (i.e., the volume forming the device inlet chamber 6001 is at least partially arranged or bounded between the inlet tube array 6052 and the flow tube array 6025). The air passes through the flow tube array 6025 and into the blower inlet chamber 6002. The blower inlet chamber 6002 receives air from the flow tube array 6025 and delivers the air to the blower inlet 6012 (i.e., the volume forming the blower inlet chamber 6002 is at least partially arranged or bounded between the flow tube array 6025 and the blower inlet 6012). The air is pressurized inside the blower 6010 such that a flow of air at positive pressure is provided at the blower outlet 6014 of the blower 6010. This pressurized air is then passed into a blower outlet chamber (a space in which the air moves after leaving the blower outlet, the space forming at least part of the blower outlet muffler 6040) and on to the RPT device outlet (e.g., outlet tube 6054) leading out of the enclosure 6100 (i.e., the volume forming the blower outlet chamber is at least partially arranged or bounded between the blower outlet 6014 and the device outlet (e.g., outlet tube 6054)).

In the illustrated example, the volume of the device inlet chamber 6001 forms at least part of the device inlet muffler 6350, and the volume of the blower inlet chamber 6002 forms at least part of the blower inlet muffler 6400. In an example, noise attenuating material (e.g., one or more portions or pieces of foam or other sound absorptive material) may also be provided to and/or as part of the device inlet chamber 6001 to improve the function or performance of the device inlet muffler 6350, and/or noise attenuating material (e.g., one or more portions or pieces of foam or other sound absorptive material) may be provided to the blower inlet chamber 6002 to improve the function or performance of the blower inlet muffler 6400. For example, the noise attenuating material (e.g., foam) provides an absorptive-type muffler (resonance peak damping) and the volume of each of the chambers 6001, 6002 provides an expansion-type muffler (muffles via expansion of volume) along the air flow path. These two methods of attenuating noise work together to reduce acoustic output and minimise the effect of acoustic resonances. In addition, one or more walls of the enclosure 6100 may be strengthened/stiffened and may include the noise mitigating arrangement described above, e.g., tongue 6210 and groove 6220, which reduces radiated noise and further enhances the function of the device inlet muffler 6350 and/or the blower inlet muffler 6400. Accordingly, each of the device inlet muffler 6350 and the blower inlet muffler 6400 comprises spatial geometry (i.e., space), structure (i.e., rigidizing one) and/or materials configured and arranged to reduce a noise output of the RPT device 6000 in use.

In the illustrated example, the blower inlet muffler 6400 is arranged between the flow tube array 6025 and the blower inlet 6012 of the blower 6010. As described below, the blower inlet muffler 6400 comprises spatial geometry, structure and/or materials arranged upstream of the blower inlet 6012 of the blower 6010 to attenuate noise generated by the created airflow, and by the blower 6010 itself, in use, e.g., blower inlet muffler 6400 comprises space/volume, a rigidizing step-wise wall structure, as well as a noise attenuating material that absorbs energy of the sound waves exiting the blower inlet 6012 of the blower 6010 in use to reduce noise.

In the illustrated example, the absorptive component of the blower inlet muffler 6400 comprises one or more portions or pieces of foam. A further component of the blower inlet muffler 6400 is associated with rigidizing at least a portion of one or more walls of the blower inlet chamber 6002, particularly the portion in front of the blower inlet 6012. For that purpose, an end of the enclosure 6100 comprises a rigidized wall portion 6130 (i.e., a rigid body portion of the enclosure). In the illustrated example, the rigidized wall portion 6130 is configured to accommodate or house the one or more pieces of foam along a periphery of the blower inlet chamber 6002. That is, rather than simply providing a flat end wall or squared off end of the enclosure (to form a side wall of the blower inlet chamber 6002), e.g., as schematically indicated by dashed line FL (FIG. 5E), the enclosure 6100 includes a rigidized wall portion 6130 that projects or extends outwardly from FL to form a space or pocket in the end of the enclosure 6100 to support and retain foam adjacent the blower inlet chamber 6002. In the illustrated example, as described below, the rigidized wall portion 6130 includes a non-planar wall structure or profile (e.g., step-wise wall profile or structure) which forms the space for foam but also adds rigidity to the enclosure to resist deformation, particularly the portion in front of the blower inlet 6012. This provides a further component of the blower inlet muffler 6400 (e.g., rigidizing one or more walls of the blower inlet chamber 6002 to reduce vibrations and hence noise). Instead of a step-wise configuration, one may use other non-planar wall profiles, where the non-planar (i.e., curved, zig-zag, wave-like or the like) nature of the profile still enhances its rigidity to resist deformation. Alternative rigidizing means (e.g., rigidizing ribs or other structures formed in, or attached to, the wall) can also be used.

Using a structure that is aimed to enhance the rigidity of the wall, to also create a space and/or to secure a piece of foam (or other similar sound absorptive component), can combine two or even three, generally independent, muffling components and create a synergetic effect. The effect can be further enhanced by the addition of the expansion-based sound dampening effect of the blower inlet chamber 6002, which is separate from and in addition to, any volume added by the chamber created by the rigidizing step-wise structure. Thus, the overall sound muffling effect of blower inlet muffler 6400 is created by the combination of its three sound dampening components (the volumes of chamber 6002 and the rigidized wall portion, the foam component and the rigid walls of the rigidized wall portion). However, in the particular case best illustrated in FIG. 5A, these three components interact structurally with each other. In the specific example, the foam component defines one of the wall surfaces 6410 and is part of the volume of the chamber 6002, while at the same time, a part of the rigidization structure of the wall of the chamber is also arranged to secure the foam component. This synergetic interaction between the components is especially beneficial in the case of a very compact device, such as the one that is the subject of this description.

In the illustrated example, the rigidized wall portion 6130 is formed by at least one of an end wall portion of the first portion 6110 (e.g., the top) of the enclosure 6100 and an end wall portion of the second portion 6120 (e.g., the bottom) of the enclosure 6100. When the rigidized wall portion is partially formed by both end wall portions, the end wall portion of the first portion 6110 (e.g., the top) forms a first interior slot 6141 (a top slot) where foam can be received (or slotted), and the end wall portion of the second portion 6120 (e.g., the bottom) forms a second interior slot 6142 (a bottom slot). The expressions "top" and "bottom" in this case are used with reference to the standard operational configuration of the device. When the first and second portions 6110, 6120 are in an assembled configuration, the first and second interior slots 6141, 6142 cooperate to form the space or pocket that supports and retains the one or more pieces of foam within the enclosure 6100. That is, in this case, each of the first portion 6110 and the second portion 6120 of the enclosure 6100 supports and retains at least one or more portions or pieces of foam of the blower inlet muffler 6400. In another example, the rigidized wall portion can be formed of only the first portion or only the second portion, or both.

In the illustrated example, e.g., for ease of assembly, the foam of the blower inlet muffler 6400 is also split into two portions or pieces, e.g., a first foam portion or piece F1 and a second foam portion or piece F2. For example, the first foam piece F1 (a top half of the foam of the blower inlet muffler 6400) is pre-assembled or inserted into the first interior slot 6141 of the first portion 6110, and the second foam piece F2 (a bottom half of the foam of the blower inlet muffler 6400) is pre-assembled or inserted into the second interior slot 6142 of the second portion 6120 (e.g., see FIG. 5A). When the first and second portions 6110, 6120 of the enclosure 6100 are in an assembled configuration, the first and second foam pieces F1, F2 may abut one another (and may at least partially compress via a butt joint (flat ends of the foam pieces F1, F1 simply butted against one another (FIG. 5G) and/or may overlap (lap joint in which ends of the foam pieces F1, F2 at least partially overlap one another)) to fill the space formed by the first and second interior slots 6141, 6142 (e.g., see FIGS. 5E and 5G). That is, the first and second foam pieces F1, F2 cooperate to form the whole foam of the blower inlet muffler 6400, i.e., the first and second foam pieces F1, F2 cooperate to form a larger foam pad or block.

In an alternative arrangement, slots 6141 and 6142 may be part of a single body portion and/or the foam of the blower inlet muffler 6400 may comprise a single one-piece foam pad or block that is supported and retained within the space formed by the first and second interior slots 6141, 6242 of the enclosure 6100. However, it should be appreciated that the foam of the blower inlet muffler 6400 may comprise any number of foam pieces along a periphery of the blower inlet chamber 6002. In the example, the use of the first and second foam pieces F1, F2 may facilitate assembly, e.g., as the first and second foam pieces F1, F2 may be simply inserted into respective first and second portions 6110, 6120 before the first and second portions 6110, 6120 are assembled to one another (e.g., see FIG. 5A) which does not require any additional alignment when the first and second portions 6110, 6120 are assembled.

When the one or more foam pieces of the blower inlet muffler 6400 are in an assembled configuration within the enclosure 6100, the one or more foam pieces are arranged to avoid obstruction of air flow along the air flow path and provide sound absorption. The arrangement is such that, even if some peripheral part of the flow encounters the foam on its path, the main flow path is unobstructed.

As illustrated, the end wall portion of each of the first and second portions 6110, 6120 forms a rear, sides, and a bottom of the respective slot 6141, 6142, which support a rear, sides, and a bottom of the respective foam piece F1, F2 received therein. Moreover, the end wall portion of each of the first and second portions 6110, 6120 includes a respective lip 6141L, 6142L projecting away from the sides and/or bottom of the respective slot 6141, 6142, which supports a front perimeter edge of the respective foam piece F1, F2 received therein. As such, a front face or surface 6410 of each foam piece F1, F2 is exposed to the blower inlet chamber 6002 to form a wall or surface along the boundary of the blower inlet chamber 6002, and therefore the front face 6410 is exposed and forms a boundary of the air flow path that extends to the blower inlet 6012 of the blower 6010. In the illustrated example, the foam pieces F1, F2 are arranged along the air flow path such that the air flow does not pass through the thickness of the foam pieces F1, F2. Rather, the foam pieces F1, F2 are arranged at the boundary of the air flow path to avoid increasing flow impedance.

Moreover, at least a portion of the front face or surface 6410 of the foam pieces F1, F2 is arranged directly opposite and faces the blower inlet 6012 of the blower 6010, thereby arranging the foam pieces F1, F2 at a location that is directly impacted by the sound generated in the blower 6010.

In the illustrated example, the foam pieces F1, F2 of the blower inlet muffler 6400 are arranged such that the axis 6012*ax* (see FIG. 5C) of the blower inlet 6012 passes through a volume of the blower inlet chamber 6002 and a thickness of at least one of the foam pieces F1, F2 (e.g., see FIGS. 5C and 5E). Also, in the illustrated example, the blower inlet 6012 comprises an opening 6012*op* (i.e., a sound broadcasting opening) forming an area, and the foam pieces F1, F2 are arranged such that the area of the blower inlet opening 6012*op* projects at least partly onto at least one of the foam pieces F1, F2. That is, the area of the blower inlet opening 6012*op* has an outer extent that projects at least partly onto at least one of the foam pieces F1, F2 of the blower inlet muffler 6400. In an example, the foam pieces F1, F2 are arranged such that the area of the blower inlet opening 6012*op* projects in its entirety onto at least one of the foam pieces F1, F2, e.g., the front face or surface 6410 provided by the foam pieces F1, F2 provides an area that is greater than the projected area provided by the blower inlet opening 6012*op*. In an alternative example, the foam pieces F1, F2 may be arranged such one or more portions of the foam pieces F1, F1 are at least partially offset from the blower inlet opening 6012*op* and/or blocked (e.g., by one or more walls) so that the blower inlet opening 6012*op* may only project partly onto the foam pieces F1 and/or F2, or not at all. In an example, the foam pieces F1, F2 are arranged to cover end wall portions of the enclosure 6100 (i.e., a direct impact zone of sound from the blower inlet 6012) to muffle or dampen sound emanating from the blower inlet 6012 towards end wall portions of the enclosure 6100. The remaining side walls of the blower inlet chamber 6002 may also be lined up with foam material to assist with the absorption of any scattered and/or reflected sound. Thus, the portion of the blower inlet chamber 6002 that surrounds the blower inlet opening 6012*op* may include (a) space, (b) rigidized wall, and (c) be partially or completely lined up with sound absorption material.

Also, in the illustrated example, at least a portion of the front face or surface 6410 of the foam pieces F1, F2 may be arranged opposite and face the flow tube array 6025. For example, the flow tube array 6025 includes a plurality of flow tubes 6026 (arranged in parallel) supported by a base plate 6027, and the foam pieces F1, F2 are arranged such that the axis 6026*ax* of one or more of the flow tubes 6026 passes through a volume of the blower inlet chamber 6002 and a thickness of at least one of the foam pieces F1, F2 (e.g., see FIG. 5C). Also, in the illustrated example, each flow tube 6026 comprises an opening 6026*op* forming an area, and the foam pieces F1, F2 are arranged such that the area of one or more of the flow tube openings 6026*op* projects at least partly (e.g., in its entirety) onto the foam pieces F1 and/or F2 (i.e., the foam pieces F1 and/or F2 at least partly face at least one of the openings of the flow tubes). As such, the foam pieces F1, F2 are arranged along the periphery of the air flow path extending from the flow tube array 6025 to the blower inlet 6012 to also provide relatively efficient sound absorption for sound originating from the flow tubes. In an alternative example, the foam pieces F1, F2 may be arranged such one or more portions of the foam pieces F1, F1 are at least partially offset from flow tube array 6025 and/or blocked (e.g., by one or more walls) so that the flow tube openings 6026*op* do not project onto the foam pieces F1 and/or F2.

In the illustrated example, the blower 6010 includes an axis (coaxial with blower inlet axis 6012*ax*) that is substantially parallel to the axis 6026*ax* of each of the flow tubes 6026, however the axis (i.e., axis 6012*ax*) of the blower 6010 is not coaxial with the axis 6026*ax* of each of the flow tubes 6026. That is, in the illustrated example, the axis of the blower (i.e., axis 6012*ax*) is offset or spaced apart from the axis 6026*ax* of each of the flow tubes 6026). As such, in the illustrated example, one or more foam pieces of the blower inlet muffler 6400 includes a length L (e.g., see FIG. 5C) sufficient to allow the axis (i.e., axis 6012*ax*) of the blower 6010 and/or the axis 6026*ax* at least one (e.g., all) of the flow tubes 6026 of the flow tube array 6025 to pass therethrough. However, it should be appreciated that the blower and/or flow tubes 6026 may include other suitable arrangements, e.g., axis of the blower 6010 not being parallel to the flow tubes 6026 or axis of the blower 6010 being coaxial to the flow tubes 6026. Also, it should be appreciated that the one or more foam pieces of the blower inlet muffler 6400 may not span the full distance between the blower and 6010 the flow tubes 6026, e.g., the one or more foam pieces may only span across the projection of the blower 6010.

In an example, the foam pieces F1, F2 of the blower inlet muffler 6400 may be axially displaced or spaced from the blower inlet 6012 of the blower 6010 (and from the flow tubes 6026 of the flow tube array 6025) by about 5-40 mm (e.g., about 10-30 mm, about 15-25 mm, 19-21 mm), however other suitable distances are possible (e.g., depending on the desired size of the flow width provided by blower inlet chamber 6002). For example, a minimum spacing or flow width may be determined in view of impedance to air flow in the blower inlet chamber 6002. If the spacing is too small, the impedance may be unacceptable for desired performance. If the spacing is too large, the overall size of the device may be undesirably large. That is, the practical limitations of impedance at least partly determine the spacing between the foam pieces F1, F2 and the blower inlet 6012 used in the device. However, it should be appreciated that, in some examples, high impedance (and hence smaller flow area) may be tolerable, e.g., for a device where power consumption is less of a constraint.

In the illustrated example, the interface (as schematically indicated by line IF in FIG. 5G) between the first and second portions 6110, 6120 of the enclosure 6100 may extend in a plane that is not necessarily horizontal with respect to a bottom plane BP defined relative to the operational orientation of the device, e.g., interface line IF extends at an angle with respect to bottom plane BP. As such, each piece of foam F1, F2 may be pre-formed or cut so that the interfacing or abutting surfaces of the foam pieces F1, F2 meet and extend along a plane that is generally parallel to the plane of the interface line IF (e.g., see FIG. 5G). In alternative examples, the interface IF and/or the interface between foam pieces F1, F2 may be horizontal (i.e., parallel to the bottom plane BP).

In the illustrated example, one or more additional pieces of foam may be provided within the device inlet chamber 6001 and/or the blower chamber 6002, e.g., for sound absorption.

For example, foam F3 may be provided to the first portion 6110 (e.g., the top) of the enclosure 6100 so that foam is arranged along the top and/or the sides of the blower inlet chamber 6002, and/or foam F4 may be provided to the second portion 6120 (e.g., the bottom) of the enclosure 6100 so that foam is arranged along the bottom (i.e., the floor) and/or the sides of the blower inlet chamber 6002. One or more bulk pieces of foam located at least partially in the flow path may be used. However, because of the impedance imparted to the air flow, it may be preferable to use this additional foam in the form of wall lining so that one or more walls of the first portion 6110 and/or the second portion 6120 forming the blower inlet chamber 6002 are covered with foam which provides damping properties to attenuate radiated noise, while having minimal impedance effect on the airflow. In an alternative example, one or more pieces of foam may be arranged in the flow path, but the one or more pieces of foam includes one or more holes or passageways therethrough to allow unimpeded air flow to the blower inlet, i.e., one or more tunnels or cored-out pipes through the one or more pieces of foam.

Similarly, foam F5 may be provided to the second portion 6120 (e.g., the bottom) of the enclosure 6100 so that foam is arranged along the bottom (i.e., the floor) and/or the sides of the device inlet chamber 6001. In an example, the foam F5 may at least partially surround and/or support the blower 6010 within the device inlet chamber 6001 and provide sound absorption and suspension (e.g., see FIG. 5I). While not illustrated, in an alternative example, foam may be provided to the first portion 6110 (e.g., the top) of the enclosure 6100 so that foam is arranged along the top and/or the sides of the device inlet chamber 6001. As such, one or more walls of the first portion 6110 and/or the second portion 6120 forming the device inlet chamber 6001 are covered with foam which provides damping properties to attenuate radiated noise.

Accordingly, in the illustrated example, at least a portion of the air flow path (e.g., under negative pressure) that extends from the RPT device inlet (e.g., inlet tube array 6052) into the enclosure 6100 and to the blower inlet 6012 of the blower 6010 is at least partially enclosed by foam F1, F2, F3, F4, F5 to reduce noise. As noted above, the foam provides an absorptive-type muffler that works together with an expansion-type muffler provided by the volumes of the chambers 6001, 6002 to reduce acoustic output and minimise the effect of acoustic resonances.

In an example, each piece of foam F1, F2, F3, F4, F5 comprises a noise absorptive-type foam. An exemplary material for the foam is an open cell foam, e.g., acoustic grade polyurethane open cell foam (e.g., density of about 32 $kg/m^3$), silicone open cell foam (e.g., density of about 100 $kg/m^3$).

In an example, each piece of foam includes a thickness of about 4-10 mm (e.g., 6-10 mm), however other suitable thicknesses are possible, e.g., 4 mm or more. In an example, the foam pieces F1, F2 may include a thickness of about 4-10 mm (e.g., 4-6 mm), the foam pieces F3, F4 may include a thickness of about 4-10 mm (e.g., 4-6 mm), and the foam piece F5 may include a thickness of about 4-10 mm (e.g., 5-9 mm). In an example, the foam pieces may include similar or different thicknesses compared to one another, e.g., foam piece F2 may be thinner than foam piece F1 in order to accommodate the structure of the groove 6220 that protrudes into the slot 6142 (e.g., see FIG. 5E). In an example, each of the foam pieces includes a thickness to at least fully fill its respective slot. In an example, the thickness and/or volume of each of the foam pieces F1, F2, F3, F4, F5 may be limited so as to not unduly increase impedance along the air flow path and to maintain compactness of the overall device while reducing noise output.

In an example, the foam piece F5 may comprise a solid foam block (rather than a constant thickness sheet) structured and arranged to fill the device inlet chamber 6001, the solid foam block comprising cored-out "pipes" (e.g., holes or passageways) through its thickness to allow for airflow (between the inlet tube array 6052 and the flow tube array 6025) and to allow for mounting of the blower 6010 (e.g., blower 6010 supported or surrounded by the foam block). In such example, an ancillary benefit would arise with the foam acting as impact protection for the blower 6010, e.g., in the event the device is dropped.

In the illustrated example, each of the foam pieces F1, F2, F3, F4, F5 is pre-formed or cut into its desired shape before insertion into its respective portion of the enclosure 6100. In an alternative example, the foam may be an injected-type foam configured to be injected into respective portions of the enclosure 6100, e.g., before or after assembly of the enclosure 6100 and internal components. Alternatively, one or more of the pieces of foam may be thermoformed and/or glued to the respective portion of the enclosure 6100.

In the illustrated example, the rigidized wall portion 6130 (i.e., a rigid body portion of the enclosure 6100) was introduced to make space for the foam pieces F1, F2 of the blower inlet muffler 6400. However, at the same time, the rigidized wall portion 6130 represents a structure that increases the stiffness of the enclosure 6100 to resist deformation in response to an applied load (e.g., pressure fluctuations causes by noise from the blower), thus reducing vibration and hence noise in use.

As illustrated, the walls of the first portion 6110 (e.g., the top) and the second portion 6120 (e.g., the bottom) of the enclosure 6100 that form the rigidized wall portion 6130, instead of comprising a simple curved-plane profile, may also follow a more complex profile. For example, as shown, they can cooperate to form a step-wise configuration, i.e., a stepped end wall portion including at least one step and possibly multiple extension steps. In the illustrated example, the rigidized wall portion 6130 includes a first step 6131 that protrudes in and the out from FL, and a second step 6133 that protrudes in and out from the first step 6131 to form a step-wise extension from FL of the enclosure (e.g., see FIG. 5E), leading to a dome-shaped end wall or cap 6135. Each face or wall 6132 (e.g., see FIGS. 5C, 5E, and 5G) of the steps 6131, 6133 may have a curvature (e.g., exterior surface of the steps may comprise cylindrical, dome and/or saddle regions) to increase stiffness. For example, FIG. 3E shows an exemplary region of step 6133 in which the exterior surface comprises a cylindrical region. Also, each of the corners of the stepped end wall may include a curvature. For example, FIG. 3E shows an exemplary peripheral transition region or edge 6139 between the steps 6131, 6133 in which the exterior surface comprises a saddle region. The number of steps, the width of each step, the thickness of the walls and/or the curvature of walls/corners may be modified to impact the stiffness (e.g., walls may include flat and/or non-flat (e.g., angled and/or curved) geometries with curvature in one or more directions). The step-wise extension leads to the dome-shaped end wall or cap 6135 (e.g., exterior surface of the end wall 6135 comprises a dome region as shown in FIG. 3E) of the rigidized wall portion 6130. Also, it should be appreciated that the rigidized wall portion may include other suitable non-flat and/or flat geometry to form the foam space while strengthening/rigidizing the end of the enclosure. That is, the transition from the end of the enclosure to the rigidized wall portion could take on many forms, e.g., the illustrated step-wise extension and dome-shaped end wall, but may also comprise an angled portion, or just have a continuous curved (i.e. dome-shaped) from the end of the enclosure. In an example, one or more portions of the rigidized wall portion may comprise a separate structure from the enclosure, e.g., step-wise extension formed as part of the enclosure with the dome-shaped end wall attached to the step-wise extension. It should be appreciated that rigidity may be provided by the geometry of the rigidized wall portion (e.g., step-wise extension and dome-shaped end wall), but also the thickness and/or materials, as well as the structure of the walls (i.e., rigidizing ribs).

Further, in the illustrated example, the end wall or cap 6135 of the rigidized wall portion 6130 includes the further noise mitigating arrangement described above, e.g., tongue 6210 and groove 6220, which further enhances stiffness and hence reduces radiated noise.

In the illustrated example, the end of the enclosure 6100 adjacent the blower inlet 6012 of the blower 6010 includes several aspects to reduce noise, e.g., (1) stiffened (also referred to as rigidized) end walls (step-wise configuration of the rigidized wall portion 6130) to reduce vibration caused by noise, (2) tongue and groove engagement arrangement to assist with case stiffness to reduce radiated noise, (3) damping (e.g., foam F1, F2, F3, F4) to absorb noise and reduce sound reflection, and (3) expansion of flow area provided by blower inlet chambers 6002. For example, the broadcasting inlet opening 6012 of the blower 6010 faces enclosure 6100, at least a portion of the walls of which is strengthened/stiffened (with two-dimensional curvature (e.g., dome region), multiple extension steps and/or tongue and groove), and any wall of the enclosure 6100 facing the broadcasting inlet opening 6012 of the blower 6012 is covered in foam F1, F2 in order to reduce the ability of the wall to reflect sound (i.e., reduction in sound energy that can be broadcast).

While it is recommended to cover the entire face of the enclosure 6100 facing the blower inlet 6012 with one or more foam pieces, even a partial coverage (say at least one of the areas directly opposite the blower inlet 6012 and the flow tube array 6025) will also have an appreciable muffling impact on the generated sound. Furthermore, while the sound absorbing element is continuously referred to as foam, other sound absorbing materials (rubber, porous materials (i.e., textile), etc. can also be used.

Outlet Muffler

In one form of the present technology, an outlet muffler 4124 is located in the pneumatic path between the pressure generator 4140 and a patient interface 3000, e.g., as schematically shown in FIG. 4B.

As described above, the muffling system of the RPT device 6000 may comprise one or more outlet mufflers arranged downstream of the blower outlet 6014 of the blower 6010. In the illustrated example (e.g., as shown in FIGS. 3F to 3N and 5A to 5E), the RPT device 6000 comprises a single blower outlet muffler 6040 that is arranged along the air flow path downstream of the blower outlet 6014, i.e., between the blower outlet 6014 of the blower 6010 and the outlet (e.g., outlet tube 6054) out of the enclosure 6100. As described below, the blower outlet muffler 6040 may be configured and arranged to reduce a noise output generated by the blower 6010 and/or emanating from the blower outlet 6014 of the blower 6010 in use. The blower outlet muffler 6040 may include one or more components, or be formed by other components of the RPT device 6000, or portions of such components.

In the illustrated example, air is pressurized inside the blower 6010 such that a flow of air at positive pressure is provided at the blower outlet 6014 of the blower 6010. This pressurized air is then passed into a blower outlet chamber 6003 (forming at least part of the blower outlet muffler 6040) and on to the RPT device outlet (e.g., outlet tube 6054) leading out of the enclosure 6100. That is, the volume forming the blower outlet chamber 6003 is at least partially arranged or bounded between the blower outlet 6014 and the device outlet (e.g., outlet tube 6054).

Discrete-Type Blower Outlet Muffler

In the example shown in FIGS. 3F to 3N and 5A to 5E and 6A to 6P, the blower outlet muffler 6040 comprises a main body 6042 that forms the blower outlet chamber 6003. As illustrated, the main body 6042 includes one or more walls or wall portions, e.g., a central wall portion 6043 and opposing end wall portions 6045, 6047 as shown in FIGS. 6C and 6D. In an example, the main body 6042 may comprise a relatively rigid, plastic material (e.g., polypropylene, polyethylene, or other suitable polymers). In an example, the main body 6042 may be molded in one piece, or may be molded of two or more pieces that are later assembled to one another.

In the illustrated example, the main body 6042 forming the blower outlet chamber 6003 comprises a separate and distinct structure from the enclosure 6100. The main body 6042 comprises a separate and discrete enclosure inside the enclosure 6100, such that the walls of the enclosure 6100 do not form any boundaries or portions of the main body 6042 and the blower outlet chamber 6003 thereof. That is, the main body 6042 does not share walls with the enclosure 6100 to form the blower outlet chamber 6003, i.e., the main body 6042 forms a discrete blower outlet chamber 6003 that is isolated from the enclosure 6100. However, in an alternative example (e.g., see FIGS. 7A to 7L described below), the enclosure 6100 may be structured and arranged to form one or more boundaries or portions of the blower outlet chamber 6003, i.e., the blower outlet chamber 6003 may be at least partially integrated with the enclosure 6100.

In the illustrated example, the volume of the blower outlet chamber 6003 forms only a part of the blower outlet muffler 6040. As well seen in FIGS. 6A-6C, the main body 6042 of the blower outlet muffler 6040 further includes space which is more closely associated with the inlet path IP of the RPT device, along which inlet air enters the enclosure (outlet path OP also shown in FIGS. 6A-6C along which pressurized air exits the enclosure). In particular, the space in question is the part of the main body 6042 of the blower outlet muffler 6040, which encloses at least a portion of the length of the inlet tubes 6053 (in a different embodiment, the entire lengths of the inlet tubes may be enclosed). Space around inlet tubes 6053 forms also part of the main body 6042 of the blower outlet muffler 6040. Thus, the blower outlet chamber 6003 surrounds the inlet tubes 6053 and, in doing so, extends beyond the location of the inlet path IP (in the form of the inlet tubes 6053). This affords the use of space around the inlet tubes 6053 otherwise unavailable as muffler volume, thereby increasing the available muffling volume and improving the efficiency of the blower outlet muffler 6040. In another example, the blower outlet muffler and the inlet tubes may be arranged such that the inlet tubes do not pass through the body of the outlet muffler. Passing inlet tubes through the outlet muffler is advantageous for reducing device size and flow impedance, however routing the inlet tubes such that they do not consume muffler volume would be advantageous in maximising muffler volume (related to its effectiveness).

In an example, noise attenuating material (e.g., one or more portions or pieces of foam or other sound absorptive material) may also be provided to and/or as part of the blower outlet chamber 6003 to improve the function or performance of the blower outlet muffler 6040. For example, the noise attenuating material (e.g., foam) provides an absorptive-type muffling (resonance peak damping) and the volume of the chamber 6003 provides an expansion-type muffling (muffles via expansion of volume) along the air flow path. These two methods of attenuating noise work together to reduce acoustic output and minimise the effect of acoustic resonances. In addition, one or more walls of the main body 6042 may be strengthened/stiffened, which can reduce radiated noise and further enhance the function of the blower outlet muffler 6040. Accordingly, the blower outlet muffler 6040 may comprise spatial geometry (i.e., space), structure (i.e., rigidized walls) and/or materials (i.e., foam) combined and arranged to reduce a noise output of the RPT device 6000 in use.

In an example, noise attenuating material (e.g., foam) may be provided to the main body 6042 so that foam is arranged along the top, bottom and/or sides of the blower outlet chamber 6003. Because of the impedance imparted to the air flow, it may be preferable to use foam in the form of a wall lining so that one or more walls of the main body 6042 forming the blower outlet chamber 6003 are covered with foam. However, no foam is positioned in the air path so that foam does not obstruct flow, ensuring minimal impedance effect on the airflow. The wall lining may be in the form a relatively thin (several millimetres) foam layer attached to one or more inner walls. Alternatively, a bulk piece of foam may be included in the space, which fills in essentially the entire volume, apart from a region left clear of foam allowing unimpeded air flow. In one such example, as shown in FIG. 6P, foam F6 may substantially fill the blower outlet chamber 6003, but include a hole or passageway h1 (cored-out pipe) therethrough to allow unimpeded air flow from the blower outlet 6014 to the outlet tube 6054. Also, as illustrated, the foam F6 may include a hole or passageway h2 therethrough to accommodate the inlet tube array 6052. A combination may also be used, where one or more portions of the muffler are wall-lined, whilst one or more other portions include a bulk piece of foam, as described above.

In the illustrated example, the discrete main body 6042 of the blower outlet muffler 6040 is suspended within the enclosure 6100 by the inlet/outlet assembly 6050 in a manner that may further improve the function or performance of the blower outlet muffler 6040.

As shown in FIGS. 6C, 6D, 6F and 6G, the inlet/outlet assembly 6050 includes a base plate 6051 that supports the inlet tube array 6052 (including a plurality of inlet tubes 6053 arranged in parallel) and the outlet tube 6054. The inlet end of the outlet tube 6054 may comprise a pressure port 6055. An outlet seal 6060 may be provided to the outlet end of the outlet tube 6054. In addition, a sealing assembly 6070 is provided to the base plate 6051, the inlet tube array 6052, and the outlet tube 6054. Specially, the sealing assembly 6070 includes a sealing lip or sealing flange 6072 along the edge or perimeter of the base plate 6051, an inlet end seal 6074 along the inlet end of the outlet tube 6054, a port seal 6075 extending from the pressure port 6055, and seal portions 6076, 6077 along the base plate 6051 surrounding the outlet end of the outlet tube 6054 and the inlet end of the inlet tube array 6052. In an alternative example, the function of the inlet end seal 6074 may be achieved by gluing, overmoulding or otherwise permanently attaching the base plate 6051 to the main body 6042, e.g., to simplify assembly.

In an example, the base plate 6051, the inlet tube array 6052, and the outlet tube 6054 may comprise a first part or base mold constructed of a relatively rigid material (e.g., polypropylene or polyethylene), and the outlet seal 6060 and sealing assembly 6070 may comprise a second part or overmold constructed of a relatively soft material (e.g., TPE or silicone) that is provided (e.g., by overmolding) to the first part.

In an example, the inlet/outlet assembly 6050 may be provided to the main body 6042 to form a sub-assembly (e.g., see FIGS. 6A, 6B, 6E, 6F) before insertion into the enclosure 6100.

In the illustrated example, as best shown in FIGS. 6C and 6D, the end wall portion 6045 of the main body 6042 includes a first opening 6045*o*1 configured to receive the blower outlet end suspension 6030 (e.g., suspension 6030 overmolded to the main body 6042, e.g., to simplify assembly and reduce part count) and a second opening 6045*o*2 configured to receive the inlet tube array 6052, and the other end wall portion 6047 of the main body 6042 includes a tube portion 6047*t* configured to receive the outlet tube 6054 and an opening 6047*o* configured to receive the inlet tube array 6052. As illustrated, the opening 6045*o*1 and the tube portion 6047*t* are axially aligned with one another, and the openings 6045*o*2, 6047*o* are axially aligned with one another.

As best shown in FIGS. 6A, 6B, and 6L, the inlet/outlet assembly 6050 is engaged with the main body 6042 such that the inlet tube array 6052 protrudes to, or through, the opening 6047*o* of the end wall portion 6047, through the volume or chamber 6003 of the main body 6042, and through the opening 6045*o*2 of the end wall portion 6045. As shown in FIGS. 6A and 6B, when assembled, the base plate 6051 abuts the end wall portion 6047 and the outlet end of the inlet tube array 6052 is arranged outside the main body 6042 (so as to extend into the device inlet chamber 6001 when the inlet/outlet assembly 6050 is provided to the enclosure 6100). As illustrated, each of the openings 6045*o*2, 6047*o* includes a shape that corresponds to a shape of the inlet tube array 6052 along its outer perimeter, which axially retains the inlet tube array 6052 in position. In an example, when the inlet/outlet assembly 6050 is assembled to the main body 6042, the base plate 6051 may form one or more wall portions of the chamber 6003 (e.g., the base plate 6051 may cover one or more openings in the end wall portion 6047 of the main body 6042).

As best shown in FIGS. 6A, 6B, 6E, 6F, J, and 6M, when the inlet/outlet assembly 6050 is assembled to the main body 6042, the outlet tube 6054 (and inlet end seal 6074 thereof) engages within the tube portion 6047*t* of the end wall portion 6047. The inlet end seal 6074 is arranged between the tube portion 6047*t* and the inlet end of the outlet tube 6054 to form a seal along the air flow path. In the illustrated example, the outlet tube 6054 (and inlet end seal 6074 thereof) and the tube portion 6047*t* include a step-like configuration, e.g., to enhance sealing (tortuous interface). That is, as best shown in FIGS. 6F and 6M, the inlet end of the outlet tube 6054 (and inlet end seal 6074 thereof) includes a step-like configuration and the tube portion 6047*t* include a step-like configuration, and such step-like configurations are arranged to abut against one another, thus ensuring frictional sealing (side to side) as well as face-to face sealing (pressure assisted seal). However, it should be appreciated that the outlet tube 6054 and the tube portion 6047*t* of the main body 6042 may be configured and engaged with another in other suitable manners to provide a pneumatic and acoustic seal allowing both the delivery of therapy air and containment of sound energy, e.g., outlet tube 6054 bonded to tube portion 6047*t* by an adhesive, outlet tube 6054 molded in one piece with tube portion 6047*t*, outlet tube 6054 overmolded to tube portion 6047*t*.

Also, the main body 6042 includes a cut-out 6049 to accommodate the port seal 6075 extending from the pressure port 6055 (see FIGS. 6A to 6D), which allows the port seal 6075 to interface or otherwise connect to a pressure sensor (e.g., provided to the PCB) for measuring outlet pressure in the blower outlet chamber 6003. In an example, noise attenuating material (e.g., foam) within the blower outlet chamber 6003 may be used as a filter for the pressure port 6055.

In an example, the pressure port 6055 may be arranged along a top wall of the main body 6042 to more directly communicate with the interior of the blower outlet chamber 6003, which may provide a more precise measurement of the chamber pressure. Such a measurement may be more precise because of reduced turbulence, e.g., the measurement is outside of the flow stream (outside the outlet air path extending from the blower outlet 6014 to the outlet tube 6054) and the noise attenuating material (e.g., foam) within the blower outlet chamber 6003 may shield the opening of the pressure port 6055 from any turbulence. Locating the cut-out 6049 at the top of the body 6042 allows the port seal 6075 to interface with a pressure sensor provided to a PCB located superior to the main body, when in operational configuration.

As discussed previously in the text in relation to the muffling efficiency of the outlet muffler, in the illustrated example, its main body 6042 is extended to surround or wrap around at least a portion of the outlet tube 6054 as well as the inlet tube array 6052 (rather than trimming the main body 6042 to end at an outer perimeter of the inlet tube array 6052). Such arrangement maintains a compact form while increasing the chamber volume of the main body 6042, e.g., by about 30% compared to a main body trimmed to the outer perimeter of the inlet tube array 6052. That is, the main body 6042 extends substantially the entire width of the enclosure 6100 to maximize the volume of the blower outlet chamber 6003.

FIGS. 6A, 6B, 6E, and 6F show the sub-assembly of the inlet/outlet assembly 6050 and the main body 6042 before engagement with the blower 6010 and insertion into the enclosure 6100. In an example, one or more portions of the inlet/outlet assembly 6050 may be adhered to the main body 6042 to more securely retain the inlet/outlet assembly 6050 to the main body 6042. However, the inlet/outlet assembly 6050 and the main body 6042 may include alternative retaining arrangements (e.g., press or snap fit assembly).

As shown in FIGS. 3S, 6G, and 6J, the end of first portion 6110 of the enclosure 6100 includes a groove 6180, and the end of second portion 6120 of the enclosure 6100 includes a groove 6182. When the first and second portions 6110, 6120 are in an assembled configuration, the base plate 6051 is engaged (by way of the sealing lip 6072 along its perimeter) within the grooves 6180, 6182 so that the base plate 6051 is supported and constrained between the first and second portions 6110, 6120 of the enclosure 6100. As such, the first and second portions 6110, 6120 support the inlet/outlet assembly 6050 at one end of the enclosure 6100. The supported inlet/outlet assembly 6050 in turn supports the main body 6042 within the interior of the enclosure 6100.

As illustrated, the main body 6042 is suspended from the inlet/outlet assembly 6050 in a cantilever manner such that the walls of the main body 6042 are arranged in spaced relation from the walls of the enclosure 6100 (i.e., dual wall arrangement). Even a small spacing (e.g., from about 0.5 mm to about several millimetres) or air gap between the main body 6042 and the enclosure 6100 provides acoustic insulation. That is, the discrete main body 6042 (which is an independent component including walls that are separate and distinct from walls of the enclosure 6100) is supported in spaced relation from the enclosure 6100 so that the air gap along an exterior area of the main body 6042 isolates radiated noise from the main body 6042. Thus, the vibration of the walls of the main body 6042 (due to sound emanating from the blower outlet 6014 (e.g., from spinning impellers, flow noise, bearings)) is decoupled or isolated from the walls of the enclosure 6100. Moreover, the sealing lip 6072 along the perimeter of the base plate 6051 resiliently supports the base plate 6051 between the first and second portions 6110, 6120, which provides resilient suspension of the main body 6042 to further reduce vibrations or radiated noise.

In addition, the blower outlet end suspension 6030 provided to the main body 6042 is configured to resiliently support the blower 6010 adjacent the blower outlet 6014 of the blower 6010. As shown in FIG. 6F, the blower outlet end suspension 6030 (e.g., constructed of an elastomeric material such as TPE or silicone) includes an outer portion 6031 provided (e.g., overmolded) to the first opening 6045*o*1 of the main body 6042, an inner portion 6032 engaged or otherwise secured to the blower outlet 6014 of the blower 6010, and a gusset portion 6033 between the outer and inner portions 6031, 6032.

The inner portion 6032 of the blower outlet end suspension 6030 may be secured to the blower 6010 in any suitable manner, e.g., wrap around an outlet flange provided to blower outlet 6014 as shown in FIGS. 6J and 6L. The blower outlet end suspension 6030 seals the blower outlet 6014 to the main body 6042, thereby sealing the air path and mitigating any leaks for pressurized air exiting the blower outlet 6014 and entering into the blower outlet chamber 6003 from the device inlet chamber 6001. Also, the gusset portion 6033 of the blower outlet end suspension 6030 allows flexibility and relative movement to isolate vibrations of the blower 6010 and provide shock resistance, e.g., the blower outlet suspension 6030 is arranged to resiliently support the blower to at least limit propagation of blower vibration to the main body 6042.

The inclusion of a discrete main body 6042 forming the blower outlet chamber 6003 provides a less direct path of vibration and noise being conducted to the enclosure 6100 and exiting the device, e.g., any vibration from the blower 6010 must pass along the blower outlet end suspension 6030, along the main body 6042, along the base plate 6051, to the sealing lip 6072. That is, the discrete main body 6042 provides another form of decoupling vibration/noise originating from the blower 6010.

The outlet seal 6060 (shown in FIG. 6F) provided to the outlet end of the outlet tube 6054 is structured and configured to form a seal with an end of the air circuit 4170, e.g., cuff of an air delivery tube. The outlet seal 6060 (e.g., constructed of an elastomeric material such as TPE or silicone) includes an end portion 6061 provided (e.g., overmolded) to the tube portion 8053 and a flexible lip 6062 that curves radially inwardly from the end portion 6061. The flexible lip 6062 is resiliently flexible to allow the end of the air circuit to engage and form a seal with the flexible lip 6062, thereby sealing the air path for pressurized air exiting the outlet tube 6054 into the air circuit.

In the illustrated example, as shown in FIGS. 3L, 6J, 6L, and 6M, the blower 6010 includes an axis 6010*ax* (coaxial with at least one or both of the axis of the blower inlet 6012 and the axis of the blower outlet 6014 (i.e., when both axes are coaxial air enters and exits the blower along a common axis)) that is also coaxial with an axis 6054*ax* of the outlet tube 6054. That is, the blower outlet end suspension 6030 provided to the main body 6042 and the blower inlet end suspension 6020 provided to the base plate 6027 can be configured and arranged to resiliently support the blower 6010 such that the blower axis 6010*ax* is arranged to be substantially coaxial with the outlet tube axis 6054*ax*. Such arrangement forms a direct outlet air path for pressurized air exiting the blower outlet 6014 to the outlet tube 6054, i.e., line of sight for the outlet air path to reduce outlet impedance. In another example, the outlet tube 6054 may be enlarged to a diameter greater than that of the blower outlet 6014 (greater internal diameter). This arrangement is advantageous as it allows flexibility in the precise position of the blower 6010 within the enclosure 6100. As long as the projection of the blower outlet 6014 falls within the aperture of the outlet tube 6054, the position of the blower 6010 may be adjusted without inducing significant additional flow noise, thus maintaining an efficient outlet muffler.

As shown in FIG. 6L, the inlet tube array 6052 (including the plurality of inlet tubes 6053 arranged in parallel) is structured and arranged to extend from the base plate 6051 and through the chamber 6003 of the main body 6042, such that the outlet end of the inlet tube array 6052 is arranged outside the main body 6042 and extends into the device inlet chamber 6001 of the enclosure 6100. The inlet end of the inlet tube array 6052 is arranged along an outer side of the base plate 6051 (side facing away from the main body 6042) and forms an inlet into the enclosure 6100. In an example, the RPT device 6000 may include a top case or fascia 6090 that forms an external casing of the device, and the top case 6090 may include inlet openings 6091 (see FIGS. 3A-1 and 3C) to allow air to pass through the top case 6090 and into the inlet tube array 6052. In the illustrated example, each of the inlet tubes 6053 includes an axis that is offset and substantially parallel to the axis 6010*ax* of the blower 6010.

In an example, as shown in FIG. 3J, the sub-assembly of the inlet/outlet assembly 6050 and the main body 6042 (and blower outlet end suspension 6030 thereof) may be engaged with the outlet end of the blower 6010, and the base plate 6027 (and blower inlet end suspension 6020 thereof) may be engaged with the inlet end of the blower 6010, so as to form a blower sub-assembly which is then assembled to the enclosure 6100, i.e., blower sub-assembly inserted into the second portion 6120 before attachment of the first portion 6110.

FIGS. 6Q and 6R are schematic diagrams of the dynamic support of the blower 6010 within the enclosure 6100 and differing degrees of freedom. As illustrated, the blower inlet end suspension 6020 provides spring-like resilient support of the blower 6010 to the base plate 6027, and the blower outlet end suspension 6030 provides spring-like resilient support of the blower 6010 to the main body 6042 of the blower outlet muffler 6040. In addition, the base plate 6027 includes a sealing lip 6028 along its perimeter which provides spring-like resilient support of the base plate 6027 to the enclosure 6100, and the main body 6042 is cantilevered off the base plate 6051 which includes sealing lip 6072 along its perimeter providing spring-like resilient support of the main body 6042 (and hence the blower 6010) to the enclosure 6100. Thus, the suspensions 6020, 6030 and the sealing lips 6072 and 6028 cooperate to provide an enhanced (to some extent—dual) suspension that resiliently suspends the blower 6010 within the enclosure 6100 to isolate vibrations or radiated noise. Also, the use of the lip seals 6028, 6072 (that readily bend or deflect in contrast to thicker beads used for compression-type seal) around the base plates 6027, 6051 minimizes the likelihood of such seals interfering with the assembly of the RPT device by preventing the proper and complete closure of the first and second portions 6110, 6120 of the enclosure 6100, i.e., compression seal only used between the first and second portions 6110, 6120 of the enclosure 6100.

Integrated-Type Blower Outlet Muffler

FIGS. 7A to 7L show an alternative example in which the enclosure 6100 is structured and arranged to form one or more boundaries or portions of the blower outlet chamber 6003, i.e., the blower outlet chamber 6003 is at least partially integrated with the enclosure 6100.

In this example, the volume forming the blower outlet chamber 6003 is arranged or bounded by a blower outlet end suspension assembly 6080 (e.g., a first plate assembly), an inlet/outlet assembly 6050 (e.g., a second plate assembly), and walls of the enclosure 6100. That is, in contrast to the example of FIGS. 6A to 6R, the walls of the enclosure 6100 cooperate with the inlet/outlet assembly 6050 and the blower outlet end suspension assembly 6080 to form the blower outlet chamber 6003. In this example, the removal of a separate enclosure for the blower outlet chamber 6003 (i.e., main body 6042) may add extra volume to the blower outlet chamber 6003, which extra volume may enhance noise reduction. Also, the removal of the separate enclosure (i.e., main body 6042) may improve manufacturability and ease of assembly, and may reduce cost. While the vibration isolation path is simplified by removing the cantilever support arrangement represented in FIGS. 6Q and 6R, the combination of increased muffler chamber volume and tuning of the dynamic behaviour of the suspension 6030 allow for equivalent overall system performance.

In the illustrated example, the volume of the blower outlet chamber 6003 again forms at least part of the blower outlet muffler 6040. In an example, noise attenuating material (e.g., one or more portions or pieces of foam or other sound absorptive material) may also be provided to and/or as part of at least a portion of the blower outlet chamber 6003, to improve the function or performance of the blower outlet muffler 6040.

Thus, the structure of the muffler chamber and its muffling operation is similar to that of the above described discrete-type blower outlet muffler 6040. Similar to the above example, the inlet/outlet assembly 6050 includes a base plate 6051 that supports the inlet tube array 6052 (including a plurality of inlet tubes 6053 arranged in parallel) and the outlet tube 6054. The inlet end of the outlet tube 6054 may comprise port seal 6075 extending from a pressure port. An outlet seal 6060 may be provided to the outlet end of the outlet tube 6054. In addition, a sealing lip or sealing flange 6072 is provided along the edge or perimeter of the base plate 6051 and seal portions 6076, 6077 along the base plate 6051 surrounding the outlet end of the outlet tube 6054 and the inlet end of the inlet tube array 6052.

The blower outlet end suspension assembly 6080 includes a base plate 6081 and a sealing lip or sealing flange 6082 along the edge or perimeter of the base plate 6081. The base plate 6081 includes a first opening 6084*o*1 configured to receive the blower outlet end suspension 6030 and a second opening 6084*o*2 configured to receive the inlet tube array 6052.

As shown in FIGS. 7B, 7C and 7G, the first portion 6110 of the enclosure 6100 includes a first groove 6180 and a second groove 6181 spaced apart from the first groove 6180, and the second portion 6120 of the enclosure 6100 includes a first groove 6182 and a second groove 6183 spaced apart from the first groove 6182. When the first and second portions 6110, 6120 are in an assembled configuration, the base plate 6051 (and the sealing lip 6072 along its perimeter) is engaged within the first grooves 6180, 6182 so that the base plate 6051 is supported and constrained between the first and second portions 6110, 6120 of the enclosure 6100. Likewise, when the first and second portions 6110, 6120 are in an assembled configuration, the base plate 6081 (and the sealing lip 6082 along its perimeter) is engaged within the second grooves 6181, 6183 so that the base plate 6081 is supported and constrained between the first and second portions 6110, 6120 of the enclosure 6100. As such, the first and second portions 6110, 6120 support the inlet/outlet assembly 6050 and the blower outlet end suspension assembly 6080 in spaced-apart relation within the interior of the enclosure 6100, with the base plate 6051, the base plate 6081, and adjacent walls of the enclosure 6100 cooperating to form the blower outlet chamber 6003.

As best shown in FIGS. 7F and 7H, the inlet/outlet assembly 6050 is arranged with respect to the blower outlet end suspension assembly 6080 such that the inlet tube array 6052 protrudes through the second opening 6084*o*2 of the base plate 6081, which arranges the outlet end of the inlet tube array 6052 to be outside the blower outlet chamber 6003 (so as to extend into the device inlet chamber 6001 when assembled to the enclosure 6100). In the illustrated example, the blower outlet chamber 6003 surrounds the inlet tube array 6052 (i.e., the blower outlet chamber 6003 extends again substantially the entire width of the enclosure 6100), which maximize the volume of the blower outlet chamber 6003.

The blower outlet end suspension 6030 provided to the blower outlet end suspension assembly 6080 is configured to support the blower 6010 adjacent the blower outlet 6014 of the blower 6010. As best shown in FIG. 7C, the blower outlet end suspension 6030 (e.g., constructed of an elastomeric material such as TPE or silicone) includes an outer portion 6031 provided (e.g., overmolded) to the first opening 6084*o*1 of the base plate 6081, an inner portion 6032 engaged or otherwise secured to the blower outlet 6014 of the blower 6010 (e.g., wrap around an outlet flange provided to blower outlet 6014), and a gusset portion 6033 between the outer and inner portions 6031, 6032 that allows flexibility and relative movement to isolate vibrations of the blower 6010 and provide shock resistance.

FIG. 7H shows an exemplary sub-assembly of the inlet/outlet assembly 6050 and the blower outlet end suspension assembly 6080 before engagement with the blower 6010 and insertion into the enclosure 6100. In an example, the inlet tube array 6052 of the inlet/outlet assembly 6050 may be adhered to the blower outlet end suspension assembly 6080 to more securely retain the inlet/outlet assembly 6050 to the blower outlet end suspension assembly 6080. However, the inlet/outlet assembly 6050 and the blower outlet end suspension assembly 6080 may include alternative retaining arrangements (e.g., press or snap fit assembly). Also, in an example, the inlet tube array 6052 of the inlet/outlet assembly 6050 may be molded to the base plate 6081 of the blower outlet end suspension assembly 6080, and be arranged to snap lock to the inlet/outlet assembly 6050. In an alternative example, the base plate 6081 of the blower outlet end suspension assembly 6080 and the base plate 6051, the inlet tube array 6052, and the outlet tube 6054 of the inlet/outlet assembly 6050 may be molded in one piece.

In an example, the sub-assembly of the inlet/outlet assembly 6050 and the blower outlet end suspension assembly 6080 (and blower outlet end suspension 6030 thereof) may be engaged with the outlet end of the blower 6010, and the base plate 6027 (and blower inlet end suspension 6020 thereof) may be engaged with the inlet end of the blower 6010, so as to form a blower sub-assembly which is then assembled to the enclosure 6100, i.e., blower sub-assembly inserted into the second portion 6120 before attachment of the first portion 6110. As shown in FIGS. 7B and 7G for example, the first and second portions 6110, 6120 of the enclosure include corresponding grooves 6185 configured and arranged to support and constrain the base plate 6027 (and the sealing lip 6028 along its perimeter) when the first and second portions 6110, 6120 are in an assembled configuration.

Similar to the above example, as shown in FIGS. 7B and 7C, the blower 6010 includes an axis 6010*ax* (coaxial with the axis of the blower inlet 6012 and the axis of the blower outlet 6014) that is coaxial with an axis 6054*ax* of the outlet tube 6054. That is, the blower outlet end suspension 6030 provided to the base plate 6081 and the blower inlet end suspension 6020 provided to the base plate 6027 are configured and arranged to resiliently support the blower 6010 such that the blower axis 6010*ax* is arranged to be substantially coaxial with the outlet tube axis 6054*ax*. Such arrangement forms a direct outlet air path for pressurized air exiting the blower outlet 6014 to the outlet tube 6054 to reduce outlet impedance.

As illustrated, the blower suspensions 6020, 6030 and the sealing lips 6028, 6082 cooperate to provide spring-like resilient support of the blower 6010 within the enclosure 6100 to isolate vibrations or radiated noise.

In an example, because the base plate 6081 (sealing lip 6082 thereof) and the base plate 6051 (and sealing lip 6072 thereof) form at least a portion of the blower outlet chamber 6003 which is exposed to high air pressure, more robust seals than lip seals 6082, 6072 (that readily bend or deflect) may be used to minimize leaks. For example, thicker beads providing a compression-type seal (e.g., like the compression type seal 6300 described above) may be provided around the base plates 6081, 6051 (rather than lip seals 6082, 6072) to provide improved high pressure seal between the base plates 6081, 6051 and the enclosure 6100. In another alternative example, a hybrid compression seal may be employed in place of a lip seal which includes a multi-lobed cross sectional shape. For example, as shown in FIGS. 7I and 7J, each base plate 6081, 6051 may include a multi-lobed seal 6092 (e.g., constructed of an elastomeric material such as TPE or silicone) including at least one lobe, e.g., 2, 3, or more lobes. In the illustrated 3-lobe example, the multi-lobed seal 6092 includes a main body and three lobes 6093 projecting away from the main body. Each lobe 6093 may have a tapered shape and a rounded tip. In this arrangement, each of the lobes 6093 is configured and arranged to press separately on the interior faces of a respective groove in the first and second portions 6110, 6120 of the enclosure 6100, i.e., the grooves 6183, 6182 (in the second portion 6120) and the grooves 6181 and 6180 (in the first portion 6110), providing compliance for sealing and rigidity for easy assembly and robust groove retention. That is, the illustrated multi-lobe seal 6092 provides defence against the pressurised air, effectively providing the seal up to three opportunities to block pressurised air from escaping. Also, the self-retention of the seal within the groove is advantageous to reduce the necessary tension, e.g., in casing screws, in and around the high pressure region.

Similar to the example of the discrete-type blower outlet muffler described above, the blower outlet chamber 6003 of the integrated-type blower outlet muffler 6040 also includes space which is more closely associated with the inlet path of the RPT device, along which inlet air enters the enclosure. In particular, the space in question is the part of the blower outlet chamber 6003 of the blower outlet muffler 6040 which encloses at least a portion of the length of the inlet tubes 6053. That is, the space around the inlet tubes 6053 forms also part of the blower outlet chamber 6003 of the blower outlet muffler 6040, i.e., the outer surface of the inlet tube array 6053 forms one of the boundaries of the blower outlet chamber 6003 and cooperates with walls of the enclosure 6100, the blower outlet end suspension assembly 6080, and the inlet/outlet assembly 6050 to form the blower outlet muffler 6040. Again, the blower outlet chamber 6003 surrounds the tubes and, in doing so, extends beyond the location of the inlet path (in the form of the inlet tubes 6052). This increases the available muffling volume and improves the efficiency of the blower outlet muffler 6040.

The schematic diagram of the dynamic support of the blower 6010 within the enclosure 6100 and the differing degrees of freedom of an integrated-type blower outlet muffler configuration is shown in FIGS. 7K and 7L. The blower inlet end suspension 6020 is similar to that illustrated in FIGS. 6Q and 6R—it provides spring-like resilient support of the blower 6010 to the base plate 6027. Base plate 6027 includes a sealing lip 6028 along its perimeters, which provides spring-like resilient support of the base plate 6027 to the enclosure 6100. However, in this integrated-type blower outlet muffler configuration, there is no cantilevered body 6042 of the blower outlet muffler 6040, and therefore the blower outlet end suspension 6030 provides spring-like resilient support of the blower 6010 directly to the enclosure 6100, by way of base plate 6081. Base plate 6081 includes a sealing lip 6082 along its perimeters, which provides spring-like resilient support of the base plate 6081 to the enclosure 6100. Thus, the suspensions 6020, 6030 and the sealing lips 6028 and 6082 cooperate to provide an enhanced (to some extent—dual) suspension that resiliently suspends the blower 6010 within the enclosure 6100 to isolate vibrations or radiated noise. As noted above, it should be appreciated that more robust seals than lip seals 6028 and/or 6082 may be used around the base plates (e.g., thicker bead or multi-lobe seal providing a compression-type seal), which may provide a more rigid connection than the illustrated spring-like connection in the diagram.

5.4.1.4 Pressure Generator

In one form of the present technology, an RPT device 4000, 6000 may include a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.5 Transducer(s)

Transducers may be internal of the RPT device 4000, 6000, or external of the RPT device 4000, 6000. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

5.4.1.5.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 and representing a pressure is received by the central controller 4230.

5.4.1.5.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.6 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000, 6000.

In one form of the present technology, power supply 4210 provides electrical power to the RPT device 4000, 6000 only. In another form of the present technology, power supply 4210 provides electrical power to both RPT device 4000, 6000 and humidifier 5000.

5.4.2.2 Input Devices

In one form of the present technology, an RPT device 4000, 6000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000, 6000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 which may be implemented with processor-control instructions, expressed as computer programs stored in a non-transitory computer readable storage medium, such as memory 4260. In some forms of the present technology, the central controller 4230 may be integrated with an RPT device 4000, 6000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000, 6000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000, 6000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally, or alternatively, RPT device 4000, 6000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An RPT device 4000, 6000 in accordance with the present technology may optionally include an output device. An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs, such as with processor control instructions to be executed by one or more processor(s), stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the vent flow rate Qv, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

5.4.3.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas 4180, may be used as the total flow rate Qt. The interface pressure algorithm 4312 estimates the pressure drop ΔP through the air circuit 4170. The dependence of the pressure drop ΔP on the total flow rate Qt may be modelled for the particular air circuit 4170 by a pressure drop characteristic ΔP(Q). The interface pressure estimation algorithm, 4312 then provides as an output an estimated pressure, Pm, in the patient interface 3000. The pressure, Pm, in the patient interface 3000 may be estimated as the device pressure Pd minus the air circuit pressure drop ΔP.

5.4.3.1.2 Vent Flow Rate Estimation

In one form of the present technology, a vent flow rate estimation algorithm 4314 receives as an input an estimated pressure, Pm, in the patient interface 3000 from the interface pressure estimation algorithm 4312 and estimates a vent flow rate of air, Qv, from a vent 3400 in a patient interface 3000. The dependence of the vent flow rate Qv on the interface pressure Pm for the particular vent 3400 in use may be modelled by a vent characteristic Qv(Pm).

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

5.4.3.1.4 RESPIRATORY Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template ΠΦ((D).

5.4.3.2.2 Ventilation Determination

In one form of the present technology, a ventilation determination algorithm 4323 receives an input a respiratory flow rate Qr, and determines a measure indicative of current patient ventilation, Vent.

5.4.3.2.3 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

5.4.3.2.4 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.5 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.6 Determination of Airway Patency

In one form of the present technology, the central controller 4230 executes one or more airway patency determination algorithms 4327 for the determination of the extent of airway patency.

5.4.3.2.7 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

5.4.3.2.8 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

- Power failure (no power, or insufficient power)
- Transducer fault detection
- Failure to detect the presence of a component
- Operating parameters outside recommended ranges (e.g. pressure, flow rate, temperature, PaO2)
- Failure of a test alarm to generate a detectable alarm signal.

Upon detection of the fault condition, the corresponding algorithm 4340 signals the presence of the fault by one or more of the following:

- Initiation of an audible, visual &/or kinetic (e.g. vibrating) alarm
- Sending a message to an external device
- Logging of the incident 5.5 Air Circuit An air circuit 4170 in accordance with an aspect of the present technology is a conduit or a tube constructed and arranged to allow, in use, a flow of pressurised air to travel between two components such as RPT device 4000, 6000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.6 Humidifier 5.6.1 Humidifier Overview

In one form of the present technology there is provided a humidifier 5000 (e.g. as shown in FIG. 8A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 8A and FIG. 8B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 9 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Respiratory Therapy Modes

Various respiratory therapy modes may be implemented by the disclosed respiratory therapy system.

5.8.1 CPAP Therapy

In some implementations of respiratory pressure therapy, the central controller 4230 sets the treatment pressure Pt according to the treatment pressure equation ($Pt=A\Pi(\Phi, t)+P_0$) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$.

In CPAP therapy, the base pressure $P_0$ may be a constant value that is hard-coded or manually entered to the RPT device 4000, 6000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment ΔP, provided the resulting treatment pressure Pt would not exceed a maximum treatment pressure Pmax. In one implementation, the predetermined pressure increment ΔP and maximum treatment pressure Pmax are 1 cmH20 and 25 cmH2O respectively. In other implementations, the pressure increment 4P can be as low as 0.1 cmH2O and as high as 3 cmH2O, or as low as 0.5 cmH2O and as high as 2 cmH2O. In other implementations, the maximum treatment pressure Pmax can be as low as 15 cmH2O and as high as 35 cmH2O, or as low as 20 cmH2O and as high as 30 cmH2O. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant τ of the exponential decrease of $P_0$ is 60 minutes, and the minimum treatment pressure Pmin is 4 cmH2O. In other implementations, the time constant τ could be as low as 1 minute and as high as 300 minutes, or as low as 5 minutes and as high as 180 minutes. In other implementations, the minimum treatment pressure Pmin can be as low as 0 cmH2O and as high as 8 cmH2O, or as low as 2 cmH2O and as high as 6 cmH2O. Alternatively, the decrement in $P_0$ could be predetermined, so the decrease in $P_0$ to the minimum treatment pressure Pmin in the absence of any detected events is linear.

5.8.2 Bi-Level Therapy

In other implementations of this form of the present technology, the value of amplitude A in equation ($Pt=A\Pi(\Phi, t)+P_0$) may be positive. Such implementations are known as bi-level therapy, because in determining the treatment pressure Pt using equation ($Pt=A\Pi(\Phi, t)+P_0$) with positive amplitude A, the therapy parameter determination algorithm 4329 oscillates the treatment pressure Pt between two values or levels in synchrony with the spontaneous respiratory effort of the patient 1000. That is, based on the typical waveform templates Π(Φ, t) described above, the therapy parameter determination algorithm 4329 increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water (H2O) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including cmH2O, g-f/cm2 and hectopascal. 1 cmH2O is equal to 1 g-f/cm2 and is approximately 0.98 hectopascal (1 hectopascal=100 Pa=100 N/m2=1 millibar 0.001 atm). In this specification, unless otherwise stated, pressure is given in units of cmH2O.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 2B to FIG. 2F, which illustrate examples of cross-sections at point p on a surface, and the resulting plane curves. FIGS. 2B to 2F also illustrate an outward normal vector at p. The outward normal vector at p points away from the surface. In some examples we describe the surface from the point of view of an imaginary small person standing upright on the surface.

5.9.2.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 2B (relatively large positive curvature compared to FIG. 2C) and FIG. 2C (relatively small positive curvature compared to FIG. 2B). Such curves are often referred to as concave.

Zero curvature: If the curve at p is a straight line, the curvature will be taken to be zero (if the imaginary small person leaves the point p, they can walk on a level, neither up nor down). See FIG. 2D.

Negative curvature: If the curve at p turns away from the outward normal, the curvature in that direction at that point will be taken to be negative (if the imaginary small person leaves the point p they must walk downhill). See FIG. 2E (relatively small negative curvature compared to FIG. 2F) and FIG. 2F (relatively large negative curvature compared to FIG. 2E). Such curves are often referred to as convex.

5.9.2.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 2B to 2F could be examples of such multiple cross-sections at a particular point.

Figure 2B:
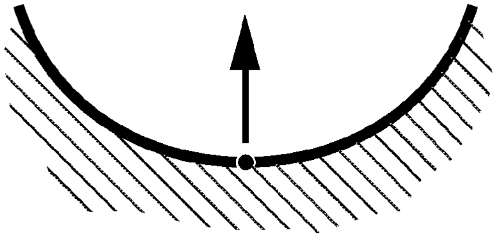
Figure 2C:
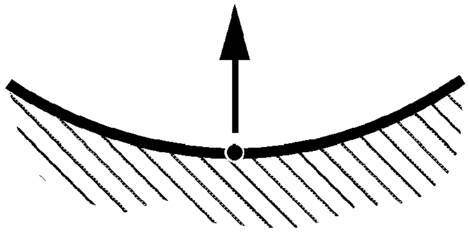
Figure 2D:
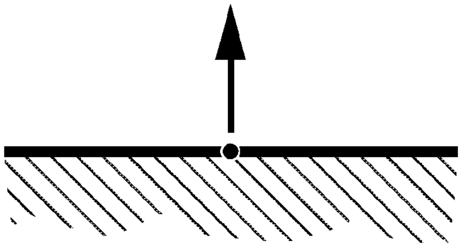
Figure 2E:
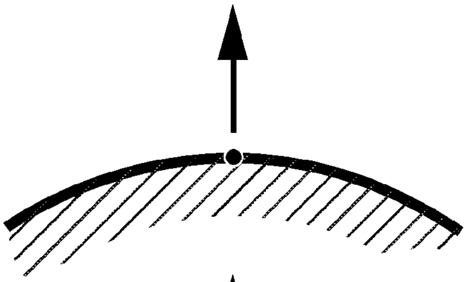
Figure 2F:
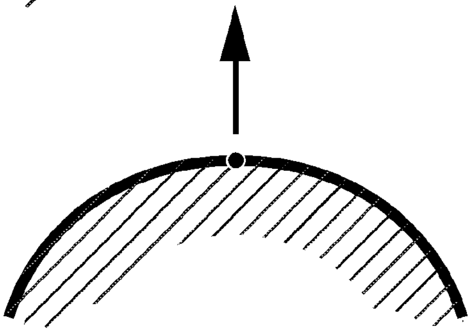

Principal curvatures and directions: The directions of the normal planes where the curvature of the curve takes its maximum and minimum values are called the principal directions. In the examples of FIG. 2B to FIG. 2F, the maximum curvature occurs in FIG. 2B, and the minimum occurs in FIG. 2F, hence FIG. 2B and FIG. 2F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9.2.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix. A typical human right ear comprises a helix, which is a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule, or alternatively by a left-hand rule.

Osculating plane: The plane containing the unit tangent vector and the unit principal normal vector.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path).

5.9.2.4 Holes

A surface may have a one-dimensional hole, e.g. a hole bounded by a plane curve or by a space curve. Thin structures (e.g. a membrane) with a hole, may be described as having a one-dimensional hole.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit.

5.10 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.11 REFERENCE SIGNS LIST

| Feature Item | Number |
|---|---|
| patient | 1000 |
| bed partner | 1100 |
| patient interface | 3000 |
| seal - forming structure | 3100 |
| plenum chamber | 3200 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| air circuit | 4171 |
| supplementary gas | 4180 |
| electrical components | 4200 |
| PCBA | 4202 |
| power supply | 4210 |

-continued 5.11 REFERENCE SIGNS LIST

| Feature Item | Number |
| --- | --- |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre - processing module | 4310 |
| interface pressure algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| method | 4340 |
| method | 4500 |
| step | 4520 |
| step | 4530 |
| step | 4540 |
| step | 4550 |
| step | 4560 |
| humidifier | 5000 |
| humidifier inlet | 5002 |
| humidifier outlet | 5004 |
| humidifier base | 5006 |
| humidifier reservoir | 5110 |
| conductive portion | 5120 |
| humidifier reservoir dock | 5130 |
| locking lever | 5135 |
| water level indicator | 5150 |
| humidifier transducer | 5210 |
| pressure transducer | 5212 |
| flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |
| RPT device | 6000 |
| device inlet chamber | 6001 |
| blower inlet chamber | 6002 |
| blower outlet chamber | 6003 |
| blower | 6010 |
| blower axis | 6010ax |
| blower inlet | 6012 |
| blower inlet axis | 6012ax |
| blower inlet opening | 6012op |
| blower outlet | 6014 |
| blower inlet end suspension | 6020 |
| flow tube array | 6025 |
| flow tube | 6026 |
| flow tube axis | 6026ax |

-continued 5.11 REFERENCE SIGNS LIST

| Feature Item | Number |
| --- | --- |
| flow tube opening | 6026op |
| base plate | 6027 |
| sealing lip | 6028 |
| blower outlet end suspension | 6030 |
| outer portion | 6031 |
| inner portion | 6032 |
| gusset portion | 6033 |
| blower outlet muffler | 6040 |
| main body | 6042 |
| central wall portion | 6043 |
| end wall portion | 6045 |
| opening | 6045o1 |
| opening | 6045o2 |
| end wall portion | 6047 |
| tube portion | 6047t |
| opening | 6047o |
| cut-out | 6049 |
| inlet/outlet assembly | 6050 |
| base plate | 6051 |
| inlet tube array | 6052 |
| inlet tube | 6053 |
| outlet tube | 6054 |
| outlet tube axis | 6054ax |
| pressure port | 6055 |
| outlet seal | 6060 |
| end portion | 6061 |
| lip | 6062 |
| sealing assembly | 6070 |
| sealing lip | 6072 |
| inlet end seal | 6074 |
| port seal | 6075 |
| seal portion | 6076 |
| seal portion | 6077 |
| blower outlet end suspension assembly | 6080 |
| base plate | 6081 |
| sealing lip | 6082 |
| opening | 6084o1 |
| opening | 6084o2 |
| top case | 6090 |
| multi-lobe seal | 6092 |
| lobe | 6093 |
| enclosure | 6100 |
| first portion | 6110 |
| first wall portion | 6112 |
| first interior surface | 6114 |
| first exterior surface | 6116 |
| first intermediate surface | 6118 |
| second portion | 6120 |
| second wall portion | 6122 |
| second interior surface | 6124 |
| second exterior surface | 6126 |
| second intermediate surface | 6128 |
| rigidized wall portion | 6130 |
| step | 6131 |
| face | 6132 |
| step | 6133 |
| end wall | 6135 |
| transition region | 6139 |
| slot | 6141 |
| lip | 6141L |
| slot | 6142 |
| lip | 6142L |
| fastener | 6150 |
| bosses | 6160 |
| fastener holes | 6165 |
| flange | 6166 |
| groove | 6180 |
| groove | 6181 |
| groove | 6182 |
| groove | 6183 |
| groove | 6185 |
| wall constrainment arrangement | 6200 |
| tongue | 6210 |
| groove | 6220 |
| inner side wall | 6222 |

-continued 5.11 REFERENCE SIGNS LIST

| Feature Item | Number |
|---|---|
| inner side wall surface | 6223 |
| outer side wall | 6224 |
| outer side wall surface | 6225 |
| seal | 6300 |
| thick region | 6310 |
| thin region | 6320 |
| device inlet muffler | 6350 |
| blower inlet muffler | 6400 |
| front face | 6410 |

The invention claimed is:

1. A respiratory pressure therapy device comprising:

an enclosure including a first portion and a second portion, the second portion configured to engage the first portion in an assembled configuration;

a blower to provide a supply of air for respiratory pressure therapy, the blower enclosed at least partially in the enclosure, wherein the blower includes a blower inlet and a blower outlet, the blower outlet including an axis that is coaxial with an axis of the blower inlet;

a plurality of flow tubes enclosed at least partially in the enclosure, the plurality of flow tubes arranged upstream of the blower inlet of the blower; and a blower inlet muffler comprising a noise attenuating material, wherein the noise attenuating material is configured and arranged to face the blower inlet of the blower such that the axis of the blower inlet passes through a thickness of the noise attenuating material, wherein the noise attenuating material is configured and arranged to face an opening of at least one of the plurality of flow tubes such that an axis of the opening of at least one of the plurality of flow tubes passes through the thickness of the noise attenuating material, and wherein each of the first portion and the second portion of the enclosure supports and retains at least a portion of the noise attenuating material facing the blower inlet and the opening of at least one of the plurality of flow tubes in the enclosure.

2. The respiratory pressure therapy device according to claim 1, wherein the noise attenuating material comprises foam.

3. The respiratory pressure therapy device according to claim 1, wherein the noise attenuating material comprises a first foam piece supported by the first portion of the enclosure and a second foam piece support by the second portion of the enclosure.

4. The respiratory pressure therapy device according to claim 3, wherein each of the first portion and the second portion includes a slot to support a respective one of the first foam piece and the second foam piece.

5. The respiratory pressure therapy device according to claim 3, wherein the first foam piece and the second foam piece are supported in the enclosure such that a front face or surface of at least one of the first foam piece and the second foam piece faces the blower inlet of the blower.

6. The respiratory pressure therapy device according to claim 1, wherein the blower inlet muffler comprises a chamber arranged to face the blower inlet of the blower such that an axis of the blower inlet passes through the chamber.

7. The respiratory pressure therapy device according to claim 6, wherein at least a portion of a wall of the chamber is rigidized.

8. The respiratory pressure therapy device according to claim 7, wherein the rigidized wall portion of the chamber faces the blower inlet, such that the axis of the blower inlet passes through rigidized wall portion.

9. The respiratory pressure therapy device according to claim 7, wherein the rigidized wall portion is rigidized by way of a wall curvature.

10. The respiratory pressure therapy device according to claim 7, wherein the rigidized wall portion includes a tongue and groove engagement between the first portion and the second portion of the enclosure.

11. The respiratory pressure therapy device according to claim 1, wherein the blower inlet muffler further comprises a blower inlet chamber located upstream of the blower inlet of the blower, and wherein the noise attenuating material includes a front face or surface that forms a boundary of the blower inlet chamber.

12. The respiratory pressure therapy device according to claim 11, wherein the front face or surface of the noise attenuating material is arranged directly opposite and faces the blower inlet and the opening of at least one of the plurality of flow tubes.

13. The respiratory pressure therapy device according to claim 11, wherein the front face or surface of the noise attenuating material forms a boundary of an air flow path that extends from the plurality of flow tubes to the blower inlet of the blower.

14. The respiratory pressure therapy device according to claim 1, wherein an inlet into the enclosure and an outlet out of the enclosure are formed on the same side of the enclosure.

15. The respiratory pressure therapy device according to claim 1, wherein the thickness of the noise attenuating material is about 4-10 mm.

16. The respiratory pressure therapy device according to claim 1, wherein the noise attenuating material is axially displaced or spaced from the blower inlet of the blower and from the plurality of flow tubes by about 5-40 mm.

* * * * *